US007847064B2

(12) United States Patent
Beachy et al.

(10) Patent No.: US 7,847,064 B2
(45) Date of Patent: Dec. 7, 2010

(54) METHODS AND COMPOSITIONS FOR REGULATING GENE EXPRESSION IN PLANT CELLS

(75) Inventors: Roger N. Beachy, St. Louis, MO (US); Maria Isabel Ordiz Luis, St. Louis, MO (US); Shunhong Dai, St. Louis, MO (US)

(73) Assignee: Donald Danforth Plant Science Center, St. Louis, MO (US)

( * ) Notice: Subject to any disclaimer, the term of this patent is extended or adjusted under 35 U.S.C. 154(b) by 860 days.

(21) Appl. No.: 11/347,750

(22) Filed: Feb. 3, 2006

(65) Prior Publication Data

US 2007/0298499 A1 Dec. 27, 2007

Related U.S. Application Data

(63) Continuation-in-part of application No. 10/888,613, filed on Jul. 9, 2004, now Pat. No. 7,517,689.

(51) Int. Cl.
*C07K 14/005* (2006.01)

(52) U.S. Cl. .................................... 530/350; 435/235.1

(58) Field of Classification Search ..................... None
See application file for complete search history.

(56) References Cited

U.S. PATENT DOCUMENTS

| | | | |
|---|---|---|---|
| 5,824,857 | A | 10/1998 | Beachy et al. |
| 2001/0047092 | A1 | 11/2001 | Bruce et al. |

FOREIGN PATENT DOCUMENTS

| | | |
|---|---|---|
| WO | WO 01/53476 | 7/2001 |
| WO | WO 02/46366 | 6/2002 |

OTHER PUBLICATIONS

Kodadek et al, Chemistry & Biology, Apr. 1995, vol. 2, pp. 187-194.*

Int. Search Report WO 01/53476, Jan. 31, 2002, Bruce et al.

Int. Search Report WO 02/46386, Jan. 30, 2003, Beachy et al.

Chen, G., Rothnie, H., He, X., Hohn, T., and Futterer, J. (1996). Efficient Transcription from the Rice Tungro Bacilliform Virus Promoter Requires Elements Downstream of the Transcription Start Site. *J. of Virology*. 70, 8411-21.

Christopherson, K.S., Mark, M.R., Bajaj, V. and Godowski, P.J. (1992). Ecdysteroid-dependent regulation of genes in mammalian cells by a *Drosophila* ecdysone receptor and chimeric transactivators. *Proc. Natl. Acad. Sci. U.S.A.* 89, 6314-6318.

Fukazawa, J., Sakai, T., Ishida, S., Yamaguchi, I., Kamiya, Y. and Takahashi, Y. (2000). Repression of shoot growth, a bZIP transcriptional activator, regulates cell elongation by controlling the level of gibberellins. *Plant Cell* 12, 901-15.

He, X., Hohn, T. and Futterer, J. (2000). Transcriptional activation of the rice tungro bacilliform virus gene is critically dependent on an activator element located immediately upstream of the TATA box. *J. Biol. Chem.* 275, 11799-808.

He, X., Futterer, J., and Hohn, T. (2001). Sequence-specific and Methylation-dependent and—independent Binding of Rice Nuclear Proteins to a Rice Tungro Bacilliform Virus Vascular Bundle Expression Element. *J Biol Chem* 276 2644-2651.

He, X., Futterer, J., and Hohn, T. (2002). Contribution of downstream promoter elements to transcriptional regulation of the rice tungro bacilliform virus promoter. *Nucleic Acids Research* 30, 497-506.

Ordiz, M.I., Barbas, C.F., III, and Beachy, R.N. (2002). Regulation of transgene expression in plants with polydactyl zinc finger transcription factors. *Proc. Natl. Acad. Sci. U.S.A.* 99, 13290-95.

Padidam, M., Gore, M., Lu, D.L., and Smirnova, O. (2003). Chemical-inducible, ecdysone receptor-based gene expression system for plants. *Transgenic Res.* 12, 101-109.

Petruccelli, S., Dai, S., Carcamo, R., Yin, Y., Chen, S. and Beachy, R.N. (2001). Transcription factor RF2a alters expression of the rice tungro bacilliform virus promoter in transgenic tobacco plants. *Proc. Natl. Acad. Sci. U.S.A.* 98, 7635-40.

Segal, D.J., Stege J.T., and Barbas C.F. (2003). Zinc fingers and a green thumb: manipulating gene expression in plants. *Curr. Opin. Plant Biol.* 6, 163-68.

Toledo-Ortiz, G., Huq, E., and Quail, P.H. (2003). The Arabidopsis Basic/Helix-Loop-Helix Transcription Factor Family, *The Plant Cell* 15, 1749-70.

Yin, Y. and Beachy, R.N. (1995). The regulatory regions of the rice tungro bacilliform virus promoter and interacting nuclear factors in rice (Oryza sativa L.). *Plant J.* 7, 969-80.

Yin, Y., Chen, L. and Beachy, R. (1997). Promoter elements required for phloem-specific gene expression from the RTBV promoter in rice. *Plant J.* 12, 1179-88.

Yin, Y., Zhu, Q., Dai, S., Lamb, C., and Beachy, R.N. (1997). RF2a, a bZIP transcriptional activator of the phloem-specific rice tungro bacilliform virus promoter, functions in vascular development. *EMBO J.* 16 5247-59.

Zhu, Q., Ordiz, M., Dabi, T., Beachy, R., and Lamb, C. (2002). Rice TATA Binding Protein Interacts Functionally with Transcription Factor IIB and the RF2a bZIP Transcriptional Activator in an Enhanced Plant in Vitro Transcription System *The Plant Cell* 14 795-803.

* cited by examiner

*Primary Examiner*—James S Ketter
(74) *Attorney, Agent, or Firm*—Bryan Cave LLP

(57) ABSTRACT

Novel chimeric plant promoter sequences are provided, together with plant gene expression cassettes comprising such sequences. In certain preferred embodiments, the chimeric plant promoters comprise the BoxII cis element and/or derivatives thereof. In addition, novel transcription factors are provided, together with nucleic acid sequences encoding such transcription factors and plant gene expression cassettes comprising such nucleic acid sequences. In certain preferred embodiments, the novel transcription factors comprise the acidic domain, or fragments thereof, of the RF2a transcription factor. Methods for using the chimeric plant promoter sequences and novel transcription factors in regulating the expression of at least one gene of interest are provided, together with transgenic plants comprising such chimeric plant promoter sequences and novel transcription factors.

14 Claims, 29 Drawing Sheets

| | |
|---|---|
| Box II | 5' CCAGTGTGCCCCTGG 3' |
| Box IIm1 | 5' CCAGTGTG**G**C**G**CTGG 3' |
| Box IIm2 | 5' **GG**AGTGTGCCCCT**TC** 3' |

Figure 6

| | RF2a | | RF2b | |
|---|---|---|---|---|
| | Ka (1/M) | Kd(M) | Ka (1/M) | Kd(M) |
| Box II | $8.67 \times 10^6$ | $1.15 \times 10^{-7}$ | $2.19 \times 10^6$ | $4.57 \times 10^{-7}$ |
| Box II m1 | $1.08 \times 10^7$ | $9.26 \times 10^{-8}$ | $4.17 \times 10^6$ | $2.40 \times 10^{-7}$ |
| Box II m2 | $8.13 \times 10^6$ | $1.23 \times 10^{-7}$ | $1.85 \times 10^6$ | $5.40 \times 10^{-7}$ |

Figure 8

| | | | | | |
|---|---|---|---|---|---|
| Box II | -48 | TATA | +1 | +8 | p-1.0hBoxII-48CaMV |
| | -48 | TATA | +1 | +8 | p-48CaMV |
| Box II | -53 | TATA | +1 | +8 | p-1.5hBoxII-53CaMV |
| | -53 | TATA | +1 | +8 | p-53CaMV |
| Box II | -69 | TATA | +1 | +8 | p-3.0hBoxII-69CaMV |
| | -69 | TATA | +1 | +8 | p-69CaMV |
| Box II | -74 | TATA | +1 | +8 | p-3.5hBoxII-74CaMV |
| | -74 | TATA | +1 | +8 | p-74CaMV |
| Box II | -90 | TATA | +1 | +8 | p-5.0hBoxII-90CaMV |
| | -90 | TATA | +1 | +8 | p-90CaMV |
| Box II | -95 | TATA | +1 | +8 | p-5.5hBoxII-95CaMV |
| | -95 | TATA | +1 | +8 | p-95CaMV |

-1.0hBoxII-48CaMV:
tgatcaaagcttCCAGTGTGCCCCTGG*tcgcaagacccttcctc*

-1.5hBoxII-53CaMV:
tgatcaaagcttCCAGTGTGCCCCTGG*atccttcgcaagaccct*

-1.5hBoxII-53CaMV-c:
tgatcaaagctt*atccttcgcaagaccct*

-3.0hBoxII-69CaMV:
tgatcaaagcttCCAGTGTGCCCCTGG*gacgcacaatcccacta*

-3.5hBoxII-74CaMV:
tgatcaaagcttCCAGTGTGCCCCTGG*gggatgacgcacaatcc*

-3.5hBoxII-74CaMV-c:
tgatcaaagctt*gggatgacgcacaatcc*

-5.0hBoxII-90CaMV:
tgatcaaagcttCCAGTGTGCCCCTGG*atctccactgacgtaag*

-5.5hBoxII-95CaMV:
tgatcaaagcttCCAGTGTGCCCCTGG*gtgatatctccactgac*

-5.5hBoxII-95CaMV-c:
tgatcaaagctt*gtgatatctccactgac*

Figure 12

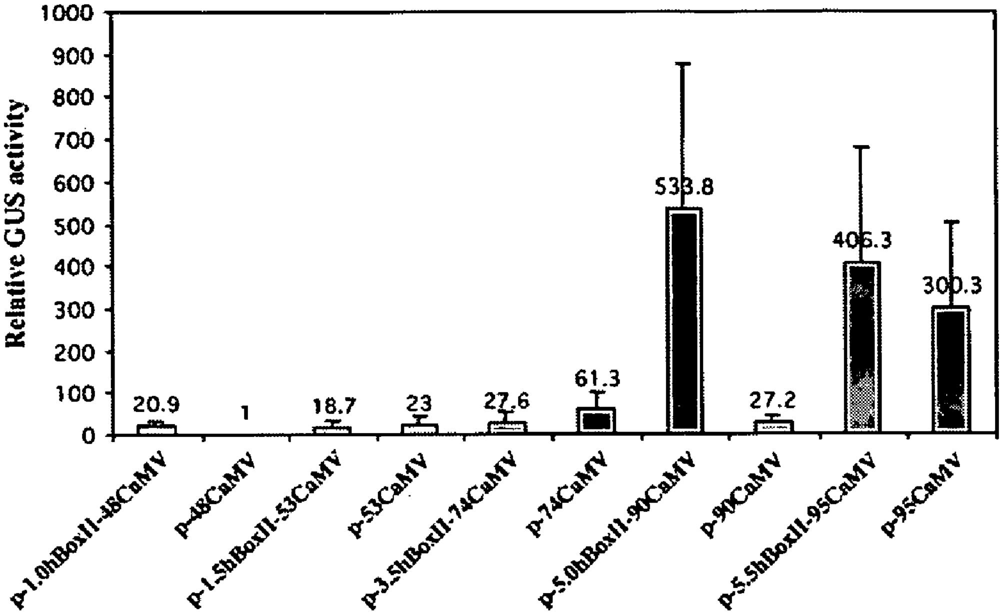
B
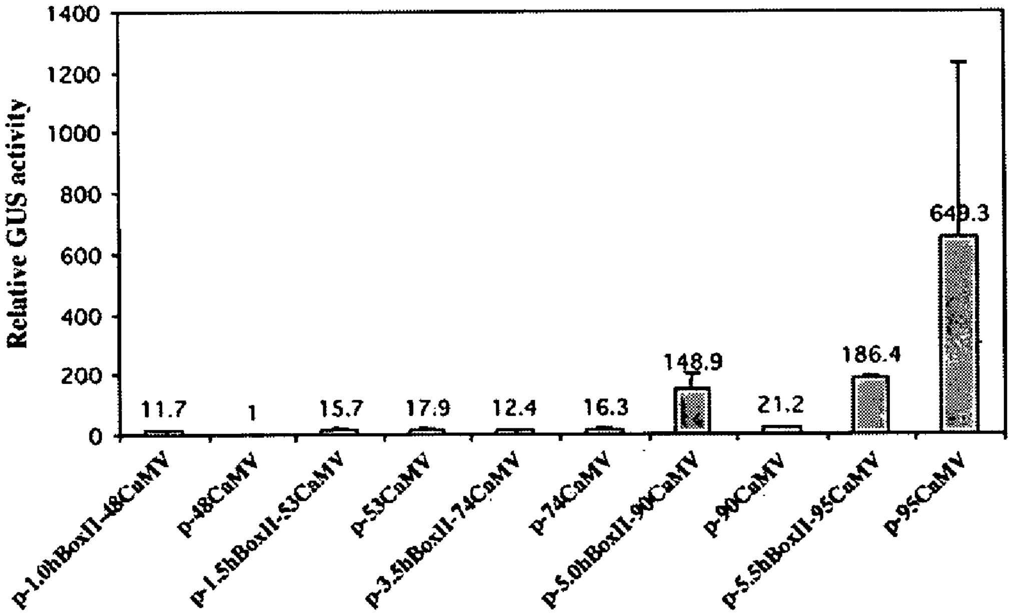
Figure 14

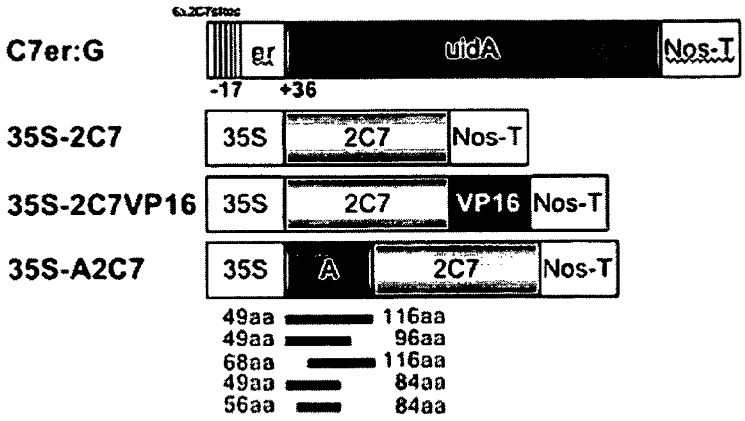
A
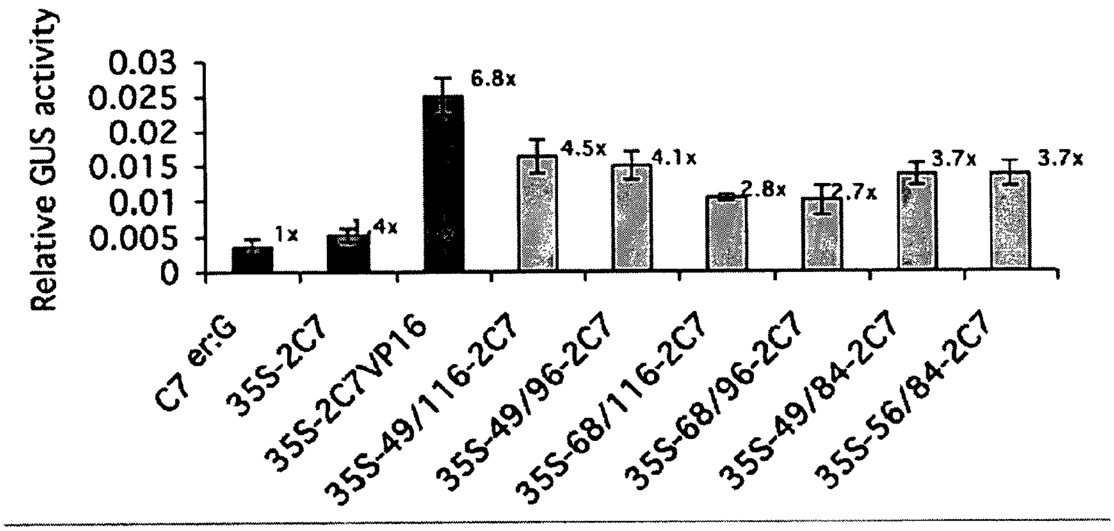
B
Figure 24

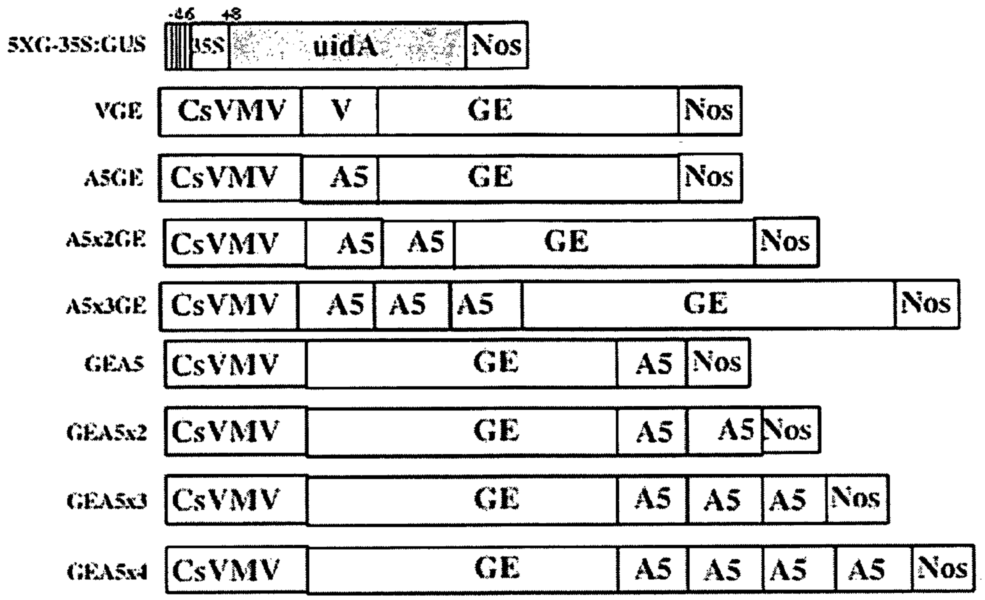
A
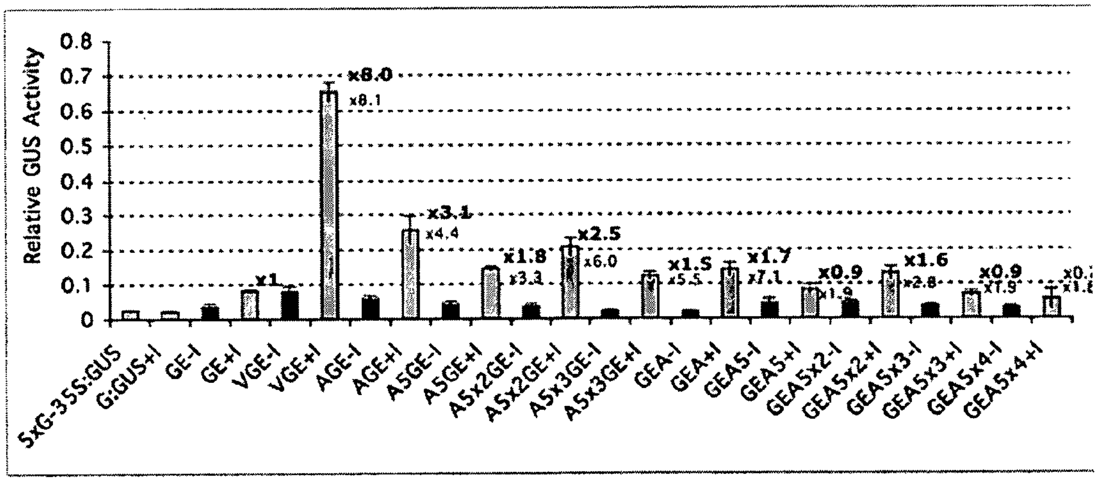
B
Figure 27

METHODS AND COMPOSITIONS FOR REGULATING GENE EXPRESSION IN PLANT CELLS

CROSS-REFERENCE TO RELATED APPLICATIONS

This application is a continuation-in-part and claims the benefit of U.S. patent application Ser. No. 10/888,613, filed Jul. 9, 2004, now U.S. Pat. No. 7,517,689 which is incorporated herein by reference.

This invention was supported in part by grant number NNA04CC29G from the National Aeronautics and Space Administration (NASA). The U.S. Government may have certain rights in the invention.

FIELD OF THE INVENTION

The present invention relates to the field of molecular biology. In particular, the invention relates to methods and compositions that can be used to regulate gene expression. Still more particularly, the invention relates to methods and compositions that can be used to initiate and/or enhance the expression of at least one gene of interest in plant cells.

BACKGROUND OF THE INVENTION

Gene expression may be regulated in several ways, which include the activation or suppression of transcription, the differential processing and stabilization of messenger RNA ("mRNA") and the extent of translation of the mRNA. The control of transcription plays a particularly critical role in the regulation of gene expression in eukaryotic cells. There are several structural elements that are involved in the regulation of transcription.

Promoters represent a class of nucleic acid structures that are involved in the regulation of transcription. In general, promoters are located next to the transcription start site and interact with RNA polymerase, either directly or indirectly. Promoters often comprise several discrete "cis elements," each of which may be recognized by one or more trans-acting regulatory proteins known as transcription factors. Among the various cis elements well-known in the art is the "TATA box," which is known to interact with certain regulatory proteins, e.g., transcription factors, and is generally located about 20-30 base pairs upstream from the transcription initiation site.

The binding of such transcription factors to promoters or other regulatory sequences is often responsible for the initiation, maintenance and/or down-regulation of transcription. A typical gene-specific eukaryotic transcription factor includes a DNA-binding domain and one or more additional domains that influence the activation or repression of transcription, e.g., "trans-acting domains." Transcription factors bind in the general proximity (although occasionally at great distances) of the point of transcription initiation of a gene. Such transcription factors often act to influence the efficiency of formation or function of a transcription initiation complex at the promoter. Transcription factors can act in a positive fashion (transactivation) or in a negative fashion (transrepression). Furthermore, the effect that transcription factors may have on gene expression can be constitutive (always "on") or conditional.

Over the years, several classes of DNA-binding domains of various transcription factors have been characterized and the nucleic acid sequences to which such domains interact identified. Non-limiting examples of such domains include motifs known as the leucine zipper, the bZIP domain, the zinc-finger, the homeobox, the basic helix-loop-helix and others. The trans-acting domains of transcription factors are often characterized as having a high content of specific amino acids, which include domains rich in acidic amino acids, proline or glutamine (Giniger et al., 1985; Meshi and Iwabuchi, 1995; Mitchell and Tjian, 1989). Acidic domains have been reported to possess activation functions that include interactions with TATA-binding proteins ("TBP") (Truant et al., 1993), TBP-associated factors ("TAFs") (Uesugi et al., 1997), TFIIA (Pugh, 2000), TFIIB (Klemm et al., 1995) and other general transcription complexes (Stargell and Struhl, 1995).

Beachy, in U.S. Pat. No. 5,824,857 entitled "Plant Promoter," described the promoter from the rice tungro bacilliform virus ("RTBV"). The '857 patent discloses that the RTBV promoter causes preferential gene expression in plant vascular tissue. The patent also discloses that the RTBV promoter can be used to drive expression in most plants, whether monocotyledonous or dicotyledonous, and is particularly suited to rice. The patent further discloses the transformation of plants by inserting the coding sequence of the RTBV promoter and a heterologous gene of interest to obtain transgenic plants that express the gene of interest in vascular tissue.

Yin and Beachy, in "The regulatory regions of the rice tungro bacilliform virus promoter and interacting nuclear factors in rice (*Oryza sativa* L.), *The Plant Journal,* 7(6): 969-980 (1995)," described the E fragment (−164 to +45 in relation to the transcription start site) within the RTBV promoter, which was shown to be sufficient to cause tissue-specific gene expression. The article also disclosed a critical cis element, Box II (−53 to −39), within the E fragment that was shown to be essential for promoter activity. The same authors identified other cis elements of the RTBV promoter in "Promoter elements required for phloem-specific gene expression from the RTBV promoter in rice, *The Plant Journal:* 12(5): 1179-1188 (1997)," including the ASL Box (−98 to −79) and a GATA motif (−143 to −135). Together, these cis elements were shown to confer phloem-specific reporter gene expression.

Yin et al., in "RF2a, a bZIP transcriptional activator of phloem-specific rice tungro bacilliform virus promoter, function in vascular development, *The EMBO Journal,* 16(17): 5247-5259 (1997)," identified a 1.8 Kb transcription factor consisting of 368 amino acids—designated as RF2a. The RF2a transcription factor is currently known to represent a bZIP transcription activator found in rice plants that contains acidic, proline-rich and glutamine-rich putative functional domains. RF2a has been shown to bind the Box II element of the RTBV promoter and stimulate Box II-dependent transcription in vitro. Another bZIP protein, RF2b, has been isolated through interaction with RF2a, which also has been shown to interact with the Box II element.

The inventors have discovered that the Box II cis-element of the RTBV promoter is portable and that it can be used to modulate gene expression in unrelated promoters in connection with RF2a and/or RF2b. That is, until now, it was not known that the Box II element, and similar sequences, could be used in chimeric promoters to regulate gene expression in connection with RF2a and/or RF2b. What's more, the inventors have discovered that the acidic domain of RF2a is particularly critical to the activation function of this transcription factor and, moreover, that it can be transferred to unrelated DNA-binding proteins to modulate gene expression. Accordingly, the inventors have discovered a new system for modulating gene expression, as described further below.

SUMMARY OF THE INVENTION

Until now, it was not known that the Box II element of the RTBV promoter is portable and that it can be used in connection with unrelated promoters to activate and/or enhance gene expression in the presence of RF2a and/or RF2b. Similarly, the inventors have discovered that operational derivatives of the Box II element can be used to regulate gene expression in like fashion. Still further, the inventors have discovered that the acidic domain of RF2a is also portable and that it can be transferred to unrelated DNA-binding proteins to activate and/or enhance gene expression.

Accordingly, the present invention exploits the portability of the Box II sequence, its operational derivatives and its interaction with RF2a and/or RF2b to provide novel compositions and methods that can be used to control the expression of one or more genes of interest. Further, the present invention provides novel transcription factors, which contain at least one domain that comprises an amino acid sequence that is at least substantially similar to the acidic domain of RF2a, which can be used in connection with unrelated DNA-binding domains to regulate gene expression.

In one preferred embodiment, the invention provides novel chimeric promoters, which comprise (a) nucleic acid sequences derived from any promoter (other than the RTBV promoter), or promoter fragment, that are capable of driving gene expression in plant cells and (b) at least one nucleic acid sequence selected from the group consisting of: (i) SEQ ID NO:1; (ii) SEQ ID NO:2; (iii) SEQ ID NO:3; and (iv) sequences that are substantially similar to either SEQ ID NO:1, 2, or 3. The nucleic acid sequence consisting of SEQ ID NO:1, 2, 3 or sequences substantially similar to any of the foregoing sequences, is, preferably, located in a position that is approximately 7 nucleotides from the TATA box of the promoter, or promoter fragment, plus one or more full turns of DNA helix.

In another preferred embodiment, the invention provides plant gene expression cassettes that comprise a first chimeric promoter, which comprises a nucleic acid sequence selected from the group consisting of: (i) SEQ ID NO:1; (ii) SEQ ID NO:2; (iii) SEQ ID NO:3; and (iv) sequences that are substantially similar to either SEQ ID NO:1, 2, or 3. The first chimeric promoter is operatively linked to any gene of interest. The nucleic acid sequence consisting of SEQ ID NO:1, 2, 3 or sequences substantially similar to any of the foregoing sequences, is, preferably, located in a position that is approximately 7 nucleotides from the TATA box of the promoter, or promoter fragment, plus one or more full turns of DNA helix. The expression cassettes may further comprise a second promoter operatively linked to a nucleic acid sequence that encodes a polypeptide, which comprises an amino acid sequence selected from the group consisting of: (i) SEQ ID NO:4; (ii) SEQ ID NO:5; (iii) SEQ ID NO:6; and (iv) sequences that are substantially similar to either SEQ ID NO:4, 5 or 6.

In a related embodiment, the invention provides plant gene expression cassettes similar to those described above, wherein the expression of the second promoter is capable of being chemically-induced. Accordingly, expression of the nucleic acid sequence to which the second promoter is operatively linked is stimulated or enhanced by applying an effective amount of the chemical inducer to the plant cells, embryos, or tissues that have been transformed with the expression cassette of the present invention.

In a further embodiment, the present invention provides plant gene expression cassettes comprising (i) a first promoter, which comprises a nucleic acid sequence that is capable of interacting with at least one DNA-binding domain of at least one polypeptide, operatively linked to a gene of interest and (ii) a second promoter operatively linked to a nucleic acid sequence that encodes a polypeptide, which comprises an amino acid sequence that is at least substantially similar to SEQ ID NO:6 and a DNA-binding domain that is capable of interacting with the corresponding nucleic acid sequence of the first promoter. In a related embodiment, the present invention provides that the expression of the second promoter may be chemically-induced.

In other embodiments, novel transcription factors and uses thereof are provided. In particular, the inventors have discovered that the acidic domain of RF2a (SEQ ID NO:6), and sequences substantially similar to SEQ ID NO:6, can be fused to unrelated transcription factors, or transcription factor-like complexes, to regulate gene expression. More specifically, the invention provides that novel transcription factors, which comprise the acidic domain of RF2a and at least one DNA-binding domain, can be used to modulate the expression of one or more genes of interest, which are driven by promoters that comprise nucleic acid sequences recognized by at least one DNA-binding domain of such novel transcription factors.

In other embodiments, the invention provides methods of regulating the expression level of at least one gene of interest comprising transforming a plant cell with at least one plant gene expression cassette of the present invention. Still further, the invention provides methods of regulating the expression level of at least one gene of interest comprising (a) transforming plant cells with at least one plant gene expression cassette of the present invention, wherein the cassette comprises a chemically-inducible promoter operatively linked to a nucleic acid sequence that encodes a polypeptide comprising (i) an amino acid sequence that is at least substantially similar to SEQ ID NO:6 and (ii) an amino acid sequence that is capable of interacting with another promoter operatively linked to a gene of interest, wherein the interaction initiates and/or enhances the expression of the gene of interest and (b) contacting plant cells, embryos, tissues, roots, etc., directly or indirectly, derived from the transformed plant cells with an activating amount of the expression-inducing chemical.

In other embodiments, the invention provides that two or more chimeric promoters containing the Box II element and/or its operational derivatives, which are operatively linked to one or more genes of interest, can be used in connection with RF2a- and/or RF2b-encoding sequences to achieve a "cascade-type" system. In this embodiment, the expression of RF2a and/or RF2b activates and/or enhances the expression of the nucleic acid sequences to which the one or more chimeric promoters are operatively linked. Still further, the nucleic acid sequence encoding the RF2a and/or RF2b protein may be operably linked to a chemically-inducible promoter. In such embodiment, upon contacting plant cells, embryos, or tissues, which have been transformed with such nucleic acid sequences, with the expression-inducing chemical, the RF2a and/or RF2b transcription factor is produced and subsequently interacts with the Box II element and/or its operational derivatives to regulate gene expression. This interaction, of course, results in the synchronized activation or enhancement of expression of all Box II-dependent genes (or all genes operatively linked to promoters containing operational derivatives of Box II).

In other embodiments, the invention provides that at least one chimeric promoter containing the Box II element and/or its operational derivatives, which is operatively linked to one or more genes of interest, can be used in combination with RF2a- and/or RF2b-encoding sequences to "turn-off" or modulate the expression of one or more unrelated endogenous and/or exogenous genes of interest. The foregoing combination, for example, can be used to activate or enhance the expression of particular sequences that encode molecules that selectively hybridize to specific target nucleic acid sequences. The hybridization of an oligomeric compound, for example, with its target nucleic acid sequence can have the effect of interfering with the normal function of the target sequence (this effect is generally referred to as "antisense"). The functions of DNA that can be affected in this embodiment, for example, include replication and transcription. The functions of RNA that can be affected include translocation of the RNA to the site of protein translation, translation of protein from the RNA, splicing of the RNA to yield one or more mRNA species, and catalytic activity that may be imparted or facilitated by the RNA. The effect of such interference with target nucleic acid function may provide the ability to modulate the expression of particular gene products.

In yet a further embodiment, the invention provides plant cells, plant embryos, plant tissues, whole plants and seeds that have been transformed with at least one plant gene expression cassette of the present invention.

The above-mentioned and additional features of the present invention are further illustrated in the Detailed Description contained herein. All references disclosed herein, including U.S. patents, are hereby incorporated by reference in their entirety as if each was incorporated individually.

DESCRIPTION OF THE FIGURES

FIG. 6: Sequences of wild type Box II (labeled Box II) and two non-limiting examples of its operational derivatives (labeled as Box IIm1 and Box IIm2). The mutated nucleotides in each operational derivative are identified in bold underline.

FIG. 8: Comparative analysis of DNA binding affinities of RF2a and RF2b.

FIG. 12: Primers used in generating the chimeric promoters containing the Box II element and portions of the CaMV 35S promoter, which are illustrated in FIG. 11. To facilitate the cloning process, a HindIII restriction site was added to the 5' end of the primers (underlined). Box II elements are shown in bold and upper case letters. The sequences from the CaMV 35S promoter are shown in lower case italic letters.

FIG. 14: A: Relative GUS activities of constructs in which the uidA gene was driven by Box II and CaMV 35S fusion promoters (which are illustrated in FIG. 11), wherein the constructs were inserted into BY-2 protoplasts that produce RF2a. B: Relative GUS activities of the constructs referenced in (A) above, wherein the constructs were inserted into BY-2 protoplasts that produce RF2a and RF2b. The GUS activity of each sample was normalized against the GFP internal control.

FIG. 24: A: Diagram of the different constructs used to transform BY-2 protoplasts, as further described in Example 15. B: A bar graph showing the relative GUS activity produced by the various constructs transformed into such BY-2 protoplasts, as further described in Example 15 below.

FIG. 27: A: Diagram of the different constructs used to transform BY-2 protoplasts, as further described in Example 17. B: A bar graph showing the relative GUS activity produced by the various constructs transformed into such BY-2 protoplasts, as further described in Example 17 below.

DESCRIPTION OF THE SEQUENCE LISTING

Figure 1:
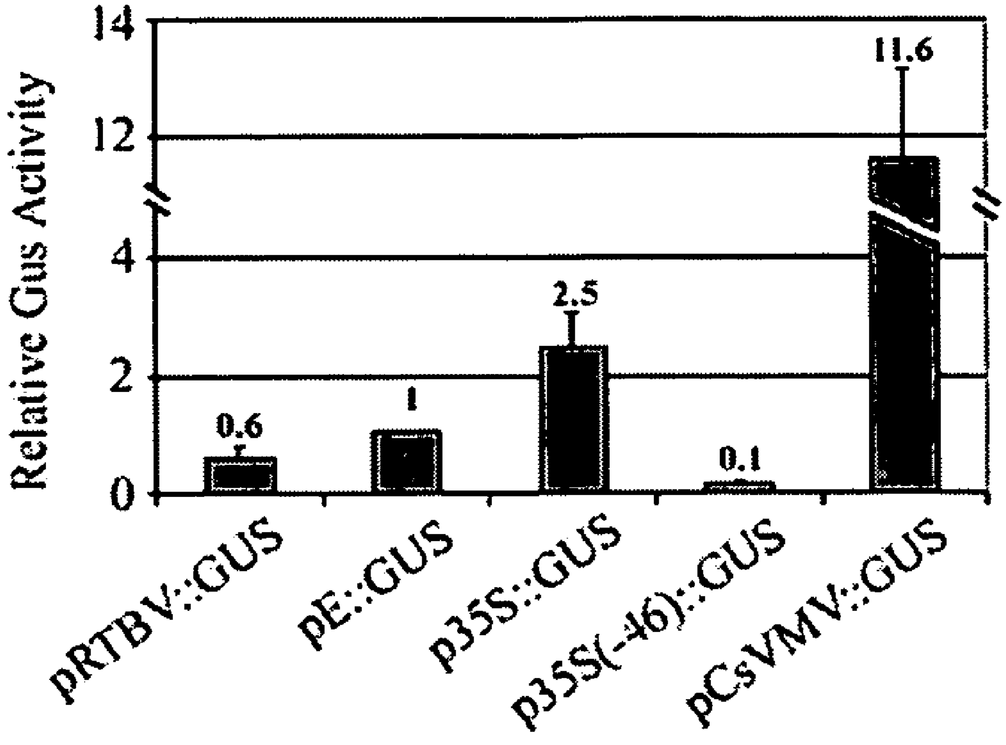
FIG. 1: Comparison of RTBV promoter activity with different constitutive promoters in BY-2 protoplasts. "RTBV" represents the promoter of RTBV; "E" represents the E fragment of the RTBV promoter; "35S" refers to the enhanced 35S promoter of CaMV; "35S(−46)" refers to the 5' deletion mutation of the CaMV 35S promoter, which ends at position −46 as described herein; "CsVMV" represents the promoter of CsVMV. The results presented are the mean value of three independent experiments with standard variations. Each experiment included three repeats and all data were normalized against GFP as internal control.

SEQ ID NO. 1: The nucleic acid sequence of the Box II element.

SEQ ID NO. 2: The nucleic acid sequence of the Box IIm1 element—an operational derivative of the Box II element.

SEQ ID NO. 3: The nucleic acid sequence of the Box IIm2 element—an operational derivative of the Box II element.

SEQ ID NO. 4: The amino acid sequence of the RF2a transcription factor.

SEQ ID NO. 5: The amino acid sequence of the RF2b transcription factor.

SEQ ID NO. 6: The amino acid sequence of the acidic domain of the RF2a transcription factor.

SEQ ID NO. 7: Non-limiting example of nucleic acid sequence that encodes the RF2a transcription factor.

SEQ ID NO. 8: Non-limiting example of nucleic acid sequence that encodes the RF2b transcription factor.

SEQ ID NO. 9: Non-limiting example of nucleic acid sequence that encodes the acidic domain of the RF2a transcription factor.

SEQ ID NO. 10: Primer sequence of BoxII-del-3'.

SEQ ID NO. 11: Primer sequence of BoxII-del-5'.

SEQ ID NO. 12: The nucleic acid sequence of the E fragment (promoter) of the RTBV promoter sequence.

SEQ ID NO. 13-35: Primer sequences referenced in Table 1/Example 2.

SEQ ID NO. 36: The GUS 3' primer.

SEQ ID NO. 37-42: Primer sequences referenced in Table 2/Example 6.

SEQ ID NO. 43: Control primer 1.5h-53CaMV-c.

SEQ ID NO. 44: Control primer −3.5h-74CaMV-c.

SEQ ID NO. 45: Control primer −5.5h-95CaMV-c.

SEQ ID NO. 46-52: Primer sequences referenced in Table 3/Example 8.

SEQ ID NO. 53: Primer sequence of BII-48Ca 5'.

SEQ ID NO. 54: The amino acid sequence of the proline-rich domain of the RF2a transcription factor.

SEQ ID NO. 55: The amino acid sequence of the glutamine-rich domain of the RF2a transcription factor.

SEQ ID NO. 56-61: Primer sequences referenced in Table 4/Example 10.

SEQ ID NO. 62: Nucleic acid sequence of the RTBV promoter.

SEQ ID NO. 63: Nucleic acid sequence of the E fragment containing the Box IIm1 element.

SEQ ID NO. 64: Nucleic acid sequence of the E fragment containing the Box IIm2 element.

SEQ ID NO. 65: Nucleic acid sequence of E(ΔBox II) fragment.

SEQ ID NO. 66: Nucleic acid sequence of the CaMV 35S minimal (1-108) promoter.

SEQ ID NO. 67: Nucleic acid sequence of the CsVMV promoter.

SEQ ID NO. 68: Amino acid sequence of RF2a-ΔP.

SEQ ID NO. 69: Amino acid sequence of RF2a-ΔQ.

SEQ ID NO. 70: Amino acid sequence of RF2a-ΔPΔA.

SEQ ID NO. 71: Amino acid sequence of RF2a-ΔPΔQ.

SEQ ID NO. 72: Amino acid sequence of RF2a-3Δ.

SEQ ID NO. 73: "R"—Reverse Primer sequence.

SEQ ID NO. 74: Nucleic acid sequence of the 2C7 cis element (i.e., the domain to which the 2C7 zinc finger protein binds).

SEQ ID NO. 75: Amino acid sequence of the synthetic 2C7 domain.

SEQ ID NO. 76: Nucleic acid sequence used to express the 2C7 domain (SEQ ID NO. 75).

SEQ ID NO. 77-83: DNA cis elements referenced in Table 5/Example 12.

SEQ ID NO. 84-91: DNA binding domains and related cis elements referenced in Table 6/Example 12.

SEQ ID NO. 92: Nucleic acid sequence of chimeric promoter with Gal4 DNA binding sites and CaMV 35S minimal promoter.

SEQ ID NO. 93: Nucleic acid coding sequence of VGE.

SEQ ID NO. 94: Primer A-2C7 5'.

SEQ ID NO. 95: Primer A-2C7 3'.

SEQ ID NO. 96: Primer A68-2C7 5'.

SEQ ID NO. 97: Primer A96-2C7 3'.

SEQ ID NO. 98: Primer used to amplify the 35S-56/84-2C7 construct described in Example 15.

SEQ ID NO. 99: Primer used to amplify the 35S-56/84-2C7 construct described in Example 15.

SEQ ID NO. 100: Amino acid sequence of the chimeric VGE receptor.

SEQ ID NO. 101: Amino acid sequence of "A5" minimal acidic domain of RF2a, described in Example 17.

SEQ ID NO. 102: Nucleic acid sequence encoding the "A5" minimal acidic domain of RF2a, described in Example 17.

SEQ ID NO. 103: Amino acid sequence of GE domain (of VGE receptor).

SEQ ID NO. 104: Nucleic acid sequence encoding the GE domain.

SEQ ID NO. 105: Amino acid sequence of E domain (of VGE receptor).

SEQ ID NO. 106: Nucleic acid sequence encoding the E domain.

SEQ ID NO. 107: Amino acid sequence of G domain (of VGE receptor).

SEQ ID NO. 108: Nucleic acid sequence of 5XG (a Gal4 binding domain)—the sequence recognized by the G domain of the VGE receptor.

DETAILED DESCRIPTION OF THE INVENTION

The following will describe in detail several preferred embodiments of the invention. These embodiments are provided by way of explanation only, and thus, should not unduly restrict the scope of the invention. In fact, those of ordinary skill in the art will appreciate upon reading the present specification and viewing the present drawings that many variations and modifications of the invention may be employed, used and made without departing from the scope and spirit of the invention.

The present invention can be viewed as having at least two components. The first of the at least two components relates to the Box II element; operational derivatives of the Box II element; chimeric promoters containing one or more of these elements; plant gene expression cassettes containing at least one chimeric promoter of the present invention; plant cells, embryos and tissues transformed with at least one expression cassette of the present invention and methods of using the foregoing compositions in connection with RF2a and/or RF2b to regulate the expression of at least one gene of interest. The second of the at least two components relates to (i) novel transcription factors that comprise at least one DNA-binding domain and an amino acid sequence that is at least substantially similar to the acidic domain of RF2a and (ii) methods of using the novel transcription factors to regulate the expression of at least one gene of interest.

Novel Chimeric Promoters

In one preferred embodiment, the invention provides novel chimeric promoters. The promoters of the present invention comprise a first nucleic acid sequence derived from any promoter (other than the RTBV promoter (SEQ ID NO:62)), or promoter fragment, that is capable of driving gene expression in plant cells. The promoters further comprise at least one nucleic acid sequence selected from the group consisting of: (i) the Box II element (SEQ ID NO:1); (ii) the Box IIm1 element (SEQ ID NO:2); (iii) the Box IIm2 element (SEQ ID NO:3); (iv) sequences that are substantially similar to either SEQ ID NO:1, 2 or 3, or (v) other operational derivatives of the Box II element. As used herein, the term "operational derivative" shall refer, generally, to the Box IIm1 element, the Box IIm2 element, sequences that are substantially similar to the Box II, Box IIm1 or Box IIm2 element and other nucleic acid sequences that are capable of interacting with RF2a and/or RF2b to regulate gene expression.

It will be understood by those skilled in the art that two nucleic acid sequences are "substantially similar" when approximately 70% or more (preferably at least about 80%, and most preferably at least about 90% or 95%) of the nucleotides match over the defined length of the nucleic acid sequence. Sequences that are substantially homologous can be identified by comparing the sequences using readily accessible computer software, or in a Southern hybridization experiment under, for example, stringent conditions as defined for that particular system. Defining appropriate hybridization conditions for a particular system is within the skill of the art. It will be further understood by those skilled in the art that the phrase "at least substantially similar" refers to sequences that are "substantially similar" as described above or, alternatively, identical to one another.

As used herein, "substantially similar" is further meant to include a nucleic acid sequence which, by virtue of the degeneracy of the genetic code, is not identical with that shown in any of the sequences shown in the Sequence Listing, but which still encodes the same amino acid sequence; or a modified nucleic acid sequence that encodes a different amino acid sequence that retains substantially the same activities of the original proteins, either because one amino acid is replaced with a similar amino acid, or because the change (whether it be substitution, deletion or insertion) does not affect the active site of the protein. Thus, it is contemplated by the inventors that various changes may be made in the nucleic acid sequences disclosed, and, of course, the encoded polypeptides, without appreciable loss of their biological activity or utility in the present invention.

The chimeric promoters of the present invention are, preferably, constructed by combining the first nucleic acid sequence derived from any plant functional promoter, or promoter fragment, with at least one nucleic acid sequence selected from the group consisting of SEQ ID NO:1, 2, 3 and sequences substantially similar to SEQ ID NO:1, 2 or 3. More preferably, however, the chimeric promoters of the present invention are constructed by combining the first nucleic acid sequence derived from any plant functional promoter, or promoter fragment, with at least one nucleic acid sequence selected from the group consisting of SEQ ID NO:1, 2 and 3. The term "chimeric promoter," as used herein, refers to any plant functional promoter sequence, or promoter fragment, that comprises SEQ ID NO:1, 2, 3, or sequences substantially similar thereto, wherein such plant functional promoter sequence is not derived from the RTBV promoter.

The nucleic acid sequences consisting of SEQ ID NO:1, 2, 3, and sequences substantially similar thereto, may be positioned within the first nucleic acid sequence described above, which comprises any plant functional promoter (or promoter fragment). Alternatively, the nucleic acid sequences consisting of SEQ ID NO:1, 2, 3, and sequences that are substantially similar to SEQ ID NO:1, 2 or 3, may be fused to the 5' or 3' end of such plant functional promoter (or promoter fragment).

Although SEQ ID NO:1, 2, 3, and sequences substantially similar thereto, may be positioned within, or fused to the end of, a chimeric promoter, such sequences are, preferably, positioned in specific locations of the DNA helix. In particular, such nucleic acid sequences are, preferably, operably linked to the 5' end of the selected promoter, or promoter fragment, with a space of approximately 7 nucleotides from the TATA box plus one or more full "turns of DNA helix." It is well-known in the art that one turn of DNA helix equals, approximately, 10.4 base pairs. Furthermore, the TATA box, which, generally, is the module within a promoter that functions to position the start site for RNA synthesis, and its location in a promoter can be easily identified by those skilled in the art. In many cases, the TATA box consensus sequence (TATAAT) is 20 to 30 base pairs upstream (i.e., 5') of the transcription start site (by convention −30 to −20 base pairs relative to the transcription start site).

The Box II element and its operational derivatives may be used in connection with a variety of promoters, or promoter fragments, to create novel chimeric promoters. Preferably, however, the Box II element and/or its operational derivatives are operably linked to a promoter, or promoter fragment, that comprises a transcription initiation domain. The term "transcription initiation domain" refers to a sequence having at least an RNA polymerase binding site and an mRNA initiation site.

Such basic guidelines for promoter, or promoter fragment, selection emphasize the notion that the Box II element and its operational derivatives are, indeed, "portable" and can be transferred to a plurality of promoter sequences. Of course, the promoter sequence with which the Box II element and/or its operational derivatives will be used, preferably, relates to the target cell-type in which gene expression is desired.

For example, some promoters are known to be active in particular cell-types, in certain tissues, under certain abiotic conditions and/or in the presence of certain inducible agents. Thus, the cell-type and/or conditions in which gene expression is desired will impact the identity of the promoter sequence with which Box II and/or its operational derivatives will be used. Although the endogenous promoter of the gene of interest may be utilized herein for transcriptional regulation, preferably, the promoter is a foreign regulatory sequence. For plant expression vectors, suitable viral promoters include, for example, the RTBV promoter; the 35S RNA and 19S RNA promoters of the cauliflower mosaic virus ("CaMV"); the full-length transcript promoter from figwort mosaic virus ("FMV"); and the cassava vein mosaic virus ("CsVMV") promoter.

The Box II element, of course, can be isolated from natural sources, e.g., the Box II element can be isolated from the E fragment of the RTBV promoter (SEQ ID NO:62) using techniques well-known in the art. More preferably, however, the Box II element and its operational derivates are synthesized using standard DNA synthesis techniques (see, for example, Current Protocols in Molecular Biology, Unit 2.11, eds. Ausubel, et al., John Wiley & Sons, 1995).

Expression Cassettes Comprising Novel Chimeric Promoters

The present invention further provides plant gene expression cassettes that comprise a first chimeric promoter of the present invention operatively linked to one or more genes of interest. The expression cassettes may further comprise a second promoter operatively linked to a nucleic acid sequence that encodes a polypeptide, which comprises an amino acid sequence selected from the group consisting of: (a) SEQ ID NO:4; (b) SEQ ID NO:5; (c) SEQ ID NO:6 and (d) sequences that are substantially similar to either SEQ ID NO:4, 5 or 6. Non-limiting examples of nucleic acid sequences that encode the amino acid sequences set forth in SEQ ID NO:4, SEQ ID NO:5 and SEQ ID NO:6 are shown in SEQ ID NO:7, SEQ ID NO:8 and SEQ ID NO:9, respectively.

The one or more genes of interest operatively linked to a first chimeric promoter of the present invention, when including an open reading frame ("ORF"), may encode a protein. Of course, the gene of interest can be an endogenous or exogenous sequence. In addition, the ORF may include certain 5' and 3' untranslated sequences. Still further, appropriate transcription termination and polyadenylation sequences may, preferably, be included.

Genes of interest, the expression of which may be regulated according to the present invention, may include, for example, sequences that naturally exist in plants, animals, bacteria, viruses or fungi; synthetic DNA sequences that encode a specific RNA or protein product; cDNA sequences derived from mRNA; DNA sequences modified by mutagenesis, for example, through site specific mutagenesis; chimeras of any of the above (to produce fusion proteins); and DNA sequences encoding complementary RNA molecules (for "antisense" applications); and combinations and/or fragments of the above.

Examples of proteins that can be encoded by the gene of interest include, but are not limited to, nutritionally important proteins; growth promoting factors; proteins for early flowering in plants; proteins that impart protection to the plant under certain environmental conditions, e.g., proteins conferring resistance to metals or other toxic substances, such as herbicides or pesticides; stress related proteins that confer tolerance to temperature or hydration extremes; proteins conferring resistance to fungi, bacteria, viruses, insects and nematodes; and proteins of specific commercial value, e.g., enzymes involved in metabolic pathways, proteins having therapeutic activity in humans, and others.

The term "operably linked," as used herein, refers to the functional linkage between, for example, the Box II element and/or its operational derivatives and a plant functional promoter or promoter fragment; between a promoter sequence, including the novel chimeric promoters of the present invention, and any gene of interest; and between a promoter sequence and any sequence encoding the RF2a protein, RF2b protein, a protein comprising the acidic domain of RF2a and/or any protein that is substantially similar to the foregoing proteins.

The second promoter operatively linked to a nucleic acid sequence that encodes a polypeptide, which comprises an amino acid sequence selected from the group consisting of: (a) SEQ ID NO:4; (b) SEQ ID NO:5; (c) SEQ ID NO:6; and (d) sequences that are substantially similar to either SEQ ID NO:4, 5, or 6, may constitute any promoter that is capable of driving gene expression in the target plant cells. As described above, certain promoters are known to be active in particular cell-types, in certain tissues, under certain abiotic conditions and/or in the presence of certain inducible agents. Thus, the cell-type and/or conditions in which gene expression is desired will impact the identity of the promoter that is selected to drive expression of sequences encoding RF2a, RF2b, polypeptides comprising the acidic domain of RF2a or polypeptides that are substantially similar to any of the foregoing. Of course, such promoters may include both constitutive, e.g., the CaMV promoter, and inducible promoters.

By placing the nucleic acid sequence encoding RF2a, RF2b, polypeptides comprising the acidic domain of RF2a or polypeptides that are substantially similar to any of the foregoing, under the control of a chemically-inducible promoter, the gene expression system can be activated at will. The use of inducible promoters in this capacity provides control over the effect that the encoded proteins may have on the expression of promoter sequences (and genes operatively linked to such sequences) comprising the Box II element and/or its operational derivatives. In short, expression of the nucleic acid sequence to which the second promoter is operatively linked is stimulated and/or enhanced by applying an effective amount of the chemical inducer to the plant cells, embryos or tissues that have been transformed with the appropriate expression cassette of the present invention. Application of the inducer, therefore, allows the expressed transcription factor to interact with, and stimulate (or enhance) the expression of, the chimeric promoter and the one or more genes of interest to which it is operatively linked.

To be most useful, an inducible promoter should 1) provide low expression in the absence of the inducer; 2) provide high expression in the presence of the inducer; 3) employ an induction scheme that does not interfere with the normal physiology of the plant; and 4) has no effect on the expression of other genes. Examples of inducible expression schemes useful in plants include those induced by chemical means, such as the ecdysone agonist-inducible gene expression systems (Christopherson et al., 1992; Martinez et al., 1999). The ecdysone agonist-inducible gene expression systems, preferably, employ commercially-available non-steroidal ecdysone agonists, such as tebufenozide and methoxyfenozide.

Additional examples of inducible promoters useful in plants include, but are not limited to, promoters that respond to tetracycline (Gatz et al., 1992; Weinmann et al., 1994); the yeast metallothionein promoter, which is activated by copper ions; the In2-1 and In2-2 regulator sequences, which are activated by substituted benzenesulfonamides, e.g., herbicide safeners; and GRE regulatory sequences, which are induced by glucocorticoids. In addition, plant promoters such as the light-inducible promoter from the small subunit of ribulose bis-phosphate carboxylase (ssRUBISCO); mannopine synthase promoter; nopaline synthase ("NOS") and octopine synthase ("OCS") promoters (carried on tumor-inducing plasmids of *Agrobacterium tumefaciens*) or heat shock promoters, e.g., soybean hsp17.5-E or hsp17.3-B, may be used. Other promoters, both constitutive and inducible, will be known to those of skill in the art.

It will be appreciated by those skilled in the art that the first chimeric promoter, which is operatively linked to at least one gene of interest, and the second promoter, which is operatively linked to a sequence encoding RF2a, RF2b, polypeptides comprising the acidic domain of RF2a or polypeptides that are substantially similar to any of the foregoing, may exist in a single gene expression cassette (or vector), or, alternatively, in separate cassettes (or vectors). Still further, those skilled in the art will appreciate that an expression cassette may comprise a single chimeric promoter, or, alternatively, a plurality of chimeric promoters, each operatively linked to at least one gene of interest. Moreover, the plurality of chimeric promoters may be substantially similar in sequence, or, alternatively, may comprise significantly different sequences.

Novel Transcription Factors

Over the years, several classes of DNA-binding proteins have been characterized and the nucleic acid sequences with which such proteins interact identified. For example, zinc finger proteins represent a class of motifs that are known to be involved in the sequence-specific recognition of DNA. As the name implies, this DNA-binding domain is folded around a zinc ion. To date, more than two hundred proteins, many of them transcription factors, have been shown to possess zinc finger domains. In general, zinc fingers connect transcription factors to their target locations by binding to specific DNA sequences.

The RF2a and RF2b transcription factors described herein represent yet another class of DNA-binding proteins. Specifically, RF2a and RF2b are representative examples of what are commonly referred to as bZIP transcription factors. The bZIP transcription factors are generally characterized by a bipartite DNA-binding domain consisting of a basic region involved in sequence-specific binding, and a leucine zipper region required for dimerization. The bZIP domain of RF2a shares high similarity with bZIP proteins that exist naturally in plants such as *Arabidopsis*, tobacco, tomato, and other plants (Fukazawa et at, 2000; Jakoby et al., 2002; Ringli and Keller, 1998). In particular, this group of proteins is known to have a lysine residue at the −10 position relative to the first leucine residue of the leucine zipper region (Yin et al., 1997). The amino acid sequence signature of the DNA-binding regions of this class of proteins is NXXXSAXXXSK (Fujii et al., 2000) (SEQ ID NO: 109).

The present invention provides novel transcription factors, and uses thereof, which provide the ability to regulate the expression of at least one gene of interest. In particular, the inventors have discovered that the acidic domain of RF2a (SEQ ID NO:6), and amino acid sequences substantially similar to SEQ ID NO:6, can be fused to unrelated transcription factors, or transcription factor-like complexes, to regulate gene expression. In certain embodiments, the invention provides that novel transcription factors, which comprise the acidic domain of RF2a and at least one DNA-binding domain, can be used to modulate the expression of one or more genes driven by promoters that comprise nucleic acid sequences recognized by such DNA-binding domain of the novel transcription factors.

In certain embodiments, the acidic domain of RF2a (SEQ ID NO:6), and/or amino acid sequences substantially similar to SEQ ID NO:6, can be fused to any class of DNA-binding domains (and/or unrelated transcription factors comprising such domains). The acidic domain of RF2a, and/or substantially similar sequences, can be fused, for example, to any polypeptide comprising a leucine zipper, bZIP domain, zinc-finger, homeobox, basic helix-loop-helix domain, or other DNA-binding domains currently known in the art (or discovered hereafter). It should be appreciated, however, that the DNA-binding domain selected (or the polypeptide comprising such domain) must be capable of interacting with the promoter operatively linked to the gene of interest for which control of expression is desired.

It will be appreciated by those skilled in the art that two amino acid sequences are "substantially similar" when approximately 70% or more (preferably at least about 80%, and more preferably at least about 90% or 95%) of the amino acids match over the defined length of the sequences. The term "substantially similar" is further meant to refer to amino acid sequences that have been modified from an original sequence, wherein the modified amino acid sequence retains substantially the same level of activity as the original amino acid sequence. This retention in activity, of course, may occur when one or more amino acids are replaced with similar amino acids, or because the change (whether it be substitution, deletion or insertion) does not affect the active site of the protein. Thus, it is contemplated by the inventors that various changes may be made to the acidic domain of RF2a, without appreciable loss of its biological activity and utility in the present invention. It will be further understood by those skilled in the art that the phrase "at least substantially similar" as it is used herein with respect to amino acid sequences refers to sequences that are "substantially similar" as described above or, alternatively, identical to one another.

In certain embodiments, for example, novel transcription factors are provided, which comprise a fragment of the acidic domain of RF2a (SEQ ID NO:6). More particularly, the present invention contemplates that internal regions and fragments of the acidic domain of RF2a (SEQ ID NO:6) may be used to form novel transcription factors, which are capable of regulating gene expression as described herein.

As used herein, "fragments of the acidic domain" and "fragment of the acidic domain" refer to amino acid sequences comprising less than all of the amino acid residues of SEQ ID NO:6, wherein such amino acid sequence is substantially similar to the corresponding region of the full-length SEQ ID NO:6. More particularly, for example, a "fragment of the acidic domain" includes an amino acid sequence encompassing at least 30%, 40%, 50%, 60%, 70%, 80%, or 90% of SEQ ID NO:6, wherein such amino acid sequence is substantially similar to the corresponding region of the full-length SEQ ID NO:6.

While the acidic domain of RF2a (SEQ ID NO:6) (and/or amino acid sequences substantially similar to SEQ ID NO:6) and fragments of the acidic domain may be fused to any class of DNA-binding domains (and/or unrelated transcription factors comprising such domains) to create novel transcription factors as described herein, the invention provides that such sequences may act in the absence of DNA-binding domains to regulate gene expression. In such embodiment, the acidic domain of RF2a may be used alone or in connection with other regulatory proteins or domains to modulate gene expression. For example, the invention provides novel transcription factors that comprise the acidic domain of RF2a and any other amino acid sequence not derived from RF2a or RF2b, which are capable of regulating the expression of at least one gene of interest. The numerous mechanisms by which such transcription factors may regulate expression are well-known to those skilled in the art, which include, for example, affecting the formation of the transcription initiation complex and recruiting other regulatory proteins to the transcription initiation region.

Expression Cassettes Encoding Novel Transcription Factors

The present invention further provides plant gene expression cassettes comprising (i) a first promoter, which comprises a nucleic acid sequence that is capable of interacting with at least one DNA-binding domain of at least one polypeptide, operatively linked to a gene of interest and (ii) a second promoter operatively linked to a nucleic acid sequence that encodes a polypeptide, which comprises an amino acid sequence that is at least substantially similar to SEQ ID NO:6 and a DNA-binding domain that is capable of interacting with the corresponding nucleic acid sequence of the first promoter.

Of course, in light of the foregoing, nucleic acid sequences encoding the acidic domain of RF2a, and/or substantially similar amino acid sequences, may be operatively linked to, for example, nucleic acid sequences that encode polypeptides comprising any motif known to interact with the first promoter (or, more specifically, elements contained within or near the first promoter), which is operatively linked to the one or more genes of interest. This interaction will, preferably, initiate and/or enhance the expression of the one or more genes of interest. An example of a nucleic acid sequence that encodes the acidic domain of RF2a (SEQ ID NO:6) includes, but is not limited to, the sequence shown in SEQ ID NO:9.

Examples of nucleic acid sequences encoding DNA-binding domains that can be used in this capacity include, but are not limited to, sequences encoding a leucine zipper, the bZIP domain, the zinc-finger, the homeobox, the basic helix-loop-helix domain or others. It will be appreciated by those skilled in the art that the selected DNA-binding domain must be capable of interacting with the promoter operatively linked to the one or more genes of interest for which control of expression is desired. Still further, it will be appreciated by those skilled in the art that sequences encoding the acidic domain of RF2a, for example, and at least one DNA-binding domain may be tethered directly to one another, or, alternatively, may be connected indirectly through intervening sequences, e.g., spacers, other polypeptide-encoding sequences, etc.

In certain alternative embodiments, the second promoter is operatively linked to a nucleic acid sequence that encodes a novel transcription factor, which comprises an amino acid sequence that is at least substantially similar to SEQ ID NO:6 and is capable of modulating the expression level of the nucleic acid sequence operatively linked to the first promoter through means other than direct DNA binding or interaction. As described above, such transcription factors may be used to regulate the expression level of one or more genes of interest by, for example, affecting the formation of the transcription initiation complex or recruiting other regulatory proteins to the transcription initiation region.

Any promoter, or promoter fragment, capable of driving gene expression in plant cells may be operatively linked to sequences encoding the novel transcription factors of the present invention. The promoter selected for any given system or application may confer constitutive expression in the transformed plant cell, or, alternatively, inducible expression. Furthermore, as described above with respect to other embodiments, certain promoters are known to be active in particular cell-types, in certain tissues and/or under certain abiotic conditions. Thus, the cell-type and/or conditions in which gene expression is desired will impact the identity of the promoter selected to drive expression of sequences encoding the novel transcription factors of the present invention.

Thus, in one embodiment, the nucleic acid sequences encoding the novel transcription factors of the present invention may be placed under the control of chemically-inducible promoters. In this embodiment, the gene expression system may be activated at will, which provides control over the effect that the encoded novel transcription factors may have on the expression of promoter sequences (and genes operatively linked to such sequences) that comprise the element to which the expressed DNA-binding domain, for example, is capable of interacting. As described above with respect to other embodiments, several inducible promoters well-known in the art could be used in this capacity to drive the expression of novel transcription factors.

It will be appreciated by those skilled in the art that the first promoter, which is operatively linked to at least one gene of interest, and the second promoter, which is operatively linked to a sequence encoding a novel transcription factor of the present invention, may exist in a single gene expression cassette (or vector), or, alternatively, in separate cassettes (or vectors). Still further, those skilled in the art will appreciate that a single promoter, or, alternatively, a plurality of promoters, each operatively linked to at least one gene of interest, may contain a sequence and/or element capable of interacting with the encoded novel transcription factors. Moreover, the plurality of promoters can be substantially similar in sequence, or, alternatively, may comprise significantly different promoter sequences.

Methods of Regulating Gene Expression

The invention further provides methods of regulating the expression level of at least one gene of interest, which comprise transforming a plant cell with at least one plant gene expression cassette of the present invention. Still further, the invention provides methods of regulating the expression level of at least one gene of interest, which comprise (a) constructing at least one plant gene expression cassette of the present invention; (b) transforming a plant cell with the plant gene expression cassette of the present invention; and (c) regenerating whole plants from the transformed plant cell. In a related embodiment, for plants, plant tissues or plant cells that have been transformed with a gene expression cassette comprising a chemically-inducible promoter operatively linked to a nucleic acid sequence that encodes a polypeptide comprising an amino acid sequence that is at least substantially similar to SEQ ID NO:4, 5 or 6, the method further comprises contacting the transformed plants, plant tissues or plant cells, directly or indirectly, with an activating amount of the expression-inducing chemical.

In other embodiments, plant gene expression cassettes comprising two or more chimeric promoters of the present invention, which are operatively linked to one or more genes of interest, can be transformed into a plant cell in connection with, for example, RF2a- and/or RF2B-encoding sequences to achieve a "cascade-type" system. In such embodiments, the expression of RF2a and/or RF2b activates and/or enhances the expression of the nucleic acid sequences to which the two or more chimeric promoters are operatively linked. Still further, the nucleic acid sequences encoding the RF2a and/or RF2b proteins, for example, may be operably linked to chemically-inducible promoters. In such case, upon contacting plants, plant tissues or plant cells, which have been transformed with such sequences, with the expression-inducing chemical, the RF2a and/or RF2b transcription factors are produced. The RF2a and/or RF2b transcription factors subsequently interact with the Box II elements (and/or operational derivatives of Box II) to regulate gene expression. This interaction, of course, results in the synchronized activation and/or enhancement of expression of all Box II-dependent genes (or all genes operatively linked to promoters containing operational derivatives of Box II).

In other embodiments, plant gene expression cassettes comprising at least one chimeric promoter of the present invention, which is operatively linked to one or more genes of interest, can be transformed into plant cells in connection with RF2a- and/or RF2b-encoding sequences to "turn-off" or modulate the expression of one or more unrelated endogenous and/or exogenous genes. The foregoing expression cassettes can be used, for example, to activate and/or enhance the expression of the one or more genes of interest that encode molecules that selectively hybridize to specific target nucleic acid sequences, e.g., endogenous and/or exogenous genes. The hybridization of an oligomeric compound, for example, with its target nucleic acid sequence can have the effect of interfering with the normal function of the target sequence (this effect is generally referred to as "antisense"). The functions of DNA that can be affected in this embodiment, for example, include replication and transcription. The functions of RNA that can be affected include all vital functions such as translocation of the RNA to the site of protein translation, translation of protein from the RNA, splicing of the RNA to yield one or more mRNA species, and catalytic activity that may be imparted or facilitated by the RNA. The effect of such interference with target nucleic acid function provides the ability to modulate the expression of particular gene products.

The transformation of plant cells in accordance with the present invention may be carried out in essentially any of the various ways known to those skilled in the art of plant molecular biology. That is, the method employed for transformation. of target plant cells is not relevant to the present invention and any method suitable for the target plant cell-type may be utilized. As used herein, the term "transformation" refers to the alteration of the genotype of a host plant, including within plant cells, embryos and tissues, by the introduction of exogenous or endogenous nucleic acid sequences. Further, the terms "transfection" and "transformation," as used herein, may be used interchangeably, wherein the meaning accorded to both terms is, generally, as described above with respect to "transformation."

Neither is the plant species to which the methods and compositions of the present invention relate particularly germane to the invention. For example, dicotyledonous and monocotyledonous plants can be transformed. Thus, the various embodiments of the present invention may be applied to any plant, plant tissue, seed or plant cell for which transformation techniques are, or become, available.

In general, to commence a transformation process in accordance with the present invention, it is first necessary to construct a suitable vector and properly introduce the vector into a plant cell. The details of the construction of vectors utilized herein are known to those skilled in the art of plant molecular biology. As described above, one or more plant gene expression cassettes may be constructed to practice the methods, and to generate the plants, plant tissues and plant cells of, the present invention. In practice, the construct or constructs comprising the expression cassettes of the present invention will be inserted into a plant cell by transformation.

For example, constructs that include chimeric promoters of the present invention, which comprise the Box II element and/or its operational derivatives, can be introduced into plant cells using Ti plasmids, root-inducing (Ri) plasmids, and plant virus vectors. In the first instance, for example, the nucleic acid sequences of the present invention can be introduced into plant cells through *Agrobacterium*-mediated transformation. Methods involving the use of *Agrobacterium*-mediated transformation include, but are not limited to: 1) co-cultivation of *Agrobacterium* with cultured isolated protoplasts; 2) transforming (or infecting) plant cells or tissues with transformed *Agrobacterium* (as described herein); or 3) transformation of seeds, explants, apices or meristems with *Agrobacterium*. Under appropriate conditions known in the art, the transformed plant cells may be grown to form shoots, roots, and develop further into plants.

In some cases, it may be preferred to introduce the nucleic acid sequences of the present invention into plant cells utilizing *Agrobacterium tumefaciens* containing the Ti plasmid. When using an *A. tumefaciens* culture as a transformation vehicle, it is most advantageous to use a non-oncogenic strain of the *Agrobacterium* as the vector so that normal non-oncogenic differentiation of the transformed tissues is possible. It is also preferred that the *Agrobacterium* harbor a binary Ti plasmid system. Such a binary system comprises 1) a first Ti plasmid having a virulence region essential for the introduction of transfer DNA (T-DNA) into plants and 2) a chimeric plasmid. The chimeric plasmid contains at least one border region of the T-DNA region of a wild-type Ti plasmid flanking the nucleic acid sequence to be transferred. Binary Ti plasmid systems have been shown to be effective in transforming plant cells.

Alternatively, the nucleic acid sequences of the present invention can be introduced into plant cells using mechanical or chemical means. For example, nucleic acid sequences can be mechanically transferred by direct microinjection into plant cells utilizing micropipettes. Still further, the nucleic acid sequences may be transferred into plant cells using polyethylene glycol, which is capable of forming a precipitation complex with nucleic acid sequences that is taken up by target plant cells.

The nucleic acid sequences of the present invention can also be introduced into plant cells by electroporation. In this technique, plant protoplasts, for example, are electroporated in the presence of vectors or nucleic acid sequences to be transformed into the protoplasts. Electrical impulses of high field strength reversibly permeabilize plant membranes allowing the introduction of nucleic acids. Electroporated plant protoplasts reform the cell wall, divide and form a plant callus. Selection of the transformed plant cells with the transformed gene can be accomplished using, for example, phenotypic markers.

Another well-known method for introducing nucleic acid sequences of the present invention into plant cells is high velocity BIOLISTIC® penetration by small particles with the nucleic acid sequences to be introduced contained either within the matrix of small beads or particles, or on the surface thereof. See, for example, U.S. Pat. Nos. 5,932,479 and 5,693,507.

Additionally, DNA viruses may be used as vectors for introducing heterologous nucleic acid sequences into plant cells. See, for example, U.S. Pat. No. 4,407,956. Non-limiting examples of such DNA viruses include the Cauliflower mosaic virus ("CaMV") and the Geminivirus. The CaMV viral DNA genome, for example, may be inserted into a parent bacterial plasmid creating a recombinant DNA molecule which can be propagated in bacteria. After cloning, the recombinant plasmid may be re-cloned and further modified by introduction of the desired nucleic acid sequence of the present invention. The modified viral portion of the recombinant plasmid is then excised from the parent bacterial plasmid, and used to inoculate the target plant cells.

In any of the foregoing methods of transformation, a selectable marker may, optionally, be associated with constructs comprising nucleic acid sequences of the present invention. As used herein, "marker" refers to a gene that encodes a protein that confers a particular trait or a phenotype that permits the selection of, or the screening for, a plant or plant cell containing the marker. In some cases, the marker gene may encode a protein that confers antibiotic resistance to transformed plant cells, whereby the appropriate antibiotic can be used to select for transformed plant cells among cells that are not transformed. Examples of suitable selectable markers include adenosine deaminase, dihydrofolate reductase, hygromycin-B-phosphotransferase, thymidine kinase, xanthine-guanine phosphoribosyltransferase and amino-glycoside 3'-O-phosphotransferase II (kanamycin, neomycin and G418 resistance). Other suitable markers will be known to those of skill in the art. For example, screenable markers, such as the uidA gene, which encodes β-glucuronidase ("GUS"), luciferase or the gene encoding the green fluorescent protein ("GFP"), may also be used.

Plants and Plant Parts

Still further, the invention provides plant cells, plant embryos, plant tissues, whole plants and seeds that have been transformed with at least one plant gene expression cassette of the present invention. Methods of regenerating whole plants from transformed plant cells, embryos and tissues are well-known to those skilled in the art.

The following Examples are included to demonstrate certain embodiments of the invention. It should be appreciated by those skilled in the art that the techniques disclosed in the Examples that follow represent techniques discovered by the inventors to function well in the practice of the invention, and thus, can be considered to constitute preferred modes for its practice. However, those of ordinary skill in the art should, in light of the present disclosure, appreciate that many changes can be made in the specific embodiments that are disclosed and still obtain a like or similar result without departing from the spirit and scope of the invention.

EXAMPLES

Example 1

Analysis of the Box II Sequence in BY-2 Protoplasts

Until now, the behavior of the RTBV promoter in the tobacco BY-2 cell line and the contribution of its various cis elements to the promoter activity in BY-2 cells was unknown.

To compare the relative activity of the RTBV promoter with other constitutive promoters, tobacco BY-2 protoplasts were transfected with gene constructs in which the uidA open reading frame ("ORF") was driven by the enhanced cauliflower mosaic virus ("CaMV") 35S promoter, the enhanced CaMV promoter with a 5' deletion (at position −46 in relation to the transcription start site), the cassava vein mosaic virus ("CsVMV") promoter, the RTBV promoter or the E fragment of the RTBV promoter. The results are shown in FIG. 1, which indicate that the RTBV promoter and, more particularly, the E fragment of the RTBV promoter exhibit strong activity in BY-2 cells. Specifically, the E fragment exhibited more than one third of the activity that was observed with the CaMV 35S promoter, which is generally considered a strong promoter in plant cells.

Figure 2:
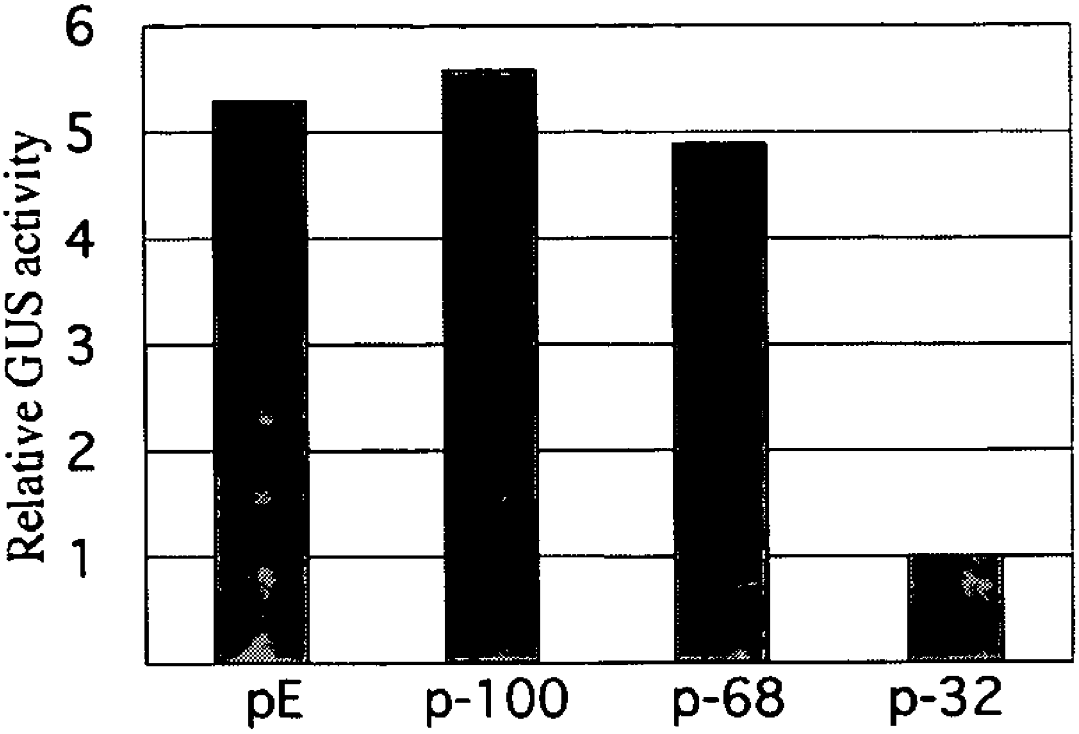
FIG. 2: Relative GUS activity of each plasmid driven by truncated mutants of the RTBV promoter. The results presented are the mean value of three independent experiments. Each experiment includes three repeats and all data were normalized against GFP as internal control.

To evaluate the functional contribution of different cis elements to the activity of the RTBV promoter, deletion mutants were generated from the E fragment by removing the GATA motif, ASL box and the Box II element at positions −100, −68 and −32, respectively. In FIG. 2, "pE" represents the entire E fragment; "p-100" represents a truncated E fragment at position −100, which excludes the GATA motif; "p-68" represents a truncated E fragment at position −68, which excludes the GATA motif and ASL box; and "p-32" represents a truncated E fragment at position −32, which excludes the GATA motif, ASL box and Box II element. All of the foregoing fragments included the TATA box and Box I element of the RTBV promoter.

The mutated promoters were then fused with the uidA gene. The GUS expression levels of the derived plasmids were determined in BY-2 protoplasts. The data in FIG. 2 show that the Box II element is crucial for promoter function in BY-2 protoplasts. As long as the Box II element was retained, the minimal promoter exhibited an expression level similar to that of the full E fragment. Once the Box II element was removed, however, the promoter activity decreased to less than 20% of the E fragment.

Example 2

The Optimal Position of the Box II Sequence

Figure 3:
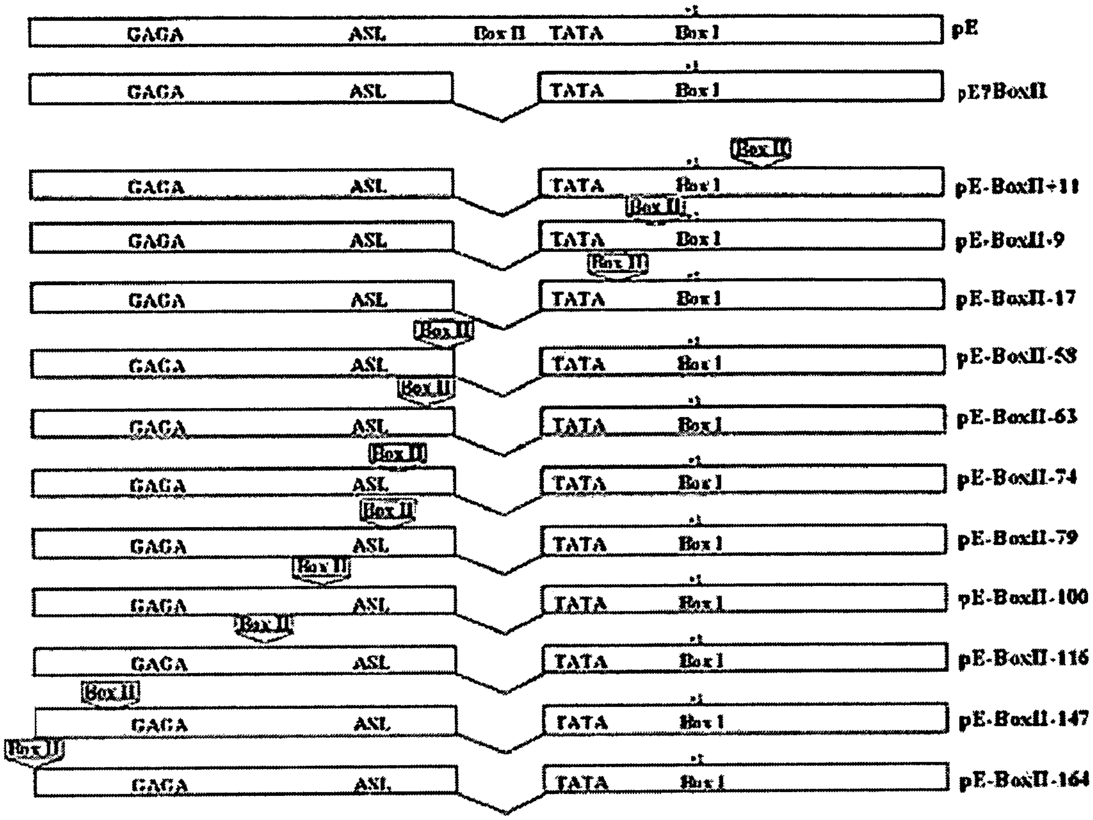
FIG. 3: Diagram of constructs that were prepared with the Box II element inserted into different locations in the context of the E fragment of the RTBV promoter. The modified promoters were then inserted into a vector, wherein the modified promoters were operatively linked to the uidA coding sequence and Nos terminator. The names of derived plasmids are shown to the right side of each diagram.

The optimal spacing of the Box II element, relative to the TATA box, for maximal effect on expression of the host promoter was determined. The original Box II sequence was deleted from the RTBV promoter in the context of the E fragment and re-inserted into the promoter at different locations, as indicated in FIG. 3. The mutated promoters were inserted into a cassette which contained the uidA coding sequence and Nos terminator. The derived plasmids are illustrated in FIG. 3.

Construction of Plasmids with Relocated Box II in the E promoter—To relocate the Box II element in the E promoter (fragment), the Box II element was first removed from the E promoter using fusion PCR strategy to generate E(ΔBox II). Next, the Box II element was re-introduced back into E(ΔBox II) (SEQ ID NO:65) at varied positions. In the first PCR reactions, two products were generated using the primer set R (SEQ ID NO:73)/BoxII-del-3' (SEQ ID NO:10) and BoxII-del-5' (SEQ ID NO:11)/GUS3' (SEQ ID NO:13) with pE:GUS as templates, wherein E represents the E fragment (SEQ ID NO:12) and GUS represents the uidA sequence, which is well-known in the art. The PCR products were gel purified and then used as templates for a second PCR reaction employing the R (SEQ ID NO:73)/GUS3' (SEQ ID NO:13) primer set.

The PCR product from the second reaction was restricted with HindIII/NcoI and cloned into pE:GUS to replace the E promoter with the same set of restriction sites. The resultant construct was named pE(ΔBoxII):GUS. The Box II element was re-introduced into pE(ΔBoxII):GUS using the same fusion PCR strategy as described above. To generate the E-Box II+11, E-Box II−9, E-Box II−17, E-Box II−58, E-Box II−63, E-Box II−74, E-Box II−79, E-Box II−100, E-Box II−116, E-Box II−147 and E-Box II−164 promoters, the first PCR reactions were carried out using the primer sets shown in the following Table 1:

TABLE 1

| Promoters | Primer Sets | Respective SEQ ID NOs. |
|---|---|---|
| E-Box II+11 | R/mtEBoxII(−0.5 h)-3' | SEQ ID NO: 73/14 |
| | mtEBoxII(−0.5 h)-5'/GUS3' | SEQ ID NO: 15/13 |
| E-Box II−9 | R/mtEBoxII(−1.0 h)-3' | SEQ ID NO: 73/16 |
| | mtEBoxII(−1.0 h)-5'/GUS3' | SEQ ID NO: 17/13 |
| E-Box II−17 | R/mtEBoxII(−2.0 h)-3' | SEQ ID NO: 73/18 |
| | mtEBoxII(−2.0 h)-5'/GUS3' | SEQ ID NO: 19/13 |
| E-Box II−58 | R/mtEBoxII(−2.5 h)-3' | SEQ ID NO: 73/20 |
| | mtEBoxII(−2.5 h)-5'/GUS3' | SEQ ID NO: 21/13 |
| E-Box II−63 | R/mtEBoxII(−4.5 h)-3' | SEQ ID NO: 73/22 |
| | mtEBoxII(−4.5 h)-5'/GUS3' | SEQ ID NO: 23/13 |
| E-Box II−74 | R/mtEBoxII(−6.0 h)-3' | SEQ ID NO: 73/24 |
| | mtEBoxII(−6.0 h)-5'/GUS3' | SEQ ID NO: 25/13 |
| E-Box II−79 | R/mtEBoxII(−9.0 h)-3' | SEQ ID NO: 73/26 |
| | mtEBoxII(−9.0 h)-5'/GUS3' | SEQ ID NO: 27/13 |
| E-Box II−100 | R/mtEBoxII(−111 nt)-3' | SEQ ID NO: 73/28 |
| | mtEBoxII(−111 nt)-5'/GUS3' | SEQ ID NO: 29/13 |
| E-Box II−116 | R/mtEBoxII(+2.0 h)-3' | SEQ ID NO: 73/30 |
| | mtEBoxII(+2.0 h)-5'/GUS3' | SEQ ID NO: 31/13 |
| E-Box II−147 | R/mtEBoxII(+29 nt)-3' | SEQ ID NO: 73/32 |
| | mtEBoxII(+29 nt)-5'/GUS3' | SEQ ID NO: 33/13 |
| E-Box II−164 | R/mtEBoxII(+6.0 h)-3' | SEQ ID NO: 73/34 |
| | mtEBoxII(+6.0 h)-5'/GUS3' | SEQ ID NO: 35/13 |

The PCR products generated in the first reaction were used as templates for the second PCR reaction using R/GUS3' as primers (SEQ ID NO:73/13). The PCR products from the second reactions were purified and cloned into the pE:GUS vector to replace the E promoter through the restriction sites HindIII/NcoI. The resultant plasmids were named pE-BoxII+11:GUS, pE-BoxII−9:GUS, pE-BoxII−17:GUS, pE-BoxII−58:GUS, pE-BoxII−63:GUS, pE-BoxII−74:GUS, pE-BoxII−79:GUS, pE-BoxII−100:GUS, pE-BoxII−116:GUS, pE-BoxII−147:GUS and pE-BoxII−164:GUS, respectively.

BY-2 protoplasts were transfected with the foregoing constructs and tested for GUS activity. Protein samples from such protoplasts were prepared using protein extraction buffer (Jefferson et al., 1987) and quantified using the DC protein assay kit (Bio-Rad Laboratories, Hercules, Calif.). Quantitative analysis of GUS activity was performed as described by Jefferson et al. (1987) using the substrate 4-methylum-belliferyl-β-D-glucuronide ("MUG") with the Spectra Max Gemini instrument (Molecular Devices Corp., Sunnyvale, Calif.).

Figure 4:
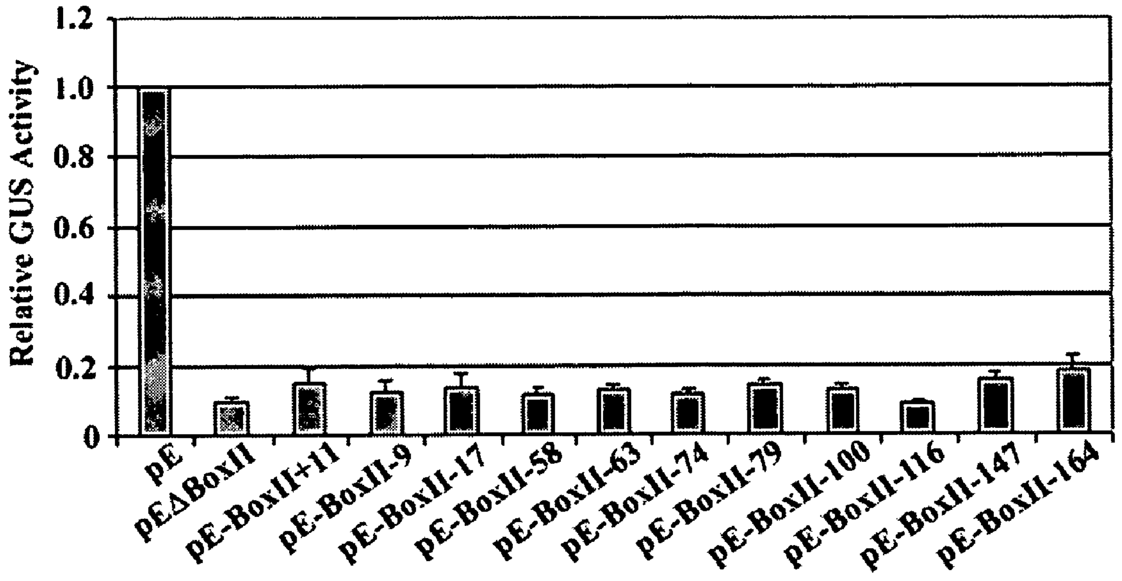
FIG. 4: Activities of the modified promoters shown in FIG. 3. The results presented are the mean value of three independent experiments with standard variation. Each experiment included three repeats and all data were normalized against GFP as internal control.

As shown in FIG. 4, the E promoter activity dramatically decreased when the Box II element was removed (see construct pEΔBoxII). Additionally, when the Box II element was removed and inserted in locations other than its native location, the mutated promoters exhibited similar activity as pEΔ-

BoxII, which indicates that the position of the Box II element in its native promoter is important.

Example 3

Effect of RF2a and RF2b on Expression of a Reporter Gene

Figure 5:
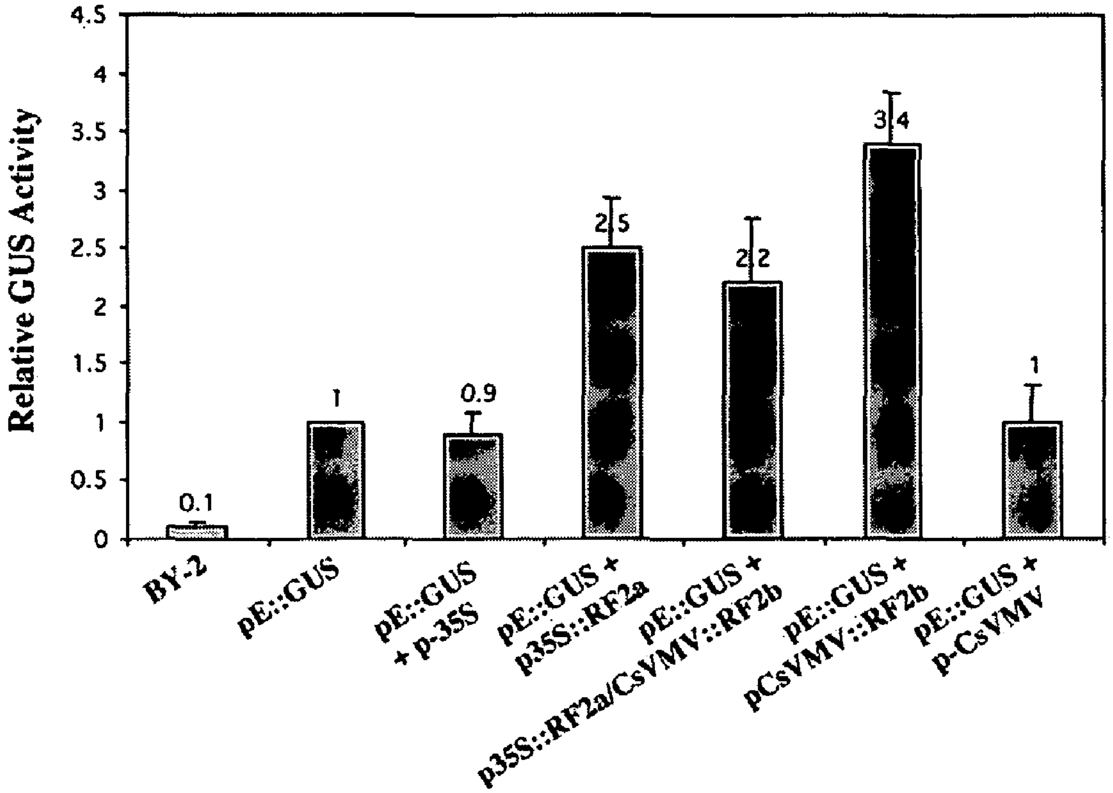
FIG. 5: E fragment of the RTBV promoter was activated in tobacco BY-2 protoplasts by co-transfection of E::GUS with CsVMV::RF2b; CaMV 35S::RF2a and CaMV 35S::RF2a/CsVMV::RF2b.

As shown in FIG. 1, the E fragment of the RTBV promoter showed strong activity in tobacco BY-2 protoplasts, presumably because the BY-2 cell line contains RF2a- and RF2b-like transcription factors (Fukazawa et al., 2000). Nevertheless, the E fragment may be further stimulated by co-transfecting the BY-2 protoplasts with constructs that encode the RF2a and/or RF2b transcription factors. In this Example, the E fragment was activated in tobacco BY-2 protoplasts by co-transfection of E::GUS with CsVMV::RF2b, CaMV 35S::RF2a and CaMV 35S::RF2a/CsVMV::RF2b using methods well-known in the art. As shown in FIG. 5, the E fragment can be activated above a strong background expression by over-expression of RF2a and/or RF2b.

Example 4

Mutants of Box II

To investigate the possibility of reducing the background expression level in BY-2 protoplasts, the activities of certain Box II mutants (or "operational derivatives"), as shown in FIG. 6, were tested in BY-2 protoplasts. Specifically, the operational derivatives Box IIm1 (SEQ ID NO:2) and Box IIm2 (SEQ ID NO:3) were tested in the context of the E fragment (SEQ ID NO:63 and SEQ ID NO:64, respectively). The mutated promoters were ligated with the uidA coding sequence to create fusion genes, which are referred to herein as pE(Box IIm1)::GUS and pE(Box IIm2)::GUS. BY-2 protoplasts were then transfected with the pE(Box IIm1)::GUS and pE(Box IIm2)::GUS constructs. When the Box IIm1 and Box IIm2 elements were used, the GUS activity relative to the wild type Box II element (pE:GUS) dropped significantly (FIG. 7).

Figure 7:
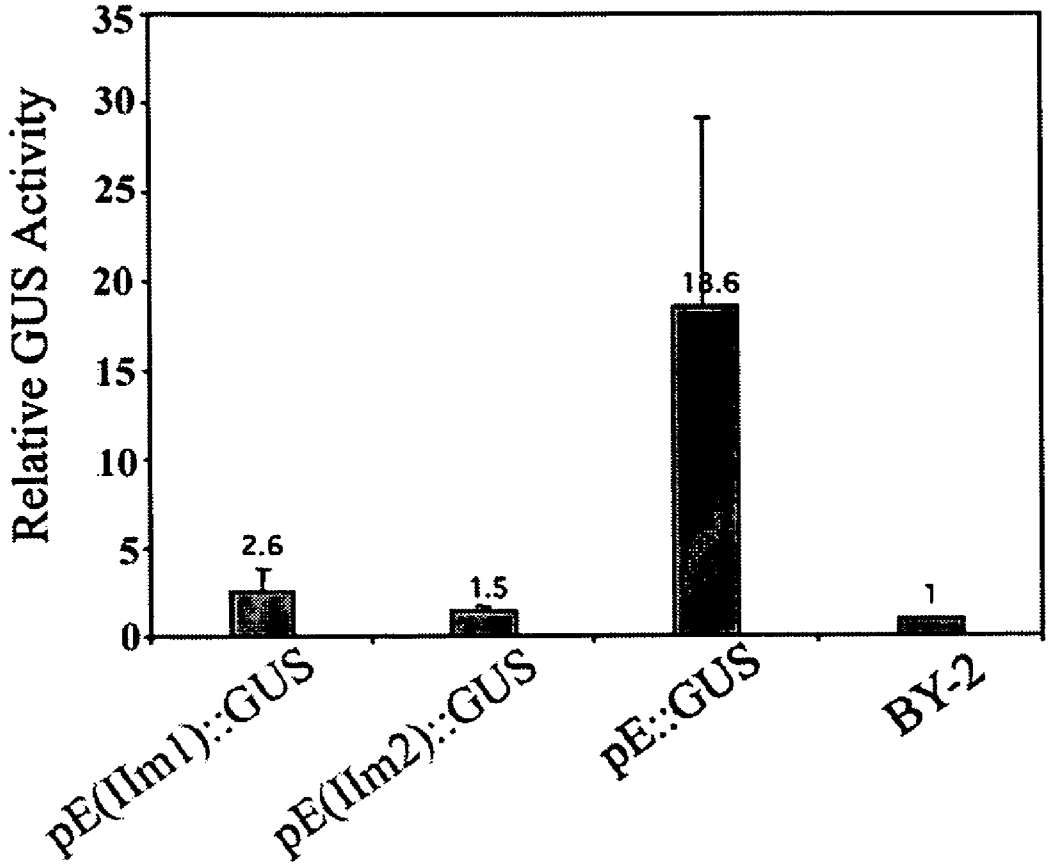
FIG. 7: Relative GUS activity of constructs pE(IIm1)::GUS, pE(IIm2)::GUS and pE::GUS in BY-2 protoplasts as described herein. pE(IIm1) comprised the E fragment, wherein the wild type Box II was replaced with the Box IIm1 element; pE(IIm2) comprised the E fragment, wherein the wild type Box II was replaced with the Box IIm2 element; pE comprised the E fragment and the wild type Box II element; and the bar labeled "BY-2" represents non-transgenic protoplasts.

In the case of the chimeric sequence pE(Box IIm2)::GUS, there was little, if any, GUS activity above that of non-transfected BY-2 cells (FIG. 7). These data suggest that there are endogenous transcription factors in BY-2 cells that can interact with the wild type Box II element, which results in expression of pE:GUS in protoplasts (FIGS. 1, 2 and 7). When operational derivatives of the Box II element were used, e.g., Box IIm1 and Box IIm2, the promoter activity was significantly abolished.

Example 5

Binding Affinities of RF2a and RF2b

A previous report showed that RF2a binds to the Box II element and its mutants with different affinities (Yin et al., 1997). To compare the binding affinities of RF2a and RF2b with the Box II element and its mutants, real time Surface Plasmon Resonance ("SPR") measurements were conducted using a BIAcore 2000 instrument. The binding affinities of RF2a and RF2b to these DNA targets were measured on chips on which biotin labeled-Box II, -Box IIm1 and -Box IIm2 elements were immobilized.

The association and de-association constants were determined using BIAevaluation 3.1 software—using 1:1 binding with a mass transfer model. The results are presented in FIG. 8. In general, RF2a has relatively higher binding affinities to the Box II, Box IIm1 and Box IIm2 elements when compared to RF2b. Furthermore, the DNA binding behavior of RF2a and RF2b are quite different from each other. RF2a appears to bind rapidly to the DNA target and slowly dissociates from the target, while RF2b binds slowly to the DNA target and releases from the target relatively quickly. The differences in the affinity of RF2a to the Box II element and its mutants, however, are not as dramatic as the differences of RF2b, while the relative order of affinities to the different target elements is the same for both proteins (FIG. 8).

To illustrate the biological relevance of the differences in the binding affinities described above, the pE::GUS, pE(Box IIm1)::GUS and pE(Box IIm2)::GUS constructs were used as reporters in BY-2 protoplast transient assays. In these assays, CaMV 35S::RF2a, CsVMV::RF2b and CaMV 35S::RF2a/CsVMV::RF2b were used as effectors. All results were normalized against the GFP internal control. The relative GUS activities of different sets of transfection assays are shown in FIG. 9 for the Box IIm1 element, and FIG. 10 for the Box IIm2 element.

Figure 9:
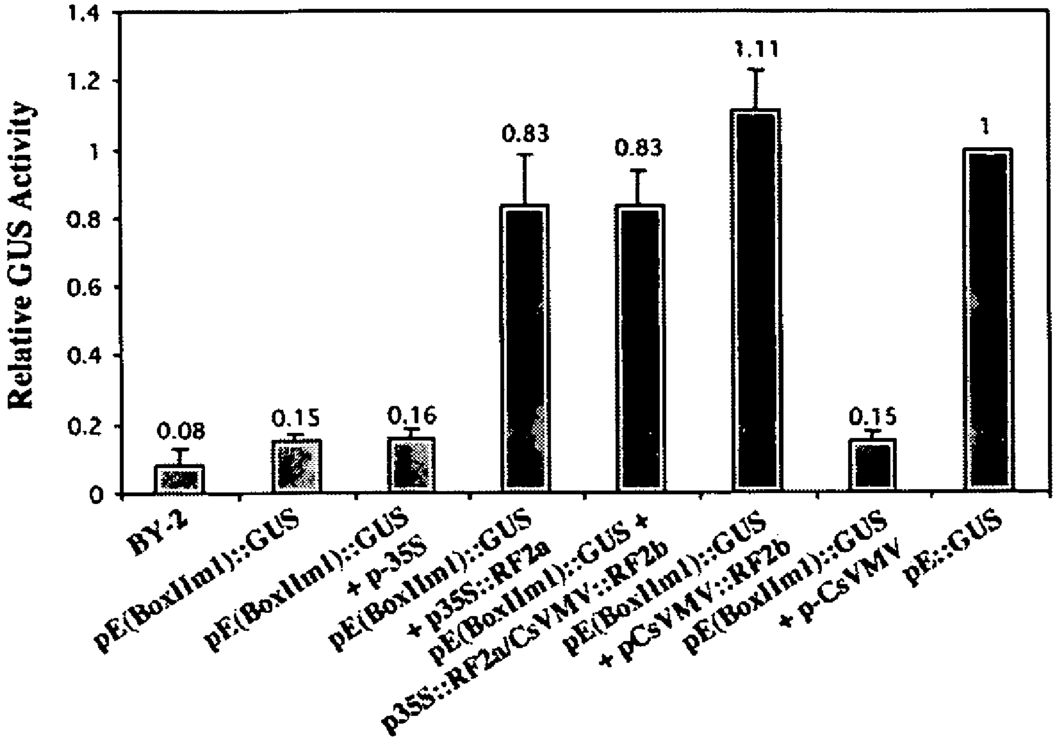
FIG. 9: The pE(Box IIm1):GUS construct was co-transfected into tobacco BY-2 protoplasts with CsVMV::RF2b, CaMV 35S::RF2a and 35S::RF2a/CsVMV::RF2b. All samples were normalized with GFP internal control.
Figure 10:
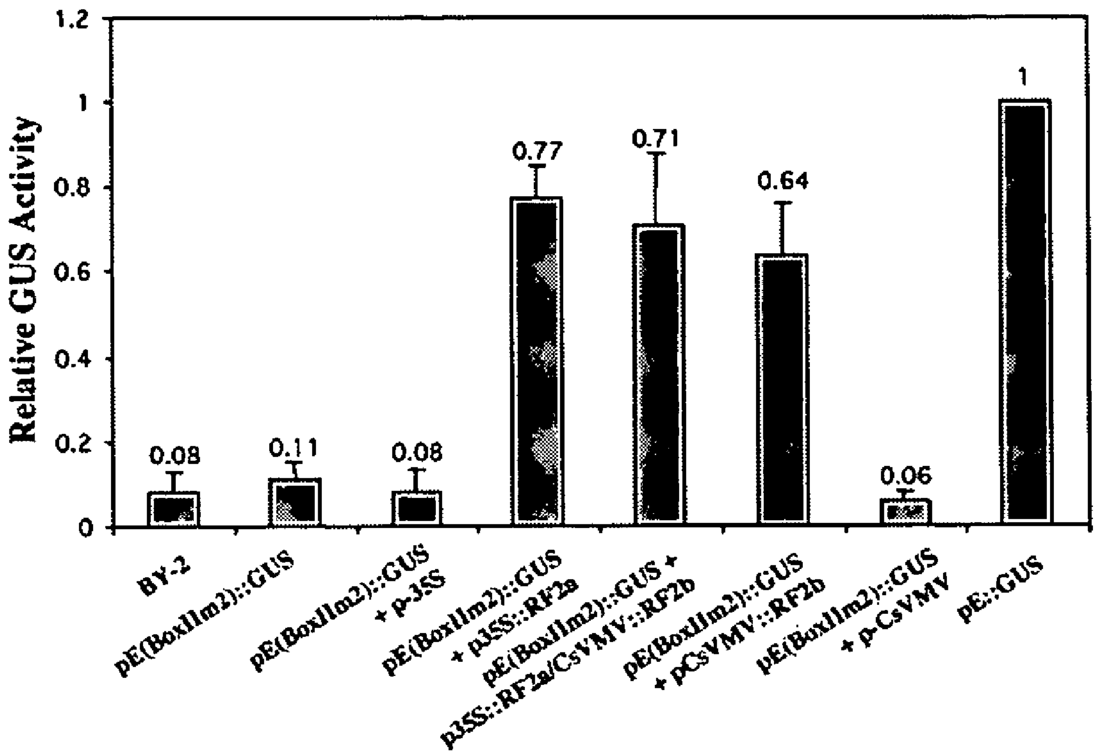
FIG. 10: The pE(Box IIm2):GUS construct was co-transfected into tobacco BY-2 protoplasts with CsVMV::RF2b, CaMV 35S::RF2a and CaMV 35S::RF2a/CsVMV::RF2b. All samples were normalized with GFP internal control.

When the foregoing constructs were co-transfected with CaMV 35S::RF2a, the promoter activity of E(Box IIm1) and E(Box IIm2) increased 5 to 7 fold (FIGS. 9 and 10). Furthermore, there was no apparent difference between the activation of promoters containing the Box IIm1 and Box IIm2 elements. Different results were observed when the foregoing constructs were co-transfected with CsVMV::RF2b. The E(Box IIm2) promoter was activated about 5.8 fold by RF2b, while the E(Box IIm1) promoter was activated about 7 fold (FIGS. 9 and 10). Importantly, this Example shows that the activity of the E(Box IIm1) promoter with RF2b was as high as the expression of the E wild type promoter in BY-2 protoplasts.

The foregoing data related to the interactions between the RF2a and/or RF2b transcription factors and the target chimeric promoters suggest that such promoters may, optionally, be designed to comprise the Box IIm1 and/or Box IIm2 elements to create a "zero" background expression level. In such case, the chimeric promoters may be activated by initiating the expression of the RF2a and/or RF2b transcription factors, which, of course, would interact with the Box IIm1 and/or Box IIm2 elements of the chimeric promoters, using compositions and methods described herein.

Example 6

Use of Box II and RF2a to Control Expression of Novel Chimeric Promoters

Figure 11:
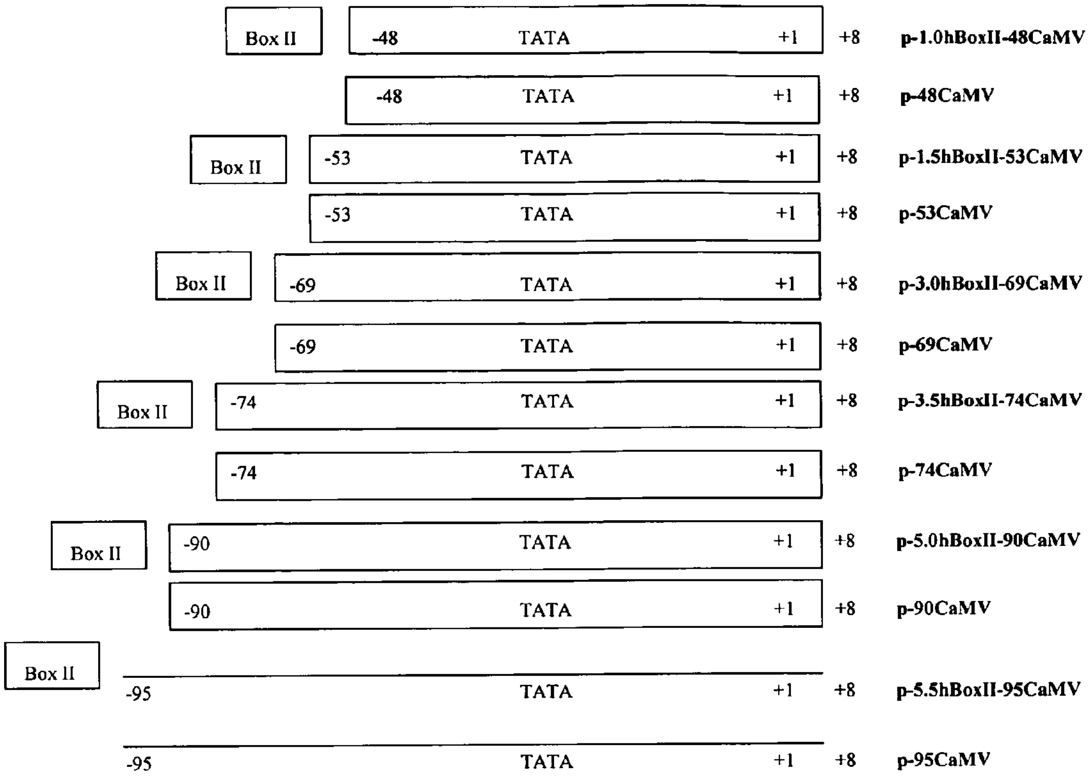
FIG. 11: Diagram of Box II and CaMV 35S chimeric promoters (and control). The chimeric promoters were ligated with a plasmid cassette that contained the uidA coding sequence followed by a Nos terminator. The names of the derived plasmids are shown to the right side of the diagram. The positions of Box II in the various constructs are in relation to the site of transcription initiation ("+1").

The following shows that the Box II element can be transferred to unrelated promoters, or promoter fragments, in a position dependent manner to control heterologous gene expression. To show that the Box II element is portable, Box II was fused with different lengths of the CaMV 35S promoter (FIG. 11). Specifically, the Box II element was fused to the 5' end of the chimeric promoters with a space of 7 nucleotides from the TATA box plus 1, 1.5, 3.0, 3.5, 5.0 and 5.5 "turns of DNA helix" (one turn=10.4 base pairs). The chimeric promoters were then inserted into a cassette with the uidA coding sequencing and Nos terminator.

Construction of Plasmids Comprising the Box II Element and Different Lengths of the CaMV 35S Promoter—To construct Box II and CaMV 35S chimeric promoters, the Box II element was introduced into CaMV 35S promoter sequences of different lengths through PCR reactions using Pfu DNA polymerase (Stratagen Systems, Kirkland, Wis.). Forward primers for the PCR reactions were designed to have a HindIII restriction site, followed by the Box II sequence, which was followed by part of the 5' CaMV promoter at desired positions (see FIG. 12 and Table 2 for specific primer sequences). The GUS 3' primer (SEQ ID NO:36) was used as reverse primer for all reactions.

TABLE 2

| | Promoter | Primer Set | 5' Primer |
|---|---|---|---|
| 1 | −1.0hBoxII−48CaMV | −1.0hBoxII−48CaMV/GUS 3' | SEQ ID NO: 37 |
| 2 | −1.5hBoxII−53CaMV | −1.5hBoxII−53CaMV/GUS 3' | SEQ ID NO: 38 |
| 3 | −3.0hBoxII−69CaMV | −3.0hBoxII−69CaMV/GUS 3' | SEQ ID NO: 39 |
| 4 | −3.5hBoxII−74CaMV | −3.5hBoxII−74CaMV/GUS 3' | SEQ ID NO: 40 |
| 5 | −5.0hBoxII−90CaMV | −5.0hBoxII−90CaMV/GUS 3' | SEQ ID NO: 41 |
| 6 | −5.5hBoxII−95CaMV | −5.5hBoxII−95CaMV/GUS 3' | SEQ ID NO: 42 |

The p35S:GUS plasmid was used as template in the foregoing reactions. In the p35S:GUS plasmid, a NcoI restriction site was located between the CaMV 35S promoter and the GUS coding sequence. Thus, a NcoI site was present in all PCR products. The PCR products were restricted with HindIII/NcoI and cloned into a pE:GUS vector to replace the E promoter through the same set of restriction sites. The constructed plasmids containing the chimeric promoters labeled 1 through 6 in Table 2 were named p-1.0hBoxII−48CaMV:GUS, p-1.5hBoxII−53CaMV:GUS, p-3.0hBoxII−69CaMV:GUS, p-3.5hBoxII−74CaMV, p-5.0hBoxII−90CaMV:GUS, and p-5.5hBoxII−95CaMV:GUS, respectively. The controls for this set of plasmids were generated using primer sets 1.5h-53CaMV-c (SEQ ID NO:43)/GUS3'; −3.5h-74CaMV-c (SEQ ID NO:44)/GUS3' and −5.5h-95CaMV-c (SEQ ID NO:45)/GUS3', which products were cloned into pE:GUS with HindIII/NcoI to replace the E promoter. The derived plasmids/constructs were named p-53CaMV:GUS, p-74CaMV:GUS and p-95CaMV:GUS, respectively.

Figure 13:
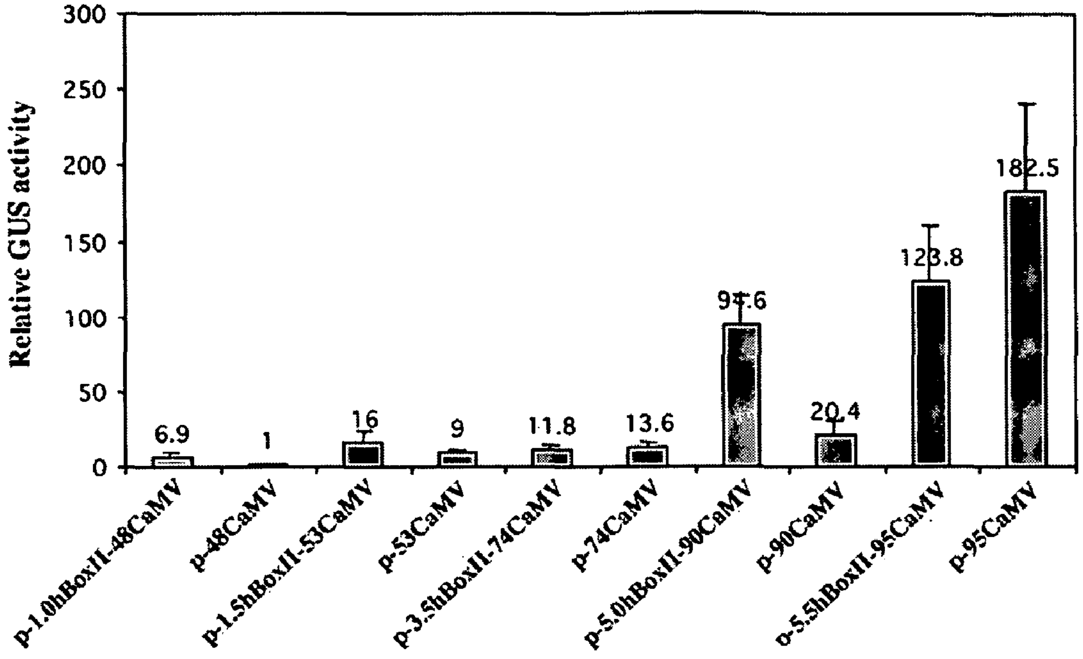
FIG. 13: Relative GUS activities in non-transgenic BY-2 protoplasts of constructs in which uidA was driven by promoters that comprised Box II and portions of the CaMV 35S promoter, which are illustrated in FIG. 11. The GUS activity of each sample was normalized against the GFP internal control.

The foregoing constructs were then transfected into non-transgenic BY-2 protoplasts, and the resulting GUS activity determined. The data in FIG. 13 show that when the Box II element is fused with the CaMV 35S promoter with a space of 7 nucleotides from the TATA box plus one or more full turns of DNA helix (p1.0hBoxII−48CaMV and p5.0hBoxII−90CaMV), gene expression was dramatically stimulated, compared to reporter genes that lack Box II (p-48CaMV and p-90CaMV, respectively). The p1.0hBoxII−48CaMV and p5.0hBoxII−90CaMV constructs yielded 6.9 and 4.7 fold increases in expression level above p-48CaMV and p-90CaMV, respectively, which did not contain the Box II element.

In contrast, when the Box II element was fused to fragments of the CaMV 35S promoter at positions of 7 nucleotides from the TATA box plus multiples of 0.5 turns of DNA helix (p-1.5hBox II−53CaMV versus p-53CaMV; p-3.5hBox II−74CaMV versus p-74CaMV; and p-5.5hBox II−95CaMV versus p-95CaMV), there was much less or no stimulation of gene expression. Of course, these results indicate that the Box II element, and its operational derivatives, can be used to control and/or enhance gene expression in unrelated promoters, preferably, when it is located approximately 7 nucleotides from the TATA box plus one or more full turns of DNA helix.

To illustrate the regulatory effect of transcription factors RF2a and RF2b on the activity of the Box II element and novel chimeric promoters containing the Box II element, each plasmid/construct illustrated in FIG. 11 was tested in transgenic BY-2 protoplasts that produce RF2a, or RF2a plus RF2b. In these experiments, as shown in FIG. 14, the trend of promoter stimulation was consistent with that shown in non-transgenic BY-2 cells, i.e., activation of promoters that contain the Box II element at 7 nucleotides plus 1.0 and 5.0 helices distance from the TATA box was higher than that of the promoters in which the Box II element was placed 1.5, 3.5, and 5.5 helices distance from the TATA box. The total amount of GUS expression exhibited by the chimeric promoter constructs, however, was much greater in transgenic cell lines that produce elevated levels of RF2a (FIG. 14(A)), or RF2a plus RF2b (FIG. 14(B)), than in non-transgenic protoplasts that did not contain elevated levels of such proteins (compare the relative GUS expression levels in FIG. 14 to FIG. 13).

The foregoing data from BY-2 wild type and transgenic cell lines indicate that the Box II element, and its operational derivatives, can regulate the expression of unrelated promoters, e.g., the CaMV 35S chimeric promoters described above, as it can in the RTBV promoter. Furthermore, the data indicate that the effect of the Box II element, and its operational derivatives, is, preferably, imparted in a position and/or orientation dependent manner—as described above.

Example 7

Validation of Transient Assay Data From Tobacco BY-2 Protoplasts in Transgenic *Arabidopsis*

Figure 15:
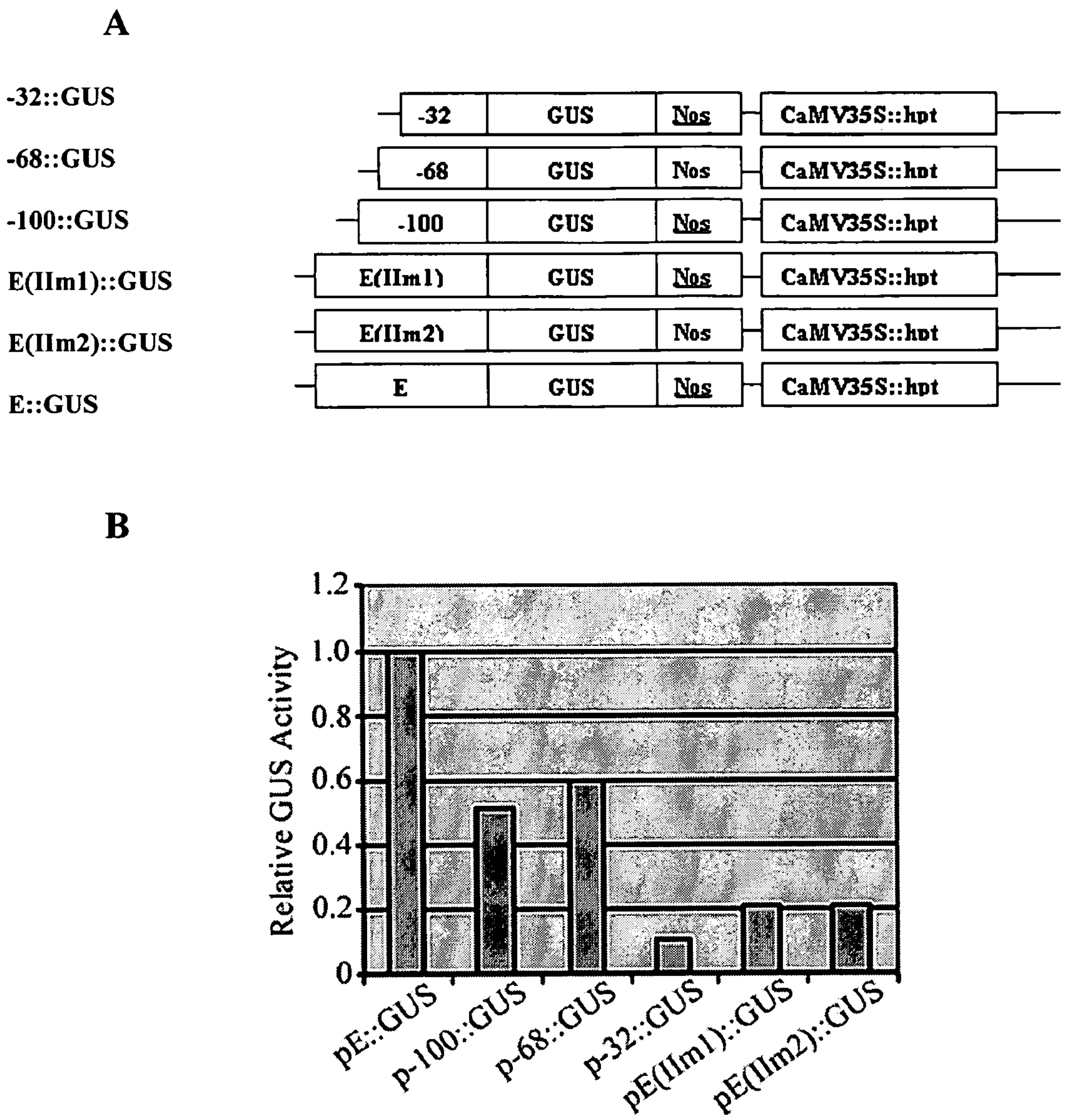
FIG. 15: A: Diagram of the T-DNA regions of binary plasmids used for *Agrobacterium*-mediated transformation of *Arabidopsis thaliana*. B: GUS activity of $T_1$ transgenic *Arabidopsis* plants. The results present the mean value of at least 15 independent transgenic plants. The relative GUS activity was calculated by comparison with E::GUS (=1).

To evaluate the data presented above from the transient assays, binary vectors were built and transformed into *Arabidopsis* plants through *Agrobacterium*-mediated transformation. The set of binary vectors that were transformed into plants were constructs with different deletions of the RTBV promoter, which comprised the various portions of the E fragment described in Example 1; the E fragment containing either the Box IIm1 or Box IIm2 element; or the wild type E fragment (See FIG. 15A). In the transformed *Arabidopsis* plants, the activity of the chimeric promoters, which comprised the Box IIm1 or Box IIm2 element, was near the basal level of expression, which was observed for the construct p-E(32)::GUS, in which all the cis elements of RTBV promoter up-stream of the TATA box were removed (FIG. 15B). Thus, the foregoing data agree with the data generated in the transient protoplasts analysis described in Example 5, wherein the chimeric promoters of the present invention may, for example, be designed to comprise the operational derivatives Box IIm1 and/or Box IIm2 to create a near "zero" background expression level in the absence of RF2a and/or RF2b.

Example 8

RF2a Mutants with Deletions of Functional Domains

Figure 16:
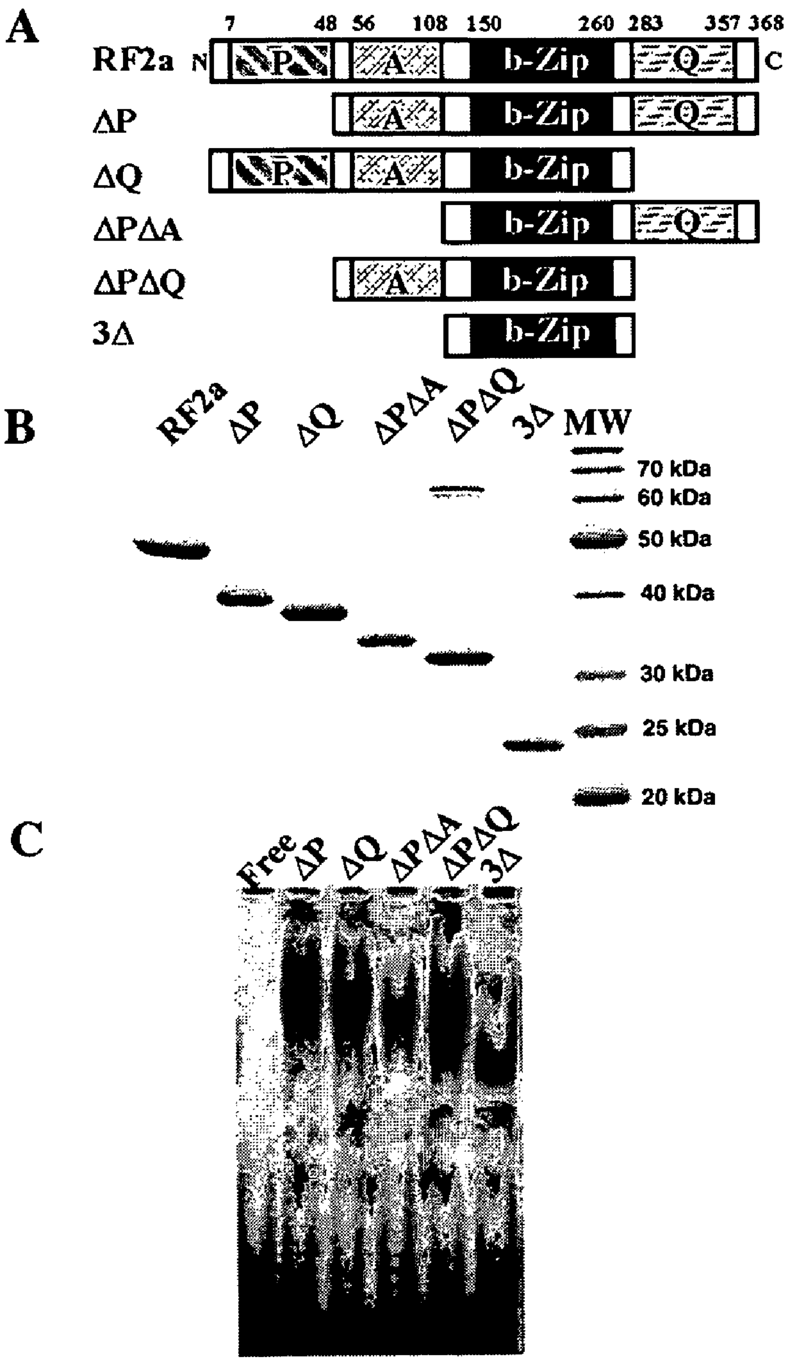
FIG. 16: Electrophoretic mobility shift assay of protein-DNA complexes formed between mutants of RF2a and the Box II element. A: Schematic diagram of mutants of RF2a. "A" represents the acidic domain; "P" represents the proline-rich domain; and "Q" represents the glutamine-rich domain. B: SDS-PAGE analysis of the purified RF2a mutant proteins. C: Gel mobility shift assay using purified mutant proteins of RF2a as labeled. A control lane without protein (labeled "Free") was included in the assay. Box IIm1 DNA was labeled with $^{32}P$, and radioactivity was detected by autoradiography.

It has been shown that the bZIP protein RF2a enhances transcription in vivo and in vitro. It is further known that the RF2a transcription factor comprises a proline-, acidic- and glutamine-rich domain. To analyze the function of each domain, mutants of RF2a were created by removing one or more of the foregoing putative domains as shown in FIG. 16(A). More particularly, mutants of RF2a were created in which the proline-rich domain was removed (RF2a-ΔP); the glutamine-rich domain was removed (RF2a-ΔQ); the proline-rich and acidic domains were removed (RF2a-ΔPΔA); the proline- and glutamine-rich domains were removed (RF2a-ΔPΔQ); and the glutamine-rich, proline-rich and acidic domains were removed (RF2a-3Δ). The coding sequence for each mutant was cloned into the bacterial expression vector pET28a, in which a $His_6$ tag was placed at the N-terminus of the fusion protein. The derived plasmids were named pET-RF2a (encoding full-length RF2a), pET-RF2a-ΔP, pET-RF2a-ΔQ, pET-RF2a-ΔPΔA, pET-RF2a-ΔPΔQ, and pET-RF2a-3Δ.

Plasmid Construction for Protein Purification—The sequences encoding the foregoing mutants of RF2a were created through PCR amplification. A NdeI restriction site was added to the 5' end of all primers, and the ATG in the restriction site was in frame with the $His_6$ tag in vector pET28a (Invitrogen Corp., Carlsbad, Calif.) and served as the transcription start codon for the plasmids described in Example 9. A BamHI site was added to all the 3' primers with a stop codon in front of the restriction site. The primers used for amplification of the various fragments of RF2a are listed in Table 3 below:

TABLE 3

| | |
|---|---|
| RF2a 5' | SEQ ID NO: 46 |
| RF2a-ΔP 5' | SEQ ID NO: 47 |
| RF2a-ΔPΔA 5': | SEQ ID NO: 48 |
| RF2a 3' | SEQ ID NO: 49 |
| RF2a-ΔQ 3' | SEQ ID NO: 50 |

From a complete RF2a-encoding sequence (SEQ ID NO:7), the ΔP fragment was amplified using primers RF2a-ΔP 5' and RF2a 3'; ΔQ was amplified using primers RF2a 5' and RF2a-ΔQ 3'; ΔPΔA was amplified using primers RF2a-ΔPΔA 5' and RF2a 3'; and ΔPΔQ was amplified using primers RF2a-ΔP 5' and RF2a-ΔQ 3'. The construction of pET-RF2a-3Δ and pET-RF2a were described by Petruccelli et al. (2001). All of the fragments were restricted with NdeI and BamHI and were cloned into pET28a through the same set of restriction sites. All of the mutations were verified by DNA sequence analysis. The derived plasmids were designated pET-RF2a-ΔP, pET-RF2a-ΔQ, pET-RF2a-ΔPΔA, pET-RF2a-ΔPΔQ, pET-RF2a (encoding full-length RF2a), and pET-RF2a-3Δ.

Protein Purification—The pET28a-derived plasmids were transformed into *Escherichia coli* strain BL21 (DE3)pLysS for protein expression. Protein expression was induced with 0.5 mM isopropyl-β-D-thiogalactopyranoside at room temperature for 3 hours after the cell density reached $A_{600}$ of ~0.6. The His-tagged proteins were purified according to procedures provided by Novagen, Inc. (Madison, Wis.) under non-denaturing conditions. The purified recombinant proteins were dialyzed in 1× phosphate-buffered saline with 20% glycerol to remove imidazole and stored at −70° C.

The purified mutant proteins were then analyzed by SDS-PAGE to confirm that each protein was its expected size (FIG. 16(B)). To confirm that each of the mutant proteins bind to the DNA target, i.e., the Box II element and/or its operational derivatives, gel mobility shift assays were carried out with the purified recombinant proteins (FIG. 16(C)). The electrophoretic mobility shift assays were carried out essentially as described in Yin and Beachy (1995). 100 ng of proteins purified from the transformed *E. coli* were incubated with $^{32}$P-labeled Box IIm1 DNA probe followed by electrophoresis in a 5% acrylamide gel (Yin et al., 1997) (FIG. 16(C)). The data presented in FIG. 16(C) demonstrate that proteins ΔP (SEQ ID NO:68), ΔQ (SEQ ID NO:69), ΔPΔA (SEQ ID NO:70), ΔPΔQ (SEQ ID NO:71), and 3Δ (SEQ ID NO:72) of RF2a bind to the Box IIm1 element.

Example 9

Contribution of RF2a Domains to Activity

The relative activity of RF2a and the RF2a mutants (described in Example 8) was then measured. First, a chimeric promoter was developed with a single copy of the Box II element fused to the 5' end of a minimal CaMV 35S promoter comprising nucleotides −48 to +8 (SEQ ID NO:66). The chimeric promoter was ligated to the uidA coding sequence to create the reporter pBII-48Ca::GUS.

To analyze the function of the several domains of RF2a, effectors were created by inserting coding sequences of RF2a or the mutants of RF2a (described in Example 8) downstream of the enhanced CaMV 35S promoter in the pMON999 vector (a gift from Monsanto Company, St. Louis, Mo.). The resultant constructs, p35S::RF2a, p35S::RF2a-ΔP, p35S::RF2a-ΔQ, p35S::RF2a-ΔPΔA, p35S::RF2a-ΔPΔQ and p35S::RF2a-3Δ, were co-transfected into BY-2 protoplasts with pBII-48Ca::GUS (FIG. 17(A)). Plasmid pCat-GFP, in which the GFP gene was driven by CaMV 35S promoter, was co-introduced to serve as an internal control. The following describes, in greater detail, the construction of these vectors and the methods employed in transfecting the same into BY-2 protoplasts.

Plasmids for protoplast transfection—The coding sequences for mutants of RF2a were released from pET28a-derived plasmids and cloned into the plant expression vector pMON999 (a gift from Monsanto Company, St. Louis, Mo.) to place each gene downstream of an enhanced CaMV 35S promoter, followed by a nopaline synthase terminator sequence. The resulting effector constructs were named p35S::RF2a, p35S::RF2a-ΔP, p35S::RF2a-ΔQ, p35S::RF2a-ΔPΔA, p35S::RF2a-ΔPΔQ and p35S::RF2a-3Δ. The reporter gene construct, pBII-48Ca::GUS, was built using PCR to introduce the Box II element into a minimal CaMV 35S promoter comprising nucleotides −48 to +8 with primers BII-48Ca 5' (SEQ ID NO:53) (which contained the Box II element) and GUS 3' (SEQ ID NO:36) using a p35S:GUS plasmid as template. The PCR product was restricted with HindIII and NcoI, and the resulting fragment was inserted into p35S::GUS to replace the original 35S promoter.

Transfection of tobacco BY-2 protoplasts—The protoplasts were isolated from tobacco cell line BY-2 as described by Watanabe et al. (1987). Approximately one million protoplasts were transfected by electroporation with 20 μg of effector construct DNA, 15 μg of herring sperm DNA, 2.5 μg of reporter gene construct DNA, and 15 μg of pCat-GFP DNA. In samples with reporter gene alone, the total amount of DNA was adjusted by adding 20 μg of herring sperm carrier DNA. The electroporation parameters used were 300 V and 250 microfarads with the Bio-Rad electroporation system (Bio-Rad Laboratories, Hercules, Calif.). Protoplast samples were cultured in Murashige and Skoog medium with 0.4 M mannitol, pH 5.8, at 28° C. The protoplasts were collected 24 hours after electroporation.

Figure 17:
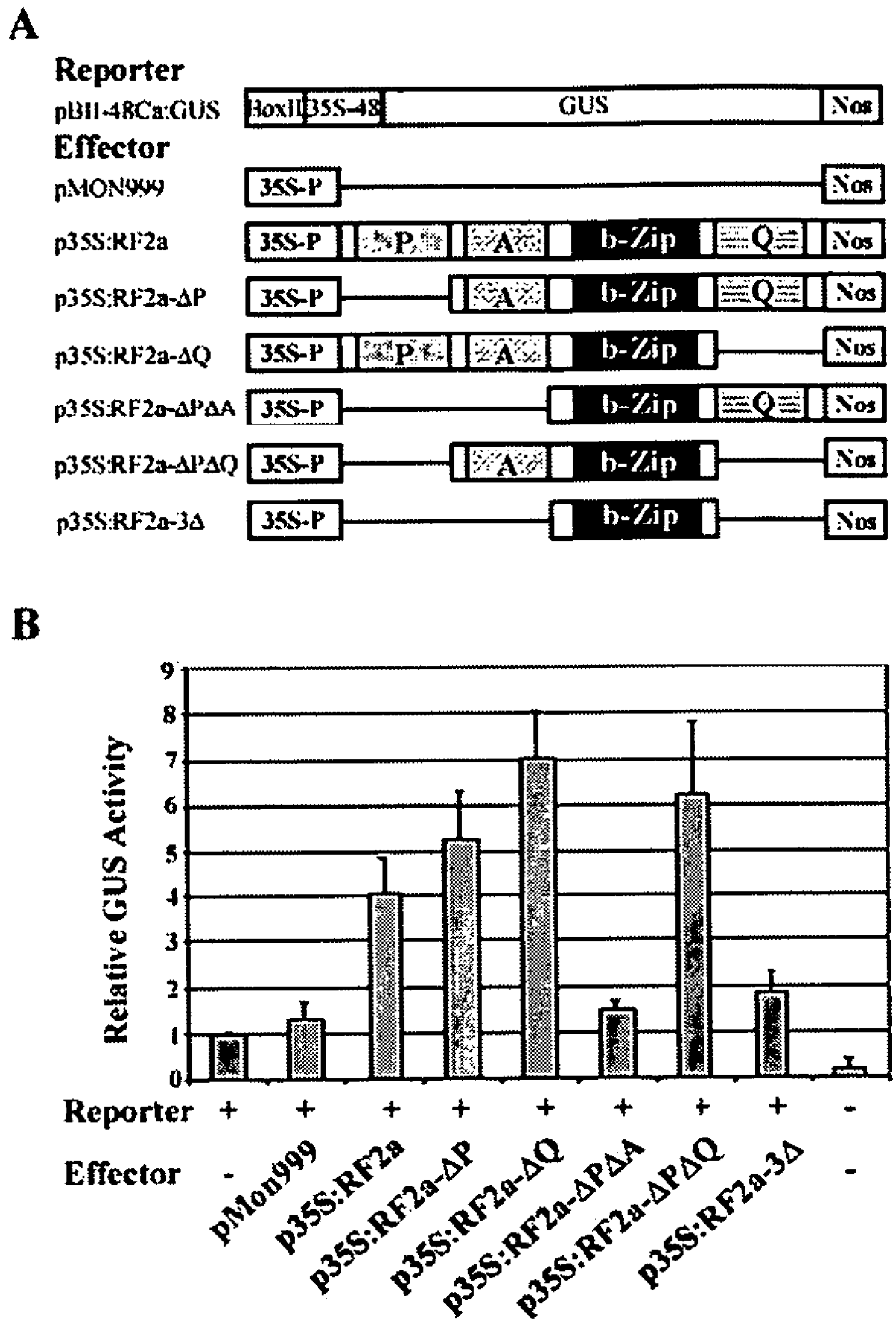
FIG. 17: Effects of RF2a and mutants of RF2a on gene expression in BY-2 protoplasts. A: Reporter and effector gene constructs. The GUS reporter gene (uidA sequence) was driven by a promoter that comprised the Box II element operatively linked to nucleotides −48 to +8 of the CaMV 35S promoter, and was followed by a nopaline synthase 3' terminator sequence ("pBII-48Ca:GUS"). Effectors included sequences encoding RF2a and RF2a mutants operatively linked to the CaMV 35S promoter and nopaline synthase terminator. B: Relative GUS activities in BY-2 protoplasts that were co-transfected with Reporter and Effector gene constructs described herein. The results represent the averages of detected GUS activities (with S.D.) of three independent experiments, three samples per experiment, after normalization with GFP.

As shown in FIG. 17(B), the transactivation function of RF2a was not decreased by removing either the proline-rich (35S::RF2a-ΔP) or glutamine-rich (35S::RF2a-ΔQ) domains or both of the domains (35S::RF2a-ΔPΔQ). In fact, the activation function of each of these mutants was greater than that of full-length RF2a. RF2a-ΔP was significantly different from RF2a at the $P_{0.05}$ level, whereas RF2a-ΔQ and RF2a-

ΔPΔQ were significantly different from RF2a at the $P_{0.01}$ level (Student's t test). Also, the difference between the activity of RF2a-ΔP and RF2a-ΔQ was significant at the $P_{0.01}$ level, and there was no difference between RF2a-ΔQ and RF2a-ΔPΔQ. The data suggest that the proline-rich and glutamine-rich domains do not contribute in a positive way to the activation function of RF2a. In contrast, the activity dropped to near basal level when the acidic domain was removed (RF2a-ΔPΔA and RF2a-3Δ) (FIG. 17(B)). These results suggest that the acidic domain is responsible for the activation of gene expression by RF2a.

Example 10

Functions of RF2a Domains in Fusion Proteins

Figure 18:
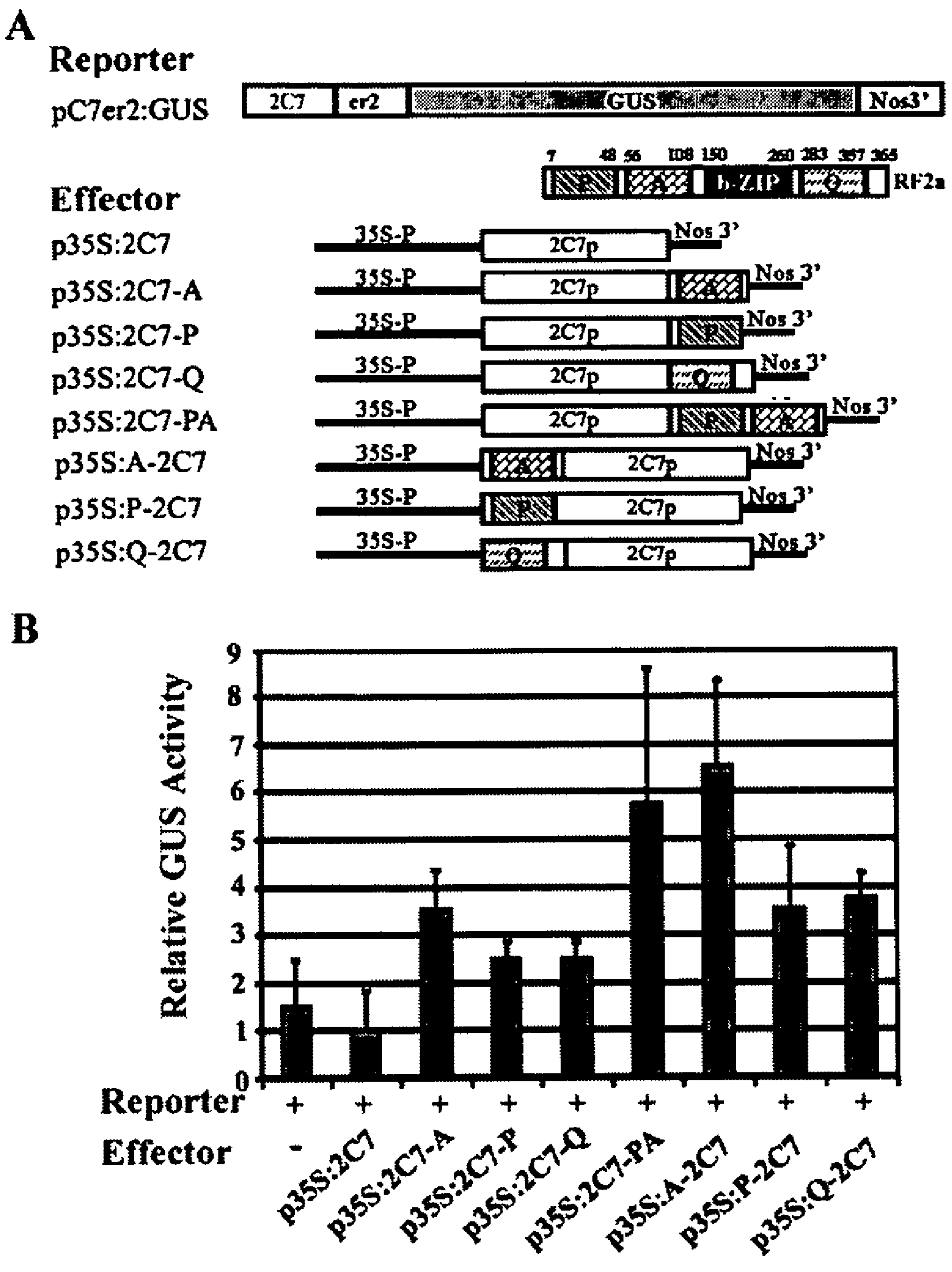
FIG. 18: The effects of RF2a domains on gene expression when in fusion with the 2C7 DNA-binding domain. A: Diagram of reporter and effector constructs used for transient assays involving fusion proteins of RF2a functional domains with the 2C7 synthetic zinc finger DNA-binding domain. B: Relative GUS activities in BY-2 protoplasts that were co-transfected with the reporter and effector gene constructs as indicated herein. The results represent the averages (with S.D.) of three independent experiments, three samples per experiment, after normalization with GFP.

To determine whether domains of RF2a can serve as independent modules to regulate transcription, the various putative functional domains were fused with the synthetic 2C7 protein (SEQ ID NO:75), a synthetic zinc finger DNA-binding domain that specifically binds to the 2C7 DNA-binding site (SEQ ID NO:74), to create various "effector" constructs (FIG. 18(A)). The various RF2a domains were placed either at the N-terminus or the C-terminus of the 2C7 DNA-binding domain ("DBD"). The "reporter" construct pC7er2:GUS carried the uidA coding sequence located downstream of a chimeric promoter comprising 6×2C7-binding sites ligated with the minimal promoter of erbB-2 ("er2"). p35S:2C7 encoded the 2C7 protein without an activation domain and served as a control (FIG. 18(A)).

To create effectors with RF2a domains fused to the N-terminus of 2C7 DBD, coding sequences for the acidic domain (A) (SEQ ID NO:9), proline-rich domain (P) (SEQ ID NO:54) and glutamine-rich domain (Q) (SEQ ID NO:55) were amplified using primer pairs A-2C7 5'/A-2C7 3', P-2C7 5'/P-2C7 3', and Q-2C7 5'/Q-2C7 3', respectively, with pET-RF2a as template. BglII and BamHI restriction sites were introduced into the 5' and 3' primers, respectively. The particular sequences of the foregoing primers are referenced in Table 4 below:

TABLE 4

| | |
|---|---|
| A-2C7 5' | SEQ ID NO: 56 |
| A-2C7 3' | SEQ ID NO: 57 |
| P-2C7 5' | SEQ ID NO: 58 |
| P-2C7 3' | SEQ ID NO: 59 |
| Q-2C7 5' | SEQ ID NO: 60 |
| Q-2C7 3' | SEQ ID NO: 61 |

The products created by the foregoing PCR reactions were restricted with the BglII and BamHI and cloned into pMON999 through BglII and EcoRI sites along with the DNA fragment that encoded the 2C7 DNA-binding domain (SEQ ID NO:76) (The 2C7 DNA-binding domain coding sequence was previously released from p35S:2C7 using BamHI and EcoRI). The resulting plasmids were designated p35S:A-2C7, p35S:P-2C7, and p35S:Q-2C7.

For effectors with RF2a domains at the C-terminus of the 2C7 DBD, coding sequences for the A, P, Q, and P plus A (PA) domains were released from pET-RF2a-A, pET-RF2a-P, pET-RF2a-Q, and pET-RF2a-PA using the enzymes XbaI and EcoRI and cloned into p35S:2C7-VP16 to replace the VP16 domain with the same restriction sites. The resultant plasmids were named p35S:2C7-A, p35S:2C7-P, p35S:2C7-Q, and p35S:2C7-PA.

Each of the foregoing effector constructs, as illustrated in FIG. 18(A), were co-transfected into BY-2 protoplasts along with the reporter construct. The relative GUS activities of the transfected protoplasts were subsequently determined. As shown in FIG. 18(B), when domains of RF2a were placed at the C-terminus of the 2C7 protein, 2C7-A and 2C7-PA showed significant activation function. When the domains were fused individually at the N-terminus of 2C7, the acidic domain (A-2C7) conferred stronger activation than the P(P-2C7) or Q (Q-2C7) domains. The function of the acidic domain in the fusion proteins is consistent with its function in RF2a, although the position of this domain in the fusion proteins appears to affect its activity. The proline- and glutamine-rich domains had no effect on gene expression when they were placed at the C-terminus of the 2C7 DBD; however, these domains showed mild activation function when they were fused at the N-terminus of the 2C7 DBD.

Example 11

Impact of Mutants of RF2a on Plant Development

Previous studies have shown that transgenic rice and tobacco plants that overexpressed RF2a were normal in appearance and reproduction. (Yin et al., 1997; Petruccelli et al., 2001). To determine whether mutants of RF2a in which one or more domains were removed had a positive or negative effect on plant development, transgenic plants that overexpress mutants of RF2a were produced. Fifteen or more independent transgenic tobacco lines were developed with the constructs described below through *Agrobacterium*-mediated transformation.

Plasmids for *Agrobacterium*-mediated transformation—The fusion genes described above relating to the plant expression constructs comprising RF2a deletion mutants were released from pMON999-derived plasmids using NotI (blunted) and cloned into the binary vector pGA-E::GUS (Petruccelli et al., 2001) using the blunt HindIII site (downstream of a CaMV 35S promoter sequence). The final plasmids were named pGA-E::GUS/P-35S::ΔP, pGA-E::GUS/P-35S::ΔQ, pGA-E::GUS/P-35S::ΔPΔA and pGA-E::GUS/P-35S::ΔPΔQ. A plasmid encoding full-length RF2a, p35S::RF2a, was also constructed using the methods described herein.

Tobacco transformation—the plasmids described above were introduced into *Agrobacterium tumefaciens* strain LBA4404 and used for tobacco transformation. Leaf discs from *Nicotiana tabacum* cv. Xanthi NN were transformed with the various plasmids following the protocol of Horsch et al. (1988). At least 15 independent transgenic lines were produced with each gene construct. Transgenic plants were self-fertilized, and $T_1$ seeds were collected. The $T_1$ seeds were germinated on Murashige and Skoog medium (Murashige and Skoog, 1962) with kanamycin (100 mg/L) selection, and $Kan^r$ seedlings were grown in a greenhouse for observation.

Figure 19:
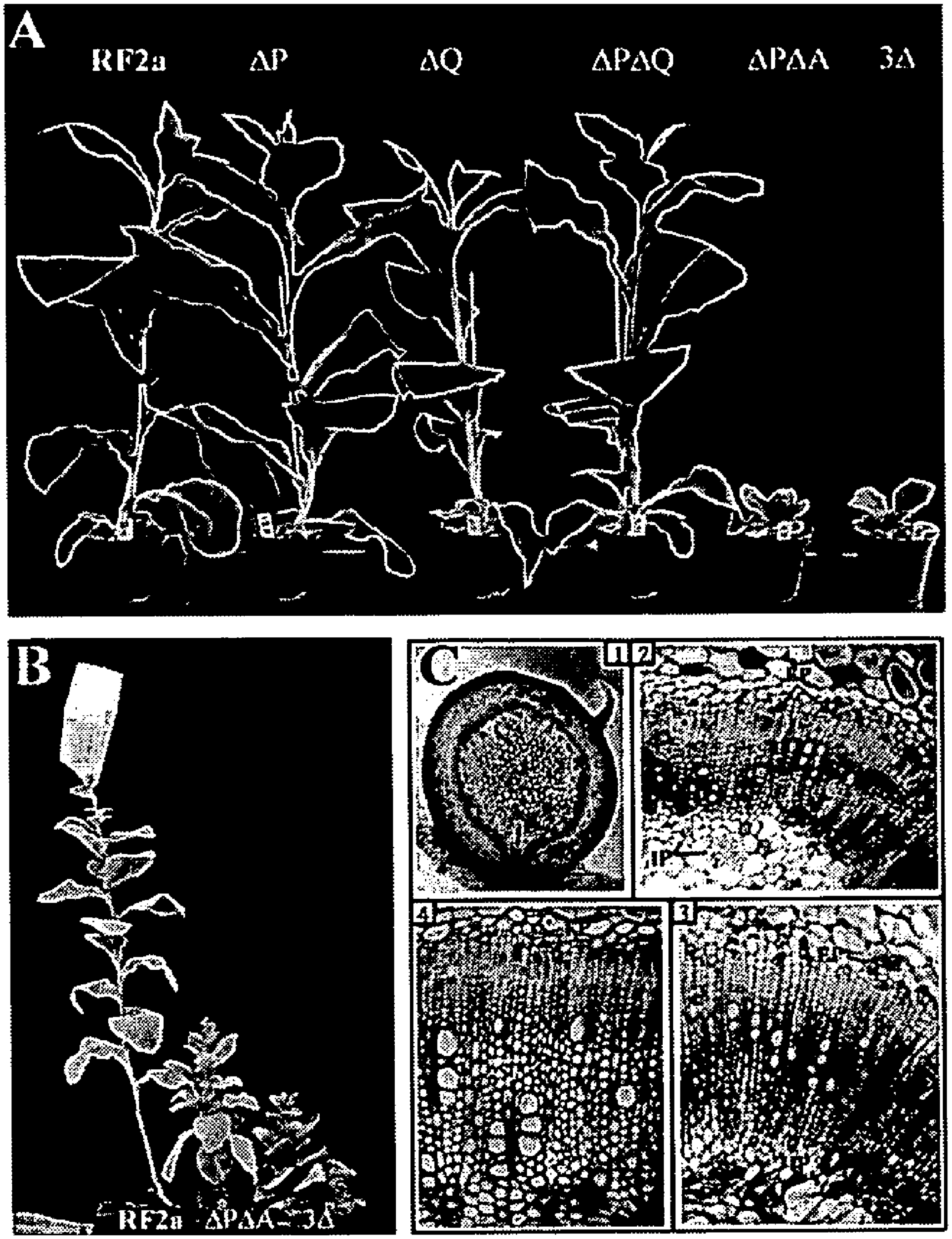
FIG. 19: Impact of RF2a and RF2a mutants on development of transgenic tobacco plants. A: Two-month old transgenic tobacco plants with RF2a and mutants of RF2a driven by the 35S promoter were grown under greenhouse conditions. Only transgenic plants with mutants lacking the acidic domain (RF2a-ΔPΔA and RF2a-3Δ) showed severe stunting phenotype. B: Transgenic plants at 105 days. Leaves of plants with RF2a-ΔPΔA and RF2a-3Δ were curved downward, and flowering time was significantly delayed. C: Panel 1: Transversal section of the stem of transgenic plants with RF2a-ΔPΔA in low magnification; Panel 2-4: Transverse sections of the lower part of stems of two-month old tobacco plants stained with toluidine blue O. Panel 2, transgenic plant with RF2a-ΔPΔA. Panel 3, transgenic plant with RF2a-3Δ. Panel 4, Non-transgenic plant.

Following PCR analysis, transgenic lines expressing each mutant were observed for phenotypic changes. $T_1$ generation plants with 35S::RF2a, 35S::RF2a-ΔP, 35S::RF2a-ΔQ, and 35S::RF2a-ΔPΔQ did not exhibit abnormal phenotypes (FIG. 19(A)). However, 11 of 15 independent transgenic lines with 35S::RF2a-ΔPΔA exhibited mild to severe stunting with curved leaves and substantial delay in flowering times (FIGS. 19(A) & (B)). Furthermore, the internodal elongation of transgenic plants was strongly repressed by RF2a-ΔPΔA (FIG. 19(C), Panel 1). The phenotype caused by 35S::RF2a-ΔPΔA was similar to, but less severe than, the phenotype caused by 35S::RF2a-3Δ. Cross-sections of the stem of transgenic plants with either RF2a-ΔPΔA or RF2a-3Δ showed that the xylem of stunted plants was not uniformly lignified and that phloem development was altered. (FIG. 19(C)).

Figure 20:
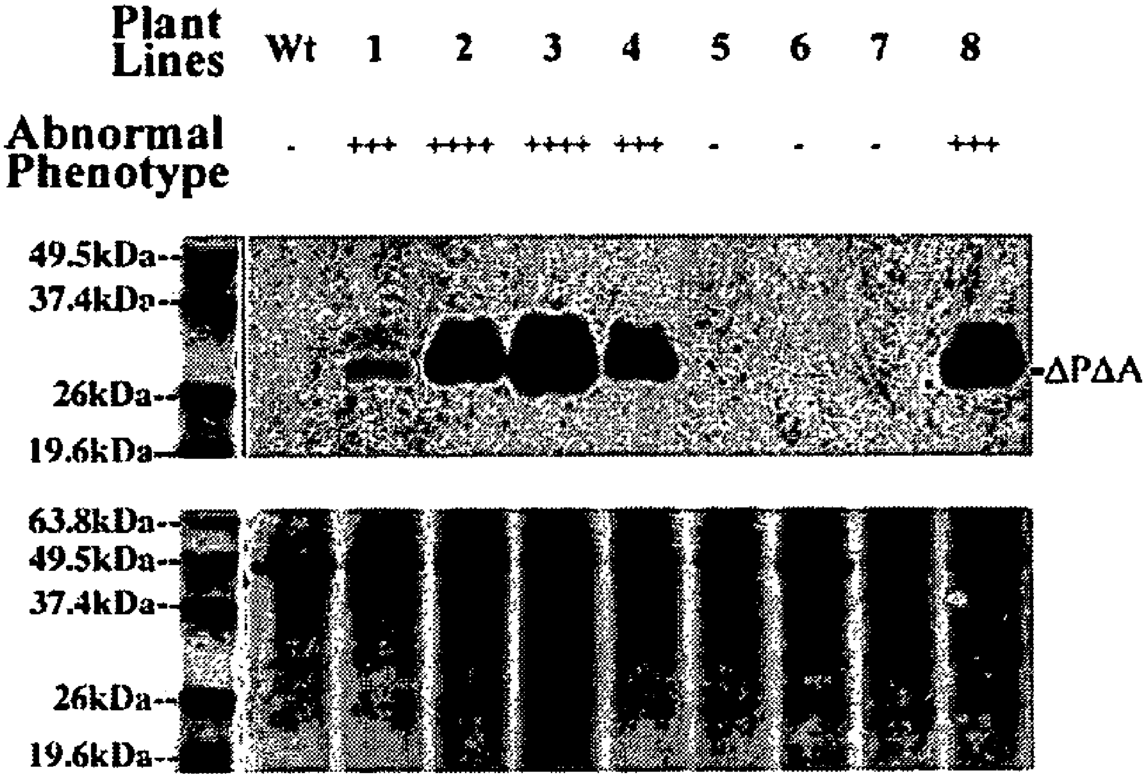
FIG. 20: Correlation between severity of abnormal phenotypes shown in FIG. 19 and accumulation of RF2a-ΔPΔA. Severity of the abnormal phenotype of transgenic tobacco plants was marked with "+++" for stunting and "++++" for severe stunted phenotype, whereas "–" indicates that no abnormal phenotype was observed. Upper panel, 40-μg protein samples were separated by 10% SDS-PAGE and detected with antibody against full-length RF2a after blotting to nitrocellulose membrane. The band that contains RF2a-ΔPΔA is marked on the right. Lower panel, the membrane used in the immunoblot was stained with Ponceau S (Sigma Chemical Company, St. Louis, Mo.) prior to the antibody reaction.

To confirm that the phenotype was related to transgene expression, protein extracts of the transgenic plants were analyzed via a Western blot assay using an antibody against RF2a. Protein samples from the transgenic leaf tissues were extracted in buffer (50 mM $Na_3PO_4$, pH 7.0, 10 mM EDTA, 0.1% Triton X-100, 0.1% sodium lauryl sarcosine) and quantified using the DC protein assay kit (Bio-Rad Laboratories, Hercules, Calif.). 40 μg of each protein sample was separated via SDS-PAGE and blotted onto nitrocellulose membrane. The membrane was stained with Ponceau S (Sigma Chemical Company, St. Louis, Mo.) to monitor protein loading prior to immuno-detection. The primary antibody used in the immunodetection was raised in rabbits against full-length RF2a; the secondary antibody was horseradish peroxidase-conjugated to goat anti-rabbit antibody (Southern Biotechnology Associates, Inc., Birmingham, Ala.). FIG. 20 shows that there is a direct correlation between the abnormal phenotype and the accumulation of RF2a-ΔPΔA.

Example 12

Versatility of the Gene Regulation System

As shown herein, the acidic domain of RF2a may be linked to any DNA binding domain to regulate the expression of corresponding promoters. More specifically, the novel transcription factors of the present invention that comprise the acidic domain of RF2a (or substantially similar sequences) and at least one DNA binding domain ("DBD"), may be used to regulate the expression of plant functional promoters that comprise one or more cis elements—wherein such elements are capable of interacting with such DNA binding domain. The interaction between such novel transcription factors through such DNA binding domains with corresponding cis elements, preferably, results in the initiation, or enhancement of, transcription.

Similarly, the chimeric promoters of the present invention have been shown to regulate transcription in the presence of RF2a and/or RF2b. More particularly, the inventors have demonstrated that the Box II element and/or its operational derivatives (or substantially similar sequences) may be used in connection with any plant functional promoter to regulate gene expression in the presence of RF2a, RF2b, and/or any novel transcription factor contemplated herein which comprises an amino acid sequence at least substantially similar to the acidic domain of RF2a. Accordingly, it is contemplated that a plurality of different combinations of novel transcription factors and/or novel chimeric promoters of the present invention may be employed to regulate gene expression.

For example, in addition to the Box II element and its operational derivatives described herein, the RF2a and RF2b transcription factors (and related bZIP proteins) have been found to interact with certain additional cis elements to impart regulation of transcription. Non-limiting examples of such additional cis elements are summarized in Table 5 below:

TABLE 5

| Common Name of cis Element | DNA Sequence | SEQ ID NO. |
|---|---|---|
| rbe | CCCCAAAGTCCAGCTTGAAAT | SEQ ID NO:77 |
| G3 | TTAATCCAACTTGGAAAATG | SEQ ID NO:78 |

TABLE 5-continued

| Common Name of cis Element | DNA Sequence | SEQ ID NO. |
|---|---|---|
| AC-II | CCACCACCCCC | SEQ ID NO:79 |
| 4CL-1 | CTTCACCACCCCACT | SEQ ID NO:80 |
| Sh1 | TGGACCCTACCA | SEQ ID NO:81 |
| AHA3 | AGGTCACCCCATT | SEQ ID NO:82 |
| Vs-1 | TGGATGTGGAAGACAGCA | SEQ ID NO:83 |

The present invention contemplates that such additional cis elements, including, without limitation, the elements referenced in Table 5, may be used to construct novel chimeric promoters in accordance with the present invention. Of course, such novel chimeric promoters may be used, for example, to regulate gene expression in connection with RF2a and/or RF2b transcription factors—similar to the chimeric promoters shown and described in previous Examples. It will be appreciated by those skilled in the art that chimeric promoters of the present invention, which comprise, for example, one or more of the additional cis elements listed in Table 5 (or substantially similar sequences), may be constructed and used in a manner similar to that described above with respect to chimeric promoters comprising Box II and/or its operational derivatives.

Still further, the present invention contemplates that the acidic domain of RF2a (SEQ ID NO:6), or substantially similar sequences, may be used with other DNA binding domains in the art. More particularly, the present invention contemplates that the acidic domain of RF2a, or substantially similar sequences, may be linked to any DNA binding domain from a plurality of classes of such domains to create novel transcription factors capable of regulating gene expression (which was demonstrated in Example 10). The invention provides, for example, that the following classes of DNA binding domains may be used in such capacity: (i) basic helix-loop-helix domains ("bHLH"); (ii) DNA binding domains of bZIP proteins; (iii) native or synthetic zinc finger DNA binding domains; and (iv) DNA binding domains of the E2F/DP family of transcription factors. Non-limiting examples of such DNA binding domains for each class are listed in Table 6 below. Additionally, Table 6 references the specific cis element with which such DNA binding domains are known to interact (and affect gene expression).

TABLE 6

| Class of DBD | Representative DBD | Sequence of DBD | cis Element |
|---|---|---|---|
| bHLH | "b/HLH/Z domain of USF" - from *H. Sapiens* | SEQ ID NO. 84 | SEQ ID NO. 85 |
| bZIP | "Jun" - from *H. Sapiens* | SEQ ID NO. 86 | SEQ ID NO. 87 |
| Zinc-Finger | "C2H2" | SEQ ID NO. 88 | SEQ ID NO. 89 |
| E2F/DP | "E2F4" | SEQ ID NO. 90 | SEQ ID NO. 91 |

Many of the DNA binding domains and cognate cis elements referenced in Table 6 are described in the literature (among others). See, for example, Ferre-D'Amare, R. et al. (1994); Toledo-Ortiz, G. et al. (2003); Jakoby, M. et al.

(2002); Segal D. J. et al. (2003); Wolfe, S. A. et al. (2001); Zheng, N. et al. (1999); and Ramirez-Parra, E. et al. (2003).

In light of the foregoing, the present invention contemplates that the DNA binding domains listed in Table 6 may be tethered to the acidic domain of RF2a (SEQ ID NO:6), or to substantially similar sequences, to create novel transcription factors. The methods employed to produce such novel transcription factors may parallel those described above with respect to the transcription factors comprising, for example, the 2C7 domain. Those of skill in the art, however, will appreciate that any number of methods may be used to express such novel transcription factors based on the amino acid sequences described herein.

The novel transcription factors of the present invention, which comprise, for example, one or more DNA binding domains referenced in Table 6 may be used to regulate the expression of appropriately designed chimeric promoters. More particularly, such transcription factors may be used to regulate the expression of chimeric promoters that comprise, for example, the corresponding cis element referenced in Table 6 (or substantially similar sequences). In light of the foregoing, it should be appreciated that the acidic domain of RF2a (or substantially similar sequences) may be linked to any DNA binding domain known in the art (including, without limitation, the domains listed in Table 6) to regulate the expression of corresponding promoters (which contain one or more cis elements that may interact with such DNA binding domain to regulate transcription).

Example 13

Use of Inducible Promoters with the Gene Expression System

The gene expression system of the present invention (including the chimeric promoters, gene expression cassettes, and novel transcription factors described above) may, optionally, be used in connection with a plurality of inducible promoters. In certain preferred embodiments, the present invention is used in connection with chemically-inducible promoters. The following provides a non-limiting example of such embodiments of the present invention.

Plasmid construction—The coding sequence of RF2a was released from a cassette comprising the CaMV 35S promoter operably linked to a RF2a-encoding sequence, p35S::RF2a, through EcoRI/BamHI restriction. The excised DNA fragment was made blunt by Klenow treatment in the presence of dNTPs. The resulting fragment was then cloned into plasmid RH3 (Rohm & Haas, Philadelphia, Pa.) to replace a luciferase coding sequence. The RH3 plasmid originally comprised a luciferase coding sequence downstream of a chimeric promoter that included five (5) repeats of the Gal4 DNA binding site and the CaMV 35S minimal promoter. The chimeric promoter comprising the Gal4 DNA binding sites and the CaMV 35S minimal promoter is set forth in SEQ ID NO: 92.

The RF2a-encoding sequence, together with the chimeric promoter, were released from the resultant plasmid through Sal I/BamHI restriction sites and inserted into vector pSL301, which was previously linearized using the same set of restriction enzymes. The chimeric promoter and RF2a-encoding sequence are referred to herein as the "5G35Sm:RF2a" sequence. The resulting plasmid is identified herein as "pSL-5G35Sm:RF2a."

A DNA fragment containing the uidA gene operably linked to the E fragment of the RTBV promoter was released from pE:GUS through HindIII (blunted)/BamHI restriction. The excised fragment was then inserted upstream of the 5G35Sm:

RF2a sequence in pSL-5G35Sm:RF2a through NdeI (blunted)/BamHI restriction sites (pSL-E:GUS/5G35Sm:RF2a). The sequences encoding E:GUS, together with 5G35Sm:RF2a, were released from pSL-E:GUS/5G35Sm:RF2a through HindIII restriction. The excised fragment was then made blunt using Klenow treatment in the presence of dNTPs.

The excised GUS- and RF2a-encoding fragment was subsequently cloned into the binary vector pCa-5GRbm:DsRed-E5/Cs:VGE, which carried the chimeric receptor gene VGE (SEQ ID NO: 93) under the control of a cassava vein mosaic virus promoter (Cs). The resulting plasmid (pCa-EG2aV) carried the E:GUS, 5G35Sm:RF2a, and Cs:VGE sequences, and was used for *Agrobacterium*-mediated transformation of *Arabidopsis thaliana.*

*Agrobacterium*-mediated transformation—*Arabidopsis* transformation was conducted using the well-known dipping method described in Clough and Bent, 1998. More specifically, *Agrobacterium* GV3101 and pCa-EG2aV were cultured in LB medium and monitored by spectrophotometry. Once the optical density, $OD_{(600)}$, of the culture reached 0.6, the culture was collected via centrifugation. The bacterial cell pellet was re-suspended in 5% sucrose, 0.2% Silwet 77 solution and used for inoculating the flowering *Arabidopsis* plants. The transformed *Arabidopsis* seeds were collected at maturity and sterilized with 70% ethanol. The sterilized seeds were germinated on MS medium containing 50 mg/L of hygromycin B to select transgenic seedlings. The transgenic plants were grown to maturity and seeds were collected, which are referred to as $T_1$ seeds. The $T_1$ seeds were subsequently germinated and grown to maturity.

Induction of RF2a expression—RF2a expression was induced in the transgenic *Arabidopsis* plants described herein by application of a 1:8000 dilution of the pesticide Intrepid® 2F (Dow AgroSciences, Indianapolis, Ind.). The active ingredient in Intrepid® 2F pesticide is methoxyfenozide. The methoxyfenozide compound was found to enhance RF2a expression by interaction with the expressed VGE receptor and chimeric promoter comprising Gal4 DNA binding sites described above. Accordingly, the methoxyfenozide compound served as an expression-inducing ligand, which functioned to enhance expression of the RF2a-encoding sequence. Upon application of the methoxyfenozide compound, RF2a expression was induced, thereby allowing RF2a to interact with the Box II-containing E fragment, which was operably linked to the uidA sequence.

Analysis of GUS activity—The relative GUS activity in the transgenic *Arabidopsis* plants described herein was measured by histochemical analysis. In each of sixty-seven (67) $T_1$ transgenic *Arabidopsis* plants carrying E:GUS, 5G35Sm:RF2a and Cs:VGE, the 1:8000 dilution of Intrepid® 2F described above was applied to one true leaf, while the other leaves in each plant remained untreated. Two-days following the application of the expression-inducing ligand, the treated leaf together with one untreated leaf from the same plant were detached and subjected to GUS staining.

Figure 21:
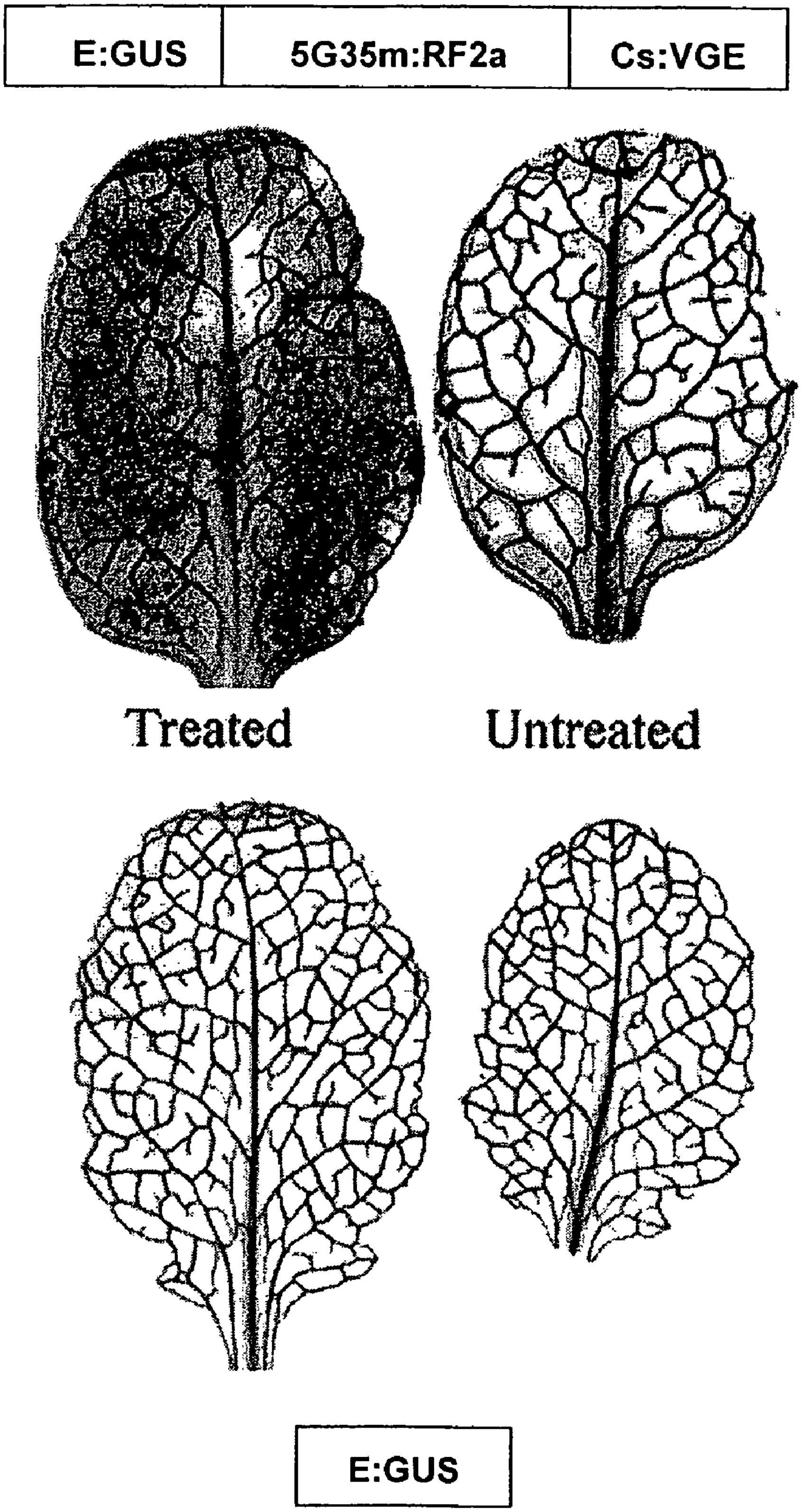
FIG. 21: Activation of GUS expression in non-vascular tissues by induction of RF2a. Leaf tissues from transgenic *Arabidopsis* plants were stained in buffer containing X-Gluc to detect GUS expression. The transgenic *Arabidopsis* plants (shown at the top of FIG. 21) included the E:GUS, 5G35m:RF2a, and Cs:VGE cassettes described herein. "Treated" leaf tissue was subjected to applications of Intrepid® 2F as described herein, whereas "Untreated" leaf tissue was not subjected to Intrepid® 2F. The shaded leaf tissue in the "Treated" leaf correlates with the GUS expression pattern observed. Leaf tissue transformed with only E:GUS is shown at the bottom of FIG. 21.

More particularly, the plant leaf tissues mentioned above were submerged in stain solution containing 1 mM of X-Gluc in 100 mM sodium phosphate buffer (pH 7.0), 2 mM $K_3Fe(CN)_6$, 2 mM $K_4Fe(CN)_6$, 0.1% Triton X-100 and 20% methanol (Petruccelli et al. 2001). In order to evaluate GUS activity, several substrates are available. The most commonly used are 5-bromo-4-chloro-3-indolyl glucuronide (X-Gluc) and 4-methyl-umbelliferyl-glucuronide (MUG). The reaction of GUS with X-Gluc generates a blue color that is useful in histochemical detection of uidA gene activity. uidA activity (GUS expression) is shown in the "Treated" leaf in FIG. 21 by a grey, shaded color (compared to the predominately white, "Untreated" leaf). For quantification purposes, MUG is preferred, because the umbelliferyl radical emits fluorescence under UV stimulation, thus providing better sensitivity and easy measurement by fluorometry.

Following vacuum infiltration of the previously submerged leaf tissues, the tissues were incubated at 37° C. overnight before washing with 70% (v/v) ethanol. In approximately 70% of the sixty-seven (67) plants analyzed, a constitutive GUS expression pattern was observed in the methoxyfenocide-treated leaves. See FIG. 21 for a subjective comparison of GUS expression in "Treated" and "Untreated" leaf tissue.

Quantitative analysis of GUS activity in methoxyfenozide-treated plants was then conducted. $T_2$ generation transgenic *Arabidopsis* plants from twelve $T_1$ primary lines were selected on hygromycin selection medium. The lines are individually referred to herein as EGaV-3, EGaV-5, EGaV-17, EGaV-31, EGaV-50, EGaV-51, EGaV-56, EGaV-59, EGaV-63, EGaV-70, EGaV-72, and E:GUS. For each primary line, eighteen 14-day-old $T_2$ plants were used. Nine plants, in three groups, were cultured in MS hydroponic solution containing a 1:8000 dilution of Intrepid 2F®. The remaining nine plants, in three groups, were left untreated and served as controls. After a three-day treatment period, the GUS activity in leaf tissue samples from each plant was quantified.

Each sample of leaf tissue was ground to a powder in liquid nitrogen. Total protein was extracted from each sample by adding 300 μl of extraction buffer. Protein concentration of each sample was quantified using a Dc Protein Assay Kit (Bio-Rad Laboratories, Hercules, Calif.). GUS activity of each sample was quantified using MUG as substrate and a fluorescence spectrometer (Molecular Devices, Sunnyvale, Calif.) (Petruccelli et al., 2001). Among the twelve lines, the results showed that methoxyfenozide (Intrepid 2F®) treatment induced GUS expression by an average of 2.1 fold in relation to untreated, control plants (FIG. 22A).

Western Blot analysis—To detect the expression of RF2a in select transgenic lines described above, either treated or untreated with Intrepid® 2F, 40 μg of protein of each sample was separated by 12% SDS-PAGE and blotted onto nitrocellulose membrane. The *Arabidopsis* lines analyzed by Western Blot included EGaV50, EGaV59, EGaV63, EGaV70, EGaV72, and E:GUS. Rabbit anti-RF2a antibodies were first applied to the nitrocellulose membrane, incubated, and washed. Next, anti-rabbit horseradish peroxidase-conjugated secondary antibodies were applied to the membrane, incubated, and washed. Finally, SuperSignal substrate (Pierce, Rockford, Ill.) was applied to the membrane, incubated, and washed.

Figure 22:
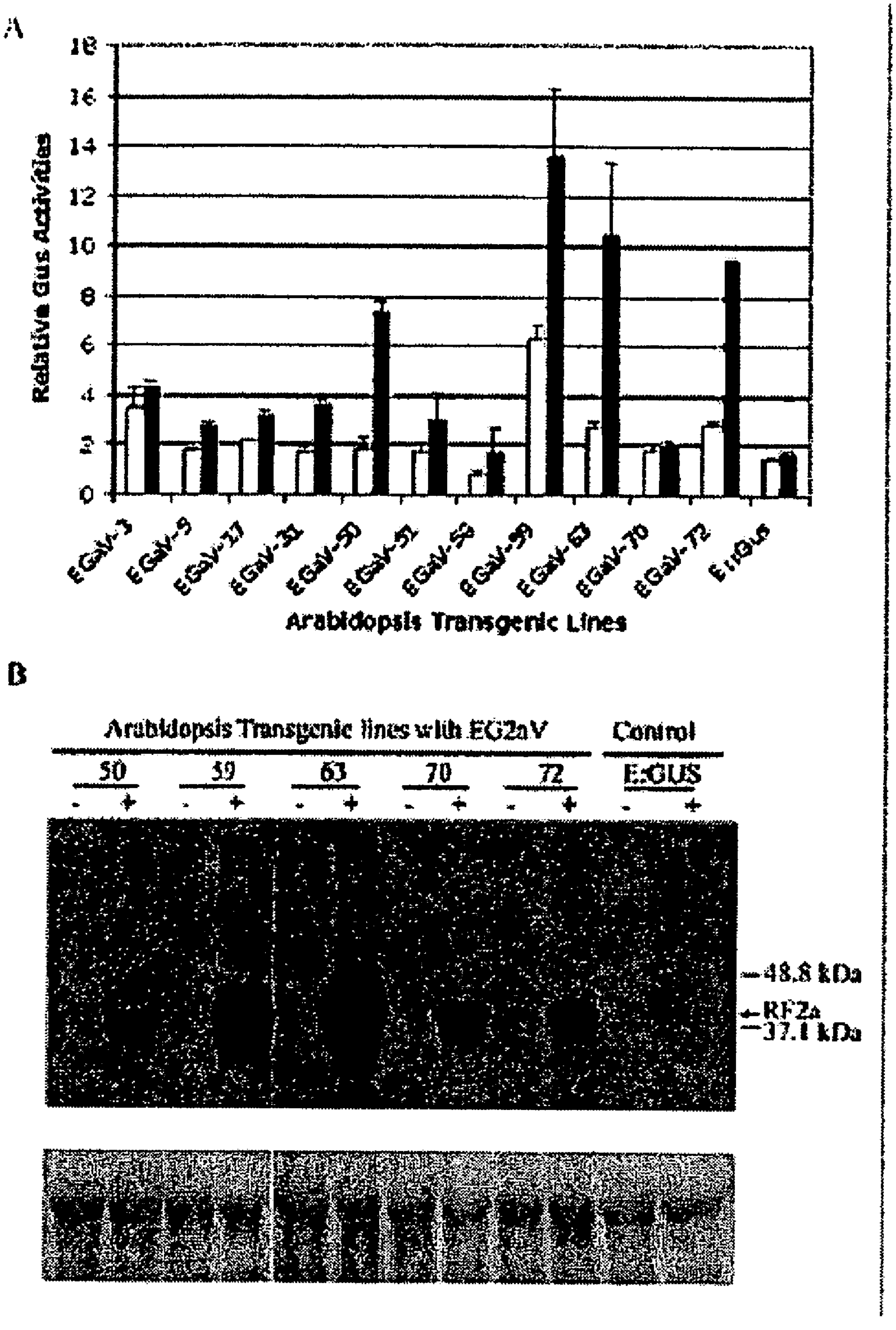
FIG. 22: Quantitative analysis of the activation of the E fragment by RF2a upon chemical induction. A: Relative GUS activity of $T_2$ transgenic *Arabidopsis* plants, which comprise the E:GUS, 5G35Sm:RF2a, and Cs:VGE sequences described herein. Each set of bars represents 1 of 12 groups of transgenic plant lines, namely, EGaV-3, EGaV-5, EGaV-17, EGaV-31, EGaV-50, EGaV-51, EGaV-56, EGaV-59, EGaV-63, EGaV-70, EGaV-72, and E:GUS. Each bar represents the average of three repeats, three plants for each repeat (with standard deviation). Open bars represent control leaf tissue that was not subjected to Intrepid 2F® treatment. Solid bars represent leaf tissue treated with 1:8,000 dilution of Intrepid® 2F. B: Western Blot showing expression of RF2a in a limited number of samples analyzed in FIG. 22A. The lower panel shows the SDS-PAGE gel described below, whereas the upper panel shows the detected RF2a protein on the nitrocellulose membrane. The mark "–" refers to control leaf tissue that was not treated with Intrepid® 2F, whereas "+" refers to leaf tissue that was treated with 1:8,000 dilution of Intrepid® 2F. The RF2a-arrow indicates the band position of the RF2a protein.

After the substrate was applied to the membrane, the RF2a bands were revealed (See FIG. 22B, top panel). The presence of RF2a in the leaf tissue samples that were treated with methoxyfenozide (Intrepid 2F®) correlates with the induction of GUS expression observed in similarly treated leaf tissues (described above).

Example 14

Fragments of the Acidic Domain of RF2a

To further demonstrate the versatility of the present gene expression system and, more particularly, the scope of different peptides encompassed by the novel transcription factors of the invention, fragments of the acidic domain of RF2a were used to construct several novel transcription factors. More specifically, transcription factors comprising residues 49 through 116; 49 through 96; 68 through 116; or 68 through 96 of SEQ ID NO:4 (the full-length RF2a transcription factor) were constructed (35S-A-2C7 (comprising the full acidic domain of RF2a); 35S-A1-2C7; 35S-A2-2C7; and 35S-A3-2C7, respectively).

The foregoing transcription factors further comprised the synthetic 2C7 protein (SEQ ID NO:75)—the synthetic zinc finger DNA-binding domain described above that specifically binds to the 2C7 DNA-binding site (SEQ ID NO:74). The various fragments of the acidic domain of RF2a were fused to the N-terminus of the 2C7 DNA-binding domain. The gene expression cassettes encoding such transcription factors included a CaMV 35S promoter operatively linked to a sequence encoding the respective fragment of the acidic domain, which was operatively linked to a sequence encoding the 2C7 DNA-binding domain (SEQ ID NO:76). The cassettes are referred to in this example collectively or individually as "effector construct."

The various "effector constructs" were prepared using PCR-based procedures and a plasmid (template DNA) containing a coding sequence for the entire RF2a acidic domain (SEQ ID NO: 9) operably linked to a coding sequence (SEQ ID NO: 76) for the 2C7 zinc finger DNA-binding domain (SEQ ID NO: 75). The various fragments of the RF2a acidic domain were amplified from such plasmid using the primer pairs listed in Table 7B below (which are defined in Table 7A).

TABLE 7A

| Primer Name | SEQ ID NO | Location within RF2a/ Restriction Enzyme Site |
|---|---|---|
| A-2C7 5' | SEQ ID NO: 94 | Residue 49/BglII site |
| A-2C7 3' | SEQ ID NO: 95 | Residue 116/BamHI site |
| A68-2C7 5' | SEQ ID NO: 96 | Residue 68/Bg/II |
| A96-2C7 3' | SEQ ID NO: 97 | Residue 96/BamHI site |

TABLE 7B

| Effector Construct | Location within RF2a | 5' Primer | 3' Primer |
|---|---|---|---|
| 35S-A-2C7 | Residues 49-116 | A-2C7 5' | A-2C7 3' |
| 35S-A1-2C7 | Residues 49-96 | A-2C7 5' | A96-2C7 3' |
| 35S-A2-2C7 | Residues 68-116 | A68-2C7 5' | A-2C7 3' |
| 35S-A3-2C7 | Residues 68-96 | A68-2C7 5' | A96-2C7 3' |

The restriction sites listed in Table 7A above, BglII and BamHI, were used to substitute the various fragments of the acidic domain in place of the full acidic domain.

The "reporter construct," C7er2::GUS, carried the uidA coding sequence located downstream of a promoter comprising 6×2C7-binding sites ligated with the minimal promoter of erbB-2 ("er2") (a.k.a. the retinoblastoma minimal promoter). 35S:2C7 encoded the 2C7 protein without an activation domain, i.e., the acidic domain of RF2a or a fragment thereof, and served as a control.

Protoplasts isolated from suspension cultures of BY-2 cells (*Nicotiana tabacum* L., cv. Bright Yellow-2) were transfected via electroporation using procedures well-known in the art. More specifically, the protoplasts were co-transfected with a mixture of DNAs, including 5 μg of reporter construct, 20 μg of a single effector construct (i.e., 35S-A-2C7, 35S-A1-2C7, 35S-A2-2C7, or 35S-A3-2C7), 5 μg of an internal control plasmid comprising a CaMV 35S promoter operatively linked to a GFP-encoding sequence, and 10 μg of herring sperm DNA. The electroporation was conducted using a discharge of 500 μF and 250 V through disposable 0.4 cm cuvettes. Each transient assay was repeated three times per experiment and each experiment was conducted two times.

In addition, electroporation was carried out as described above without effector construct (negative control); without reporter construct (negative control); or, in place of effector construct, 35S-VP16 (a sequence encoding the activation domain of the herpes simplex virus) (positive control).

Quantification of GUS activity in the transfected protoplasts was carried out 24 hours after transfection. More specifically, transfected protoplasts were lysed by freezing and thawing in GUS extraction buffer (pH 7.7), centrifuged, and the supernatants used for GUS enzyme assays. GUS activity was determined by the method of Jefferson et al. (1987). GFP activity was determined by quantifying fluorescence using 490 nm excitation wavelength and 530 nm emission wavelength using a standard fluorometer (Molecular Devices, Sunnyvale, Calif.).

Figure 23:
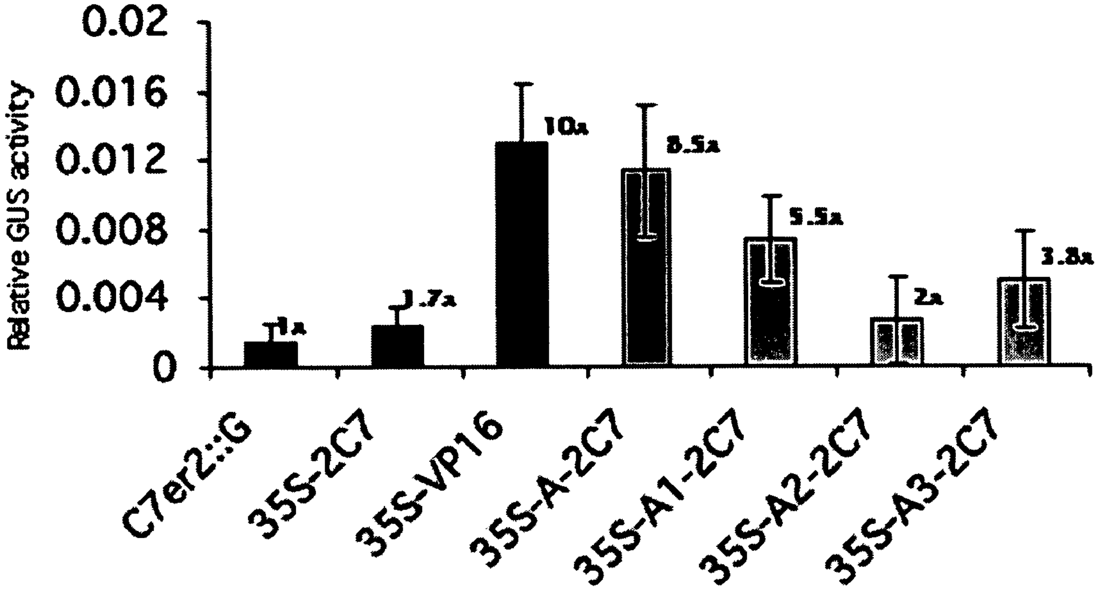
FIG. 23: A bar graph summarizing the expression-enhancing activity of various fragments of the acidic domain of RF2a, as further described in Example 14.
Figure 25:
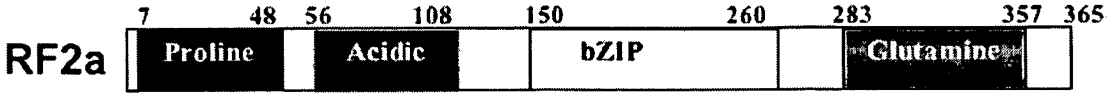
FIG. 25: A diagram of the full-length RF2a protein, showing proline-rich, acidic, bZIP, and glutamine-rich domains.

The relative GUS activity in the BY-2 protoplasts containing reporter and effector construct, as well as the controls described above, is shown in FIG. 23. The results shown in FIG. 23 include GUS enzyme activity compared with GFP activity and are expressed as relative fluorescent units per second. The results are the average of three independent transfections (with standard deviations). The results show that the acidic domain of RF2a is a strong activator of gene expression (35S-A-2C7) and, more specifically, fragments of the acidic domain comprising residues 49-96 of SEQ ID NO:4 (35S-A1-2C7) encompass the majority of such activity.

Example 15

Additional Fragments of the Acidic Domain of RF2a

The results of the previous Example 14 were confirmed in this Example 15 and, furthermore, the activity of two additional fragments of the RF2a acidic domain were measured. The 35S-A-2C7, 35S-A1-2C7, 35S-A2-2C7, and 35S-A3-2C7 effector constructs were prepared as described in Example 14 above. The two additional fragments tested in this Example comprised residues 49-84 (referred to herein as "35S-49/84-2C7") and 56-84 (referred to herein as "35S-56/84-2C7") of the full-length RF2a protein (SEQ ID NO:4). The 35S-56/84-2C7 construct was amplified from the plasmid template described in Example 14 using primer pairs represented by SEQ ID NO:98 and SEQ ID NO:99, whereas the 35S-49/84-2C7 construct was amplified from such plasmid using primer pairs represented by SEQ ID NO:94 and SEQ ID NO:99.

Table 8 below provides a summary of the effector constructs tested in this Example, as well as cross references to the designations given to those effectors described in Example 14 above.

TABLE 8

| Location within RF2a | FIG. 24(B) Reference | Example 14 Reference |
|---|---|---|
| Residues 49-116 | 35S-49/116-2C7 | Effector 35S-A-2C7 |
| Residues 49-96 | 35S-49/96-2C7 | Effector 35S-A1-2C7 |
| Residues 68-116 | 35S-68/116-2C7 | Effector 35S-A2-2C7 |
| Residues 68-96 | 35S-68/96-2C7 | Effector 35S-A3-2C7 |
| Residues 49-84* | 35S-49/84-2C7 | — |
| Residues 56-84* | 35S-56/84-2C7 | — |

*Not shown in the previous Example 14.

The effector constructs identified in Table 8 were electroporated into BY-2 protoplasts as described in Example 14 above (along with the "reporter constructs" described therein), with the exception that a discharge of 125 μF and 300V (through disposable 0.4 cm cuvettes) was used. Each transient assay was repeated three times per experiment and each experiment was conducted three times. Quantification of GUS activity was carried out as described in Example 14 above.

As shown in FIG. 24(B), the results confirm that the acidic domain of RF2a, and certain fragments thereof, represent strong activators of gene expression and, furthermore, that the fragment comprising residues 56-84 (relative to the full RF2a protein) produce an activation effect as strong as the full acidic domain.

Example 16

Expression Activation of the RF2a Acidic Domain in Plants

This Example further demonstrates that the acidic domain of RF2a may be transferred to unrelated proteins (e.g., DNA binding domains) and used to regulate gene expression in plants. In this example, effector constructs were prepared that comprised the CaMV 35S promoter operatively linked to a nucleic acid sequence (SEQ ID NO:9) encoding the acidic domain of RF2a (SEQ ID NO:6), which was operatively linked to a sequence encoding the synthetic 2C7 protein (SEQ ID NO:75). The reporter construct used in this Example included the minimal retinoblastoma promoter erbB, which comprised the 2C7 DNA-binding site (SEQ ID NO:74) (wherein the chimeric promoter is also referred to herein as "C7er"), operably linked to the uidA gene (i.e., GUS-encoding sequence). The control construct used in this Example included the enhanced 35S promoter operably linked to the 2C7 zinc finger protein (without the acidic domain of RF2a or any fragment thereof).

Figure 26:
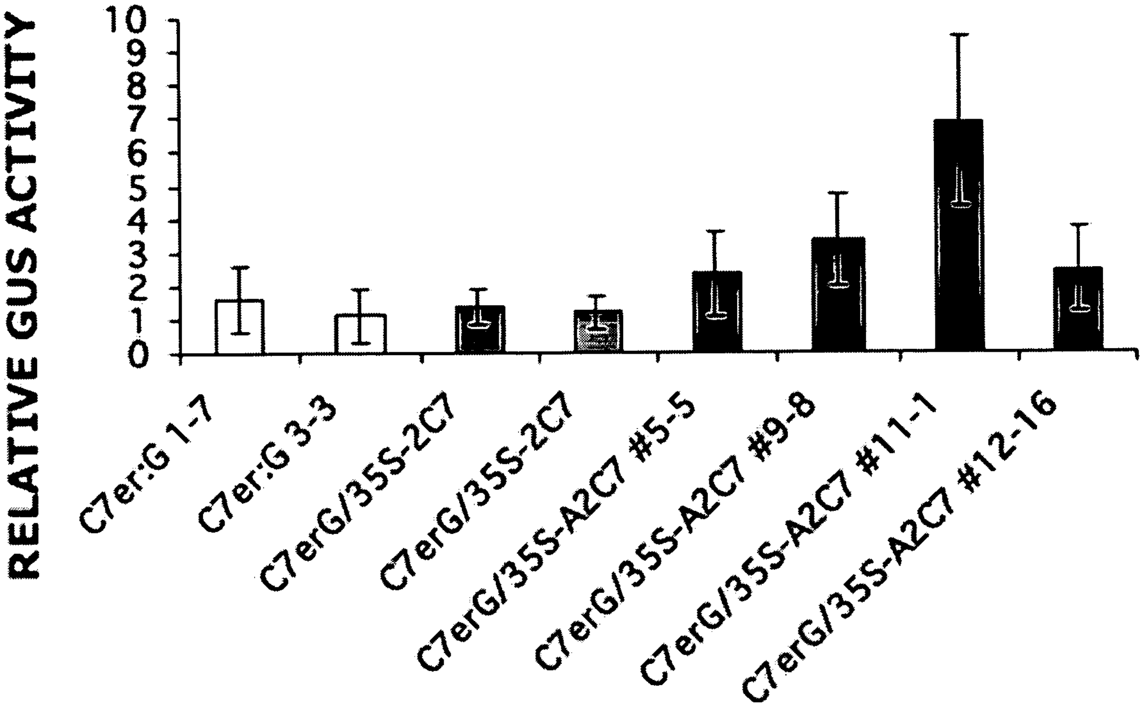
FIG. 26: A bar graph summarizing the expression-enhancing activity of the acidic domain of RF2a in *Arabidopsis thaliana* plants, as further described in Example 16.

The effector constructs are referred to in FIG. 26 as "C7erG/35S-A2C7" followed by the subject plant line, namely, 5-5, 9-8, 11-1, or 12-16. The control constructs are referred to in FIG. 26 as "C7erG/35S-2C7." A second control, including only the reporter construct, is referred to as "C7er:G" (followed by the subject plant line) in FIG. 26.

The foregoing effector, reporter, and/or control constructs were transfected into *Arabidopsis thaliana* plants. More particularly, plasmids containing the effector, reporter, and/or control constructs were transferred by electroporation into *A. tumefaciens* strain GV3101. *Agrobacterium* isolates that contained the respective plasmid were used to transform *A. thaliana* Col-0 by the standard floral dip method (Clough and Bent, 1998). $T_1$ seeds were germinated in Murashige and Skoog medium (Murashige and Skoog, 1962) containing glufosinate ammonium (10 mg/L) and seedlings that survived the selection were grown in soil in a growth chamber. Leaves from six week old plants were collected for GUS expression analysis.

The leaves were homogenized, added to GUS extraction buffer, and subsequently centrifuged. The resulting supernatants were used to determine enzymatic activity by the method of Jefferson et al. (1987). The enzyme activity was determined by quantifying fluorescence using a spectrofluorometer (Spectramax Gemini, Molecular Devices Corp., Sunnyvale, Calif.), with a 365 nm excitation wavelength and 455 nm emission wavelength.

As shown in FIG. 26, the various effector constructs activated and/or enhanced GUS expression in the *A. thaliana* plants (relative to the C7erG/35S-2C7 controls). In addition, FIG. 26 shows that each plant line/effector construct combination produced variable results—albeit all well above the expression levels observed in the C7erG/35S-2C7 controls.

Example 17
RF2a Acidic Domain Fragments/Ecdysone Receptor Fusion Proteins

In this Example, fragments of the RF2a acidic domain and the chimeric VGE receptor (SEQ ID NO:100) were used to create novel transcription factors. More particularly, the chimeric VGE receptor was mutated to replace the "V" domain with (i) the full acidic domain of RF2a, (ii) a minimal acidic domain of RF2a ("A5") (amino acids 56-84 relative to the full RF2a protein) (SEQ ID NO:101), or (iii) a dimer, trimer, or tetramer of the A5 minimal acidic domain (at the N- and C-termini, e.g., to create AGE and GEA proteins). As used herein, the "V" domain of the VGE chimeric receptor refers to the VP16 acidic activation domain of the SV40 animal virus, "G" refers to the DNA binding domain of the Gal4 protein from Bakers yeast, and "E" refers to the ecdysone receptor ("EcR") from *Cloristoneura fumiferana*. The GE domain is represented herein by SEQ ID NO:103 (and encoded by SEQ ID NO:104), while the E domain is represented by SEQ ID NO:105 (and encoded by SEQ ID NO:106).

FIG. 27(A) provides a diagram of the various "effector" constructs used in this Example (with the exception of the constructs comprising a full RF2a acidic domain). As shown therein, the effector constructs included the CsVMV promoter (SEQ ID NO:67) operably linked to (i) a sequence encoding the full VGE protein (the positive control), (ii) a sequence encoding A5 operably linked to a sequence encoding GE (oriented to express A5 at the N-terminus ("A5GE") or C-terminus ("GEA5"), (iii) a sequence encoding an A5 dimer operably linked to a sequence encoding GE (oriented to express the A5 dimer at the N-terminus ("A5×2GE") or C-terminus ("GEA5×2"), (iv) a sequence encoding an A5 trimer operably linked to a sequence encoding GE (oriented to express the A5 trimer at the N-terminus ("A5×3GE") or C-terminus ("GEA5×3"), and (v) a sequence encoding an A5 tetramer operably linked to a sequence encoding GE (oriented to express the A5 tetramer at the C-terminus ("GEA5×4"). The foregoing effector constructs were prepared using standard DNA cloning and PCR procedures, along with plasmids containing sequences encoding the full length RF2a acidic domain (SEQ ID NO:6) and VGE (SEQ ID NO:100). Those of ordinary skill in the art will appreciate, however, that such effector sequences (and derivatives thereof) may also be constructed synthetically using standard procedures.

Table 9 below provides a summary of the various effector constructs, and the amino acid sequences thereof (from the N- to C-terminus), analyzed in this Example.

TABLE 9

| Construct (FIG. 27) | Promoter | Novel Transcription Factor Sequence | Termination Sequence |
|---|---|---|---|
| VGE | CsVMV | SEQ ID NO: 107 (V) + SEQ ID NO: 103 (GE) | Nos |
| AGE | CsVMV | SEQ ID NO: 6 (A) + SEQ ID NO: 103 (GE) | Nos |
| A5GE | CsVMV | SEQ ID NO: 101 (A5) + SEQ ID NO: 103 (GE) | Nos |
| A5 × 2GE | CsVMV | (2 × SEQ ID NO: 101 (A5)) + SEQ ID NO: 103 (GE) | Nos |
| A5 × 3GE | CsVMV | (3 × SEQ ID NO: 101 (A5)) + SEQ ID NO: 103 (GE) | Nos |
| GEA | CsVMV | SEQ ID NO: 103 (GE) + SEQ ID NO: 6 (A) | Nos |
| GEA5 | CsVMV | SEQ ID NO: 103 (GE) + SEQ ID NO: 101 (A5) | Nos |
| GEA5 × 2 | CsVMV | SEQ ID NO: 103 (GE) + (2 × SEQ ID NO: 101 (A5)) | Nos |
| GEA5 × 3 | CsVMV | SEQ ID NO: 103 (GE) + (3 × SEQ ID NO: 101 (A5)) | Nos |
| GEA5 × 4 | CsVMV | SEQ ID NO: 103 (GE) + (4 × SEQ ID NO: 101 (A5)) | Nos |

FIG. 27(A) further shows a diagram of the reporter construct, namely, 5XG-35S:GUS, which was transformed into BY-2 protoplasts along with the effector constructs. As used herein, "5XG" is represented by SEQ ID NO:108 and refers to a pentameric tandem repeat of the nucleic acid sequence that is recognized by, and binds with, the Gal4 protein/domain (from Bakers yeast) (SEQ ID NO:107). "35S" refers to the minimal CaMV 35S promoter (−45/+8). Of course, the GUS-encoding uidA sequence was operably linked to the CaMV 35S promoter.

Protoplasts were co-transfected, by electroporation as described in Example 14 above, with 5 μg of reporter construct DNA, 20 μg of a single effector construct, 5 μg of a 35S-GFP plasmid, and 10 μg of herring sperm DNA. Methoxyfenozide ("MOF") was provided to the transformed protoplasts at a final dilution of 1:25,000 (providing a 2.452 μM final concentration of MOF). Quantification of GUS activity from protoplast extracts 24 hours after transfection was performed.

The results of such quantification are shown in FIG. 27(B), which are expressed as the amount of GUS enzyme activity compared with GFP activity—expressed as relative fluorescent units per second. The results are the average of three independent transfections+/−standard deviation. The presence of MOF is represented in FIG. 27(B) by "+I" (wherein "I" means Inducer), whereas the absence of MOF is represented by "−I". For example, "AGE+I" represents protoplasts transfected with the AGE effector construct and cultured in the presence of MOF, whereas "AGE−I" represents protoplasts transfected with the AGE effector construct and cultured in the absence of MOF.

As shown in FIG. 27(B), the fusion of the acidic domain of RF2a at the amino-terminal position of GE activates GUS expression in the presence of the MOF inducer. Although the activation provided by the RF2a acidic domain (and fragments thereof) was not as strong as that of VP16, those skilled in the art will appreciate that the RF2a acidic domain (and fragments thereof) produced a level of activation that is, at least, comparable to that of VP16 (and induced less background).

In addition, as shown in FIG. 27(B), the presence of two tandem repeats of A5 had an activation effect as strong as the full acidic domain. Furthermore, as shown in FIG. 27(B), proteins having the RF2a acidic domain (or fragment thereof) at the N-terminus (e.g., AGE proteins) were shown to be more active than proteins having the RF2a acidic domain (or fragment thereof) at the C-terminus (e.g., GEA proteins).

Example 18

RF2a Acidic Domain/Ecdysone Receptor Fusion Proteins in Plants

Figure 28:
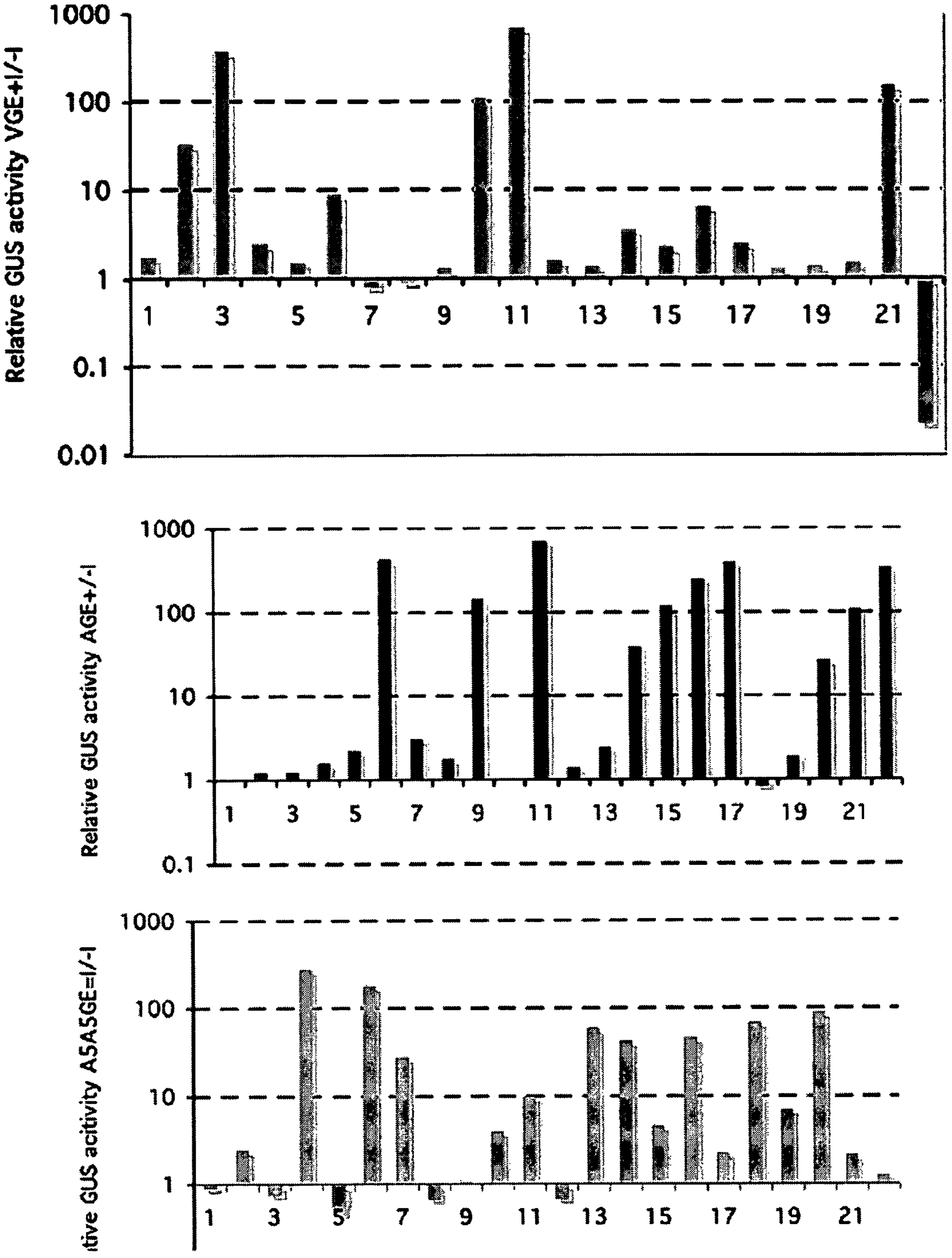
FIG. 28: Analysis of $T_1$ generation *Arabidopsis thaliana* plants transformed with VGE, AGE, or A5A5GE (and GUS reporter) constructs, as further described in Example 18 below. Top: A bar graph showing the relative GUS activity produced by the various VGE constructs. Middle: A bar graph showing the relative GUS activity produced by the various AGE constructs. Bottom: A bar graph showing the relative GUS activity produced by the various A5A5GE constructs.

In this Example, *Arabidopsis thaliana* Col-0 plants were transformed with *A. tumefaciens* bacterium (strain GV3101) containing effector constructs comprising the CsVMV promoter operably linked to a nucleic acid sequence (SEQ ID NO:104) encoding the GE protein, plus (i) a nucleic acid sequence encoding the VP16 acidic activation domain of the herpes simplex virus, (ii) a sequence (SEQ ID NO:9) encoding the full RF2a acidic domain, or (iii) a sequence (2×SEQ ID NO:102) encoding a dimer of the A5 minimal acidic domain of RF2a ("A5A5"). The foregoing VP16 acidic domain-, RF2a acidic domain-, and A5A5 domain-encoding sequences were oriented to express such domains at the N-terminal of the GE protein. FIG. 28 refers to these constructs as VGE, AGE, and A5A5GE, respectively.

The foregoing effector constructs were prepared using standard DNA cloning and PCR procedures, and plasmids containing nucleic acid sequences encoding the VP16 acidic domain, the full length RF2a acidic domain (SEQ ID NO:6), the A5A5 domain (2×SEQ ID NO:101), and the GE domain (SEQ ID NO:103). Those of ordinary skill in the art will appreciate, however, that such effector sequences (and derivatives thereof) may also be constructed synthetically using standard procedures. The reporter construct described in Example 17 above, 5XG-35S:GUS, was used in this Example.

Table 10 below provides a summary of the various effector constructs, and the amino acid sequences thereof (from the N- to C-terminus), analyzed in this Example.

TABLE 10

| Construct (FIG. 27) | Promoter | Novel Transcription Factor Sequence | Termination Sequence |
|---|---|---|---|
| VGE | CsVMV | SEQ ID NO: 100 | Nos |
| AGE | CsVMV | SEQ ID NO: 6 (A) + SEQ ID NO: 103 (GE) | Nos |
| A5A5GE | CsVMV | (2 × SEQ ID NO: 101 (A5)) + SEQ ID NO: 103 (GE) | Nos |

Next, plasmids containing the effector and reporter constructs described above were transferred by electroporation into *A. tumefaciens* strain GV3101. *Agrobacterium* isolates that contained the respective plasmids were used to transform *A. thaliana* Col-0 using a standard floral dip method (Clough and Bent, 1998). Seeds from the $T_1$ generation were collected and germinated in Murashige and Skoog medium (Murashige and Skoog, 1962) containing a selective component (hygromycin B (30 μg/mL).

The seedlings that survived the selection were grown in soil in a growth chamber and allowed to self-fertilize. Next, $T_2$ generation seeds were collected and germinated in Murashige and Skoog medium, which contained hygromycin B (30 μg/mL). The seedlings that survived the selection in a 3:1 segregation pattern were grown in soil in a growth chamber (under 12 hours of light/12 hours of dark per day, at 22° C., 50% humidity).

Analysis of $T_1$ Generation Plants—In this Example, 22 $T_1$ plants were analyzed for methoxyfenozide (MOF) induced gene expression. More particularly, leaf samples from each of the 22 plants were taken before and after induction with MOF (MOF was applied by drenching the soil with a 1:10,000 dilution of MOF (61.3 μM of MOF) for 60 hours). The leaves were homogenized and added to GUS extraction buffer. The supernatants were analyzed for GUS enzymatic activity as described in Example 16 above.

FIG. 28 shows the relative GUS activity of each plant grown in the presence of MOF compared to the relative GUS activity of each plant grown in the absence of MOF. As shown in FIG. 28, the fusion of the acidic domain of RF2a to the amino-terminal position of the GE protein ("AGE"; middle graph), or the presence of two tandem repeats of A5 ("A5A5GE"; bottom graph), activated GUS expression in the presence of the MOF inducer as strong as VP16 ("VGE"; top graph).

Figure 29:
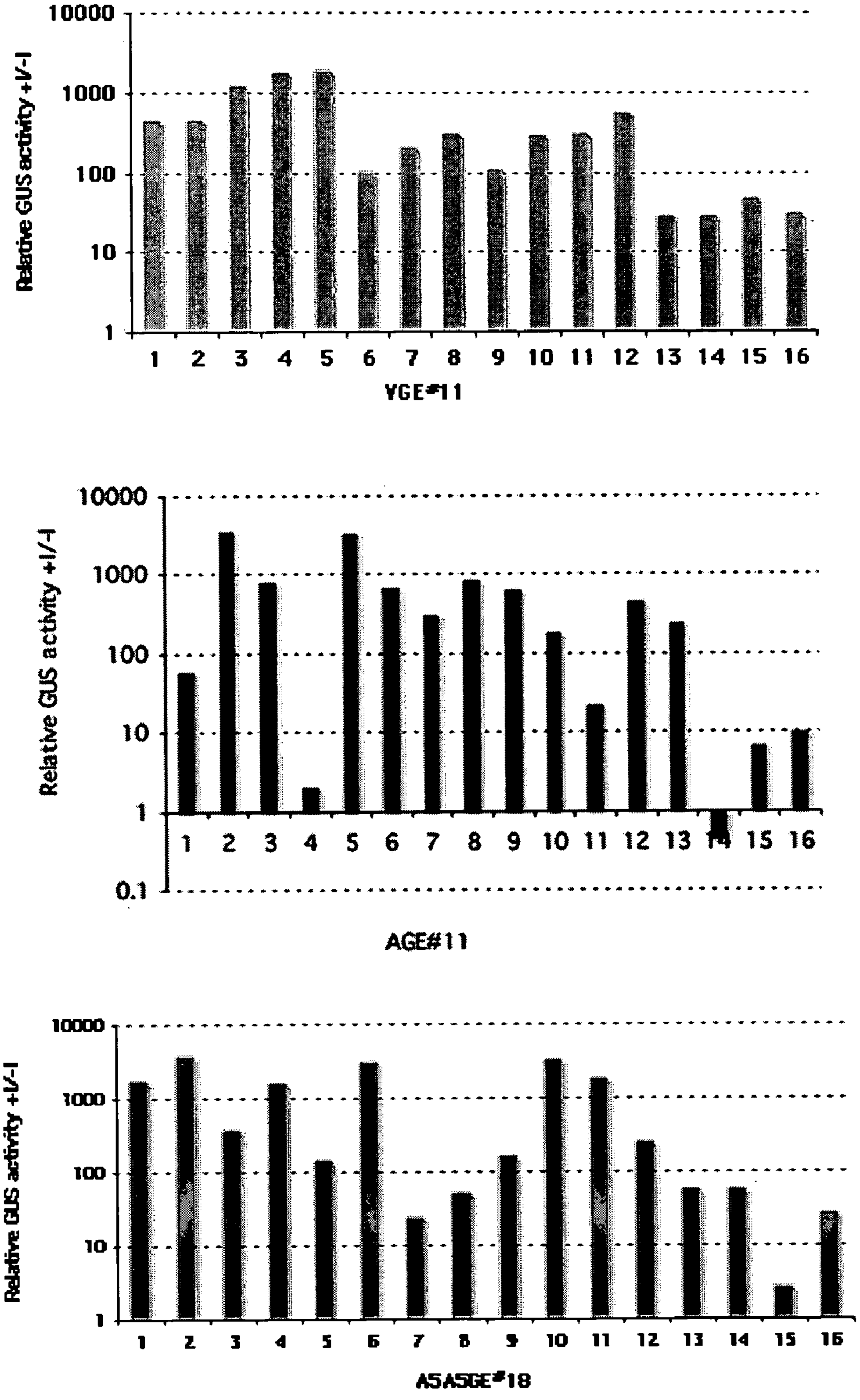
FIG. 29: Analysis of $T_2$ generation *Arabidopsis thaliana* plants transformed with VGE, AGE, or A5A5GE (and GUS reporter) constructs, as further described in Example 18 below. Top: A bar graph showing the relative GUS activity produced by the various VGE constructs. Middle: A bar graph showing the relative GUS activity produced by the various AGE constructs. Bottom: A bar graph showing the relative GUS activity produced by the various A5A5GE constructs.

Analysis of $T_2$ Generation Plants—A total of 16 different plants from a $T_2$ generation plant line (having a segregation of the reporter/effector constructs of 3:1), wherein each plant contained a VGE, AGE, or A5A5GE effector construct, were induced with MOF and analyzed for GUS activity (as described above). Referring to FIG. 29, the VGE construct was tested using plant line #11, the AGE construct was tested using plant line #11, and the A5A5GE construct was tested using plant line #18. As shown in FIG. 29, the fusion of the acidic domain of RF2a to the amino-terminal position of the GE protein ("AGE"; middle graph), or the presence of two tandem repeats of A5 ("A5A5GE"; bottom graph), activated GUS expression (in the $T_2$ generation plants) in the presence of the MOF inducer as strong as VP16 ("VGE"; top graph).

The many aspects and benefits of the invention are apparent from the detailed description, and thus, it is intended for the following claims to cover all such aspects and benefits of the invention which fall within the scope and spirit of the invention. In addition, because numerous modifications and variations will readily occur to those skilled in the art, the claims should not be construed to limit the invention to the exact construction and operation illustrated and described herein. Accordingly, all suitable modifications and equivalents should be understood to fall within the scope of the invention as claimed herein.

REFERENCES

Christopherson, K. S., Mark, M. R., Bajaj, V. and Godowski, P. J. (1992). Ecdysteroid-dependent regulation of genes in mammalian cells by a *Drosophila* ecdysone receptor and chimeric transactivators. *Proc. Natl. Acad. Sci. U.S.A.* 89, 6314-6318.

Clough, S. J. and Bent, A. F. (1998). Floral dip: a simplified method for *Agrobacterium*-mediated transformation of *Arabidopsis thaliana*. *Plant J.* 16, 735-743.

Ferre-D'Amare, R., Pognonec, P., Roeder, R. G., and Burley, S. K. (1994). Structure and function of the b/HLH/Z domain of USF. *EMBO J.* 13(1), 180-189.

Fujii, Y., Shimizu, T., Toda, T., Yanagida, M. and Hakoshima, T. (2000). Structural basis for the diversity of DNA recognition by bZIP transcription factors. *Nat Struct Biol* 7, 889-93.

Fukazawa, J., Sakai, T., Ishida, S., Yamaguchi, I., Kamiya, Y. and Takahashi, Y. (2000). Repression of shoot growth, a bZIP transcriptional activator, regulates cell elongation by controlling the level of gibberellins. *Plant Cell* 12, 901-15.

Gatz, C., Frohberg, C. and Wendenburg, R. (1992) Stringent repression and homogeneous de-repression by tetracycline of a modified CaMV 35S promoter in intact transgenic tobacco plants. *Plant J.* 2, 397-404.

Giniger, E., Varnum, S. M. and Ptashne, M. (1985). Specific DNA binding of GAL4, a positive regulatory protein of yeast. *Cell* 40, 767-74.

He, X., Hohn, T. and Futterer, J. (2000). Transcriptional activation of the rice tungro bacilliform virus gene is critically dependent on an activator element located immediately upstream of the TATA box. *J. Biol. Chem.* 275, 11799-808.

Horsch, R. B., Fry, J., Hoffmann, N., Neidermeyer, J., Rogers, S. G. and Fraley, R. T. (1988). in *Plant Molecular Biology Manual*, eds. Gelvin, S. B. & Schilperoort, R. A. (Kluwer, Dordrecht, The Netherlands), p. A5, 1-9.

Jakoby, M., Weisshaar, B., Droge-Laser, W., Vicente-Carbajosa, J., Tiedemann, J., Kroj, T., and Parcy, F. (2002). bZIP transcription factors in *Arabidopsis. Trends Plant Sci.* 7, 106-111.

Jefferson, R. A., Kavanagh, T. A., and Bevan, M. W. (1987). GUS fusions: beta-glucuronidase as a sensitive and versatile gene fusion marker in higher plants, *EMBO J.* 6, 3901-07.

Klemm, R. D., Goodrich, J. A., Zhou, S. and Tjian, R. (1995). Molecular cloning and expression of the 32-kDa subunit of human TFIID reveals interactions with VP16 and TFIIB that mediate transcriptional activation. *Proc. Natl. Acad. Sci. U.S.A.* 92, 5788-92.

Liu, Q., Segal, D. J., Ghiara, J. B., and Barbas, C. F., III. (1997) *Proc. Natl. Acad. Sci. U.S.A.* 94, 5525-30.

Martinez, A., Sparks, C., Hart, C. A., Thompson, J. and Jepson, I. (1999). Ecdysone agonist inducible transcription in transgenic tobacco plants. *Plant J.* 19, 97-106.

Meshi, T. and Iwabuchi, M. (1995). Plant transcription factors. *Plant Cell Physiol.* 36, 1405-20.

Mitchell, P. J. and Tjian, R. (1989). Transcriptional regulation in mammalian cells by sequence-specific DNA binding proteins. *Science* 245, 371-78.

Murashige, T. and Skoog, F. (1962). Revised medium for rapid growth and bioassays with tobacco tissue cultures. *Physiol. Plantarum* 15, 473-497.

Ordiz, M. I., Barbas, C. F., III, and Beachy, R. N. (2003) *Proc. Natl. Acad. Sci. U.S.A.* 99, 13290-95.

Padidam, M., Gore, M., Lu, D. L., and Smirnova, O. (2003). Chemical-inducible, ecdysone receptor-based gene expression system for plants. *Transgenic Res.* 12, 101-109.

Petruccelli, S., Dai, S., Carcamo, R., Yin, Y., Chen, S. and Beachy, R. N. (2001). Transcription factor RF2a alters expression of the rice tungro bacilliform virus promoter in transgenic tobacco plants. *Proc. Natl. Acad. Sci. U.S.A.* 98, 7635-40.

Pugh, B. F. (2000). Control of gene expression through regulation of the TATA-binding protein. *Gene* 255, 1-14.

Ramirez-Parra, E., Frundt, C., and Gutierrez, C. (2003). A genome-wide identification of E2F-regulated genes in *Arabidopsis. The Plant J.* 33, 801-11.

Ringli, C. and Keller, B. (1998). Specific interaction of the tomato bZIP transcription factor VSF-1 with a non-palindromic DNA sequence that controls vascular gene expression. *Plant Mol. Biol.* 37, 977-88.

Segal, D. J., Stege J. T., and Barbas C. F. (2003). Zinc fingers and a green thumb: manipulating gene expression in plants. *Curr. Opin. Plant Biol.* 6, 163-68.

Stargell, L. A. and Struhl, K. (1995) *Science* 269, 75-78.

Toledo-Ortiz, G., Huq, E., and Quail, P. H. (2003). The *Arabidopsis* Basic/Helix-Loop-Helix Transcription Factor Family, *The Plant Cell* 15, 1749-70.

Truant, R., Xiao, H., Ingles, C. J., and Greenblatt, J. (1993) *J. Biol. Chem.* 268, 2284-87.

Uesugi, M., Nyanguile, O., Lu, H., Levine, A. J., and Verdine, G. L. (1997) *Science* 277, 1310-13.

Watanabe, Y., Meshi, T. and Okada, Y. (1987). Infection of tobacco protoplasts with in vitro transcribed tobacco mosaic-virus RNA using an improved electroporation method. *FEBS LETTERS* 219, 65-69.

Weinmann, P., Gossen, M., Hillen, W., Bujard, H. and Gatz, C. (1994). A chimeric transactivator allows tetracycline-responsive gene expression in whole plants. *Plant J.* 5, 559-69.

Wolfe, S. A., Grant, R. A., Elrod-Erickson, M. and Pabo, C. O. (2001). Beyond the 'recognition code': structures of two Cys2His2 zinc finger/TATA box complexes. *Structure* 9, 717-23.

Yin, Y. and Beachy, R. N. (1995). The regulatory regions of the rice tungro bacilliform virus promoter and interacting nuclear factors in rice (*Oryza sativa* L.). *Plant J.* 7, 969-80.

Yin, Y., Chen, L. and Beachy, R. (1997). Promoter elements required for phloem-specific gene expression from the RTBV promoter in rice. *Plant J.* 12, 1179-88.

Yin, Y., Zhu, Q., Dai, S., Lamb, C., and Beachy, R. N. (1997). RF2a, a bZIP transcriptional activator of the phloem-specific rice tungro bacilliform virus promoter, functions in vascular development. *EMBO J.* 16, 5247-59.

Zheng, N., Fraenkel, E., Pabo, C. O., and Pavletich, N. P. (1999). Structural basis of DNA recognition by the heterodimeric cell cycle transcription. *Genes Dev.* 13, 666-74.

What is claimed is:

1. A protein capable of regulating the expression level of at least one gene of interest, which comprises:

(i) an amino acid sequence consisting of SEQ ID NO:6; and (ii) a DNA binding domain selected from the group consisting of a 2C7 DNA binding domain and a GAL4 DNA binding domain, wherein the DNA binding domain is capable of recognizing and binding to a nucleic acid sequence, wherein the nucleic acid sequence is capable of regulating the expression level of at least one gene of interest.

2. The protein of claim 1, wherein the nucleic acid sequence is a promoter.

3. The protein of claim 1, which further comprises an ecdysone receptor domain.

4. The protein of claim 3, wherein the ecdysone receptor domain comprises an amino acid of SEQ ID NO:105.

5. The protein of claim 4, wherein the nucleic acid sequence comprises a Gal4 binding domain, which comprises a nucleic acid sequence of SEQ ID NO:108.

6. The protein of claim 1, wherein the nucleic acid sequence comprises a C7er domain, which comprises a sequence of SEQ ID NO:74.

7. A protein capable of regulating the expression level of at least one gene of interest, which comprises:

(i) an amino acid sequence that comprises SEQ ID NO:101; and (ii) a DNA binding domain selected from the group consisting of a 2C7 DNA binding domain and a GAL4 DNA binding domain, wherein the DNA binding domain is capable of recognizing and binding to a nucleic acid sequence, wherein the nucleic acid sequence is capable of regulating the expression level of at least one gene of interest.

8. The protein of claim 7, wherein the nucleic acid sequence is a promoter.

9. The protein of claim 8, which further comprises an ecdysone receptor domain.

10. The protein of claim 9, wherein the ecdysone receptor domain comprises an amino acid sequence of SEQ ID NO:105.

11. The protein of claim 8, which further comprises a 2C7 zinc finger domain.

12. The protein of claim 11, wherein the promoter comprises a C7er domain, which comprises a nucleic acid sequence of SEQ ID NO:74.

13. The protein of claim 7, which comprises two or more repetitions of SEQ ID NO:101.

14. A protein capable of regulating the expression level of at least one gene of interest, which comprises:

(i) an amino acid sequence represented by SEQ ID NO:6 or a fragment thereof which consists of SEQ ID NO:101;

(ii) an ecdysone receptor domain; and (iii) a Gal4 protein.

* * * * *

SEQUENCE LISTING

```
<160> NUMBER OF SEQ ID NOS: 109

<210> SEQ ID NO 1
<211> LENGTH: 15
<212> TYPE: DNA
<213> ORGANISM: Artificial
<220> FEATURE:
<223> OTHER INFORMATION: This sequence was artificially derived and/or
      created by the inventors.
```

<400> SEQUENCE: 1
ccagtgtgcc cctgg 15

<210> SEQ ID NO 2
<211> LENGTH: 15
<212> TYPE: DNA
<213> ORGANISM: Artificial
<220> FEATURE:
<223> OTHER INFORMATION: This sequence was artificially derived and/or created by the inventors.

<400> SEQUENCE: 2
ccagtgtggc gctgg 15

<210> SEQ ID NO 3
<211> LENGTH: 15
<212> TYPE: DNA
<213> ORGANISM: Artificial
<220> FEATURE:
<223> OTHER INFORMATION: This sequence was artificially derived and/or created by the inventors.

<400> SEQUENCE: 3
ggagtgtgcc ccttc 15

<210> SEQ ID NO 4
<211> LENGTH: 368
<212> TYPE: PRT
<213> ORGANISM: Artificial
<220> FEATURE:
<223> OTHER INFORMATION: This sequence was artificially derived and/or created by the inventors.

<400> SEQUENCE: 4

```
Met Asn Arg Glu Lys Ser Pro Ile Pro Gly Asp Gly Gly Asp Gly Leu
1               5                   10                  15

Pro Pro Gln Ala Thr Arg Arg Ala Gly Pro Pro Ala Ala Ala Ala Ala
            20                  25                  30

Ala Glu Tyr Asp Ile Ser Arg Met Pro Asp Phe Pro Thr Arg Asn Pro
        35                  40                  45

Gly His Arg Arg Ala His Ser Glu Ile Leu Ser Leu Pro Glu Asp Leu
    50                  55                  60

Asp Leu Cys Ala Ala Gly Gly Gly Asp Gly Pro Ser Leu Ser Asp Glu
65                  70                  75                  80

Asn Asp Glu Glu Leu Phe Ser Met Phe Leu Asp Val Glu Lys Leu Asn
                85                  90                  95

Ser Thr Cys Gly Ala Ser Ser Glu Ala Glu Ala Glu Ser Ser Ser Ala
            100                 105                 110

Ala Ala His Gly Ala Arg Pro Lys His Gln His Ser Leu Ser Met Asp
        115                 120                 125

Glu Ser Met Ser Ile Lys Ala Glu Glu Leu Val Gly Ala Ser Pro Gly
    130                 135                 140

Thr Glu Gly Met Ser Ser Ala Glu Ala Lys Lys Ala Val Ser Ala Val
145                 150                 155                 160

Lys Leu Ala Glu Leu Ala Leu Val Asp Pro Lys Arg Ala Lys Arg Ile
                165                 170                 175

Trp Ala Asn Arg Gln Ser Ala Ala Arg Ser Lys Glu Arg Lys Met Arg
            180                 185                 190

Tyr Ile Ala Glu Leu Glu Arg Lys Val Gln Thr Leu Gln Thr Glu Ala
```

-continued

```
        195                 200                 205

Thr Thr Leu Ser Ala Gln Leu Ala Leu Leu Gln Arg Asp Thr Ser Gly
    210                 215                 220

Leu Thr Thr Glu Asn Ser Glu Leu Lys Leu Arg Leu Gln Thr Met Glu
225                 230                 235                 240

Gln Gln Val His Leu Gln Asp Ala Leu Asn Asp Thr Leu Lys Ser Glu
                245                 250                 255

Val Gln Arg Leu Lys Val Ala Thr Gly Gln Met Ala Asn Gly Gly Gly
            260                 265                 270

Met Met Met Asn Phe Gly Gly Met Pro His Gln Phe Gly Gly Asn Gln
        275                 280                 285

Gln Met Phe Gln Asn Asn Gln Ala Met Gln Ser Met Leu Ala Ala His
    290                 295                 300

Gln Leu Gln Gln Leu Gln Leu His Pro Gln Ala Gln Gln Gln Gln Val
305                 310                 315                 320

Leu His Pro Gln His Gln Gln Gln Gln Pro Leu His Pro Leu Gln Ala
                325                 330                 335

Gln Gln Leu Gln Gln Ala Ala Arg Asp Leu Lys Met Lys Ser Pro Met
            340                 345                 350

Gly Gly Gln Ser Gln Trp Gly Asp Gly Lys Ser Gly Ser Ser Gly Asn
        355                 360                 365


<210> SEQ ID NO 5
<211> LENGTH: 329
<212> TYPE: PRT
<213> ORGANISM: Artificial
<220> FEATURE:
<223> OTHER INFORMATION: This sequence was artificially derived and/or
      created by the inventors.

<400> SEQUENCE: 5

Met Gln Glu Pro Lys His Thr Asp Pro Ala Ala Met Arg Gly Ala His
1               5                   10                  15

His Arg Arg Ala Arg Ser Glu Val Ala Phe Arg Leu Pro Asp Asp Leu
            20                  25                  30

Asp Leu Gly Gly Gly Gly Ala Gly Ala Phe Asp Glu Ile Gly Ser Glu
        35                  40                  45

Asp Asp Leu Phe Ser Thr Phe Met Asp Ile Glu Lys Ile Ser Ser Gly
    50                  55                  60

Pro Ala Ala Ala Gly Gly Ser Asp Arg Asp Arg Ala Ala Glu Thr Ser
65                  70                  75                  80

Ser Pro Pro Arg Pro Lys His Arg His Ser Ser Ser Val Asp Gly Ser
                85                  90                  95

Gly Phe Phe Ala Ala Ala Arg Lys Asp Ala Ala Ala Ser Leu Ala Glu
            100                 105                 110

Val Met Glu Ala Lys Lys Ala Met Thr Pro Glu Gln Leu Ser Asp Leu
        115                 120                 125

Ala Ala Ile Asp Pro Lys Arg Ala Lys Arg Ile Leu Ala Asn Arg Gln
    130                 135                 140

Ser Ala Ala Arg Ser Lys Glu Arg Lys Ala Arg Tyr Ile Thr Glu Leu
145                 150                 155                 160

Glu Arg Lys Val Gln Thr Leu Gln Thr Glu Ala Thr Thr Leu Ser Ala
                165                 170                 175

Gln Leu Thr Leu Phe Gln Arg Asp Thr Thr Gly Leu Ser Ala Glu Asn
            180                 185                 190
```

-continued

```
Ala Glu Leu Lys Ile Arg Leu Gln Ala Met Glu Gln Gln Ala Gln Leu
        195                 200                 205

Arg Asp Ala Leu Asn Asp Ala Leu Lys Gln Glu Leu Glu Arg Leu Lys
    210                 215                 220

Leu Ala Thr Gly Glu Met Thr Asn Ser Asn Glu Thr Tyr Ser Met Gly
225                 230                 235                 240

Leu Gln His Val Pro Tyr Asn Thr Pro Phe Phe Pro Leu Ala Gln His
                245                 250                 255

Asn Ala Ala Arg Gln Asn Gly Gly Thr Gln Leu Pro Pro Gln Phe Gln
            260                 265                 270

Pro Pro Arg Pro Asn Val Pro Asn His Met Leu Ser His Pro Asn Gly
        275                 280                 285

Leu Gln Asp Ile Met Gln Gln Asp Pro Leu Gly Arg Leu Gln Gly Leu
    290                 295                 300

Asp Ile Ser Lys Gly Pro Leu Val Val Lys Ser Glu Ser Ser Ser Ile
305                 310                 315                 320

Ser Ala Ser Glu Ser Ser Ser Thr Phe
                325


<210> SEQ ID NO 6
<211> LENGTH: 67
<212> TYPE: PRT
<213> ORGANISM: Artificial
<220> FEATURE:
<223> OTHER INFORMATION: This sequence was artificially derived and/or
      created by the inventors.

<400> SEQUENCE: 6

Met Gly His Arg Arg Ala His Ser Glu Ile Leu Ser Leu Pro Glu Asp
1               5                   10                  15

Leu Asp Leu Cys Ala Ala Gly Gly Gly Asp Gly Pro Ser Leu Ser Asp
            20                  25                  30

Glu Asn Asp Glu Glu Leu Phe Ser Met Phe Leu Asp Val Glu Lys Leu
        35                  40                  45

Asn Ser Thr Cys Gly Ala Ser Ser Glu Ala Glu Ala Glu Ser Ser Ser
    50                  55                  60

Ala Ala Ala
65


<210> SEQ ID NO 7
<211> LENGTH: 1107
<212> TYPE: DNA
<213> ORGANISM: Artificial
<220> FEATURE:
<223> OTHER INFORMATION: This sequence was artificially derived and/or
      created by the inventors.

<400> SEQUENCE: 7

atgaacaggg agaaatcccc gatcccggga gacggcggcg acgggttgcc gccgcaggcc      60

acccgccggg cgggccctcc ggcggcggcg gcggcggcgg agtacgacat cagccgcatg     120

ccggatttcc cgacgaggaa ccccggccac aggcgcgccc actccgagat cctgagcctc     180

cccgaggacc tcgacctgtg cgcggccggc ggcggcgacg ggccgtcgct gtcggacgag     240

aacgacgagg agctcttctc catgttcctc gacgtggaga agctgaacag cacgtgcggg     300

gcgtcgtcgg aggcggaggc ggagtcgtcg tccgccgccg cccatggagc gaggccgaag     360

caccagcaca gcctgtccat ggatgagtcg atgtcgatca aggctgagga gctcgtcggg     420

gcgtcgcccg ggacggaggg gatgtcgtcg gcggaggcca agaaggccgt gtccgcggtc     480
```

-continued

```
aagctcgccg agcttgctct cgtcgatccc aagagggcga aaaggatttg ggctaacaga    540

caatctgcgg caagatcaaa ggaaaggaaa atgcgatata ttgctgaact tgagcgcaag    600

gtgcaaaccc tgcaaacaga agcaacaaca ctgtcagccc agttggcact gctacagaga    660

gataccagtg ggctaactac tgagaatagt gaactgaagc tacgtctgca gaccatggag    720

cagcaagtcc acttgcaaga tgctttgaat gacaccctga agtctgaggt tcagcggctt    780

aaggttgcaa ccggtcaaat ggcgaatggt ggagggatga tgatgaactt cggtggcatg    840

ccacaccaat tcggaggcaa ccagcagatg ttccagaaca accaggccat gcaatctatg    900

ctggcagcac accagctgca acagctccag cttcatcctc aggctcagca gcagcaggtg    960

ctgcaccctc agcatcagca gcagcagcca ttgcaccctc tacaagcgca gcagctccag   1020

caggcggcac gagacctcaa gatgaaatcg ccgatgggcg gccagagcca gtggggagat   1080

ggcaagtcag gaagcagcgg caactga                                         1107
```

<210> SEQ ID NO 8
<211> LENGTH: 990
<212> TYPE: DNA
<213> ORGANISM: Artificial
<220> FEATURE:
<223> OTHER INFORMATION: This sequence was artificially derived and/or created by the inventors.

<400> SEQUENCE: 8

```
atgcaggagc caaagcacac cgatccggcg gccatgcgcg gggcgcacca ccgccgggcc     60

agatctgagg tcgccttccg cctgcccgac gacctcgacc tcggcggcgg cggcgcgggg    120

gcgttcgacg agatcggctc cgaggacgac ctcttctcca ccttcatgga catcgagaag    180

atctcctccg gccccgccgc cgcggggggc tccgaccggg accgcgccgc ggagacgtcc    240

tcgccgccgc gccccaagca ccgccacagc agctccgtcg acggctccgg gttcttcgcc    300

gccgcgcgga aggacgccgc cgcatcgctg gcggaggtca tggaggctaa gaaggccatg    360

acccccgagc agctctccga tctcgccgcc atcgacccca agcgcgccaa aagaattctg    420

gcgaacagac aatctgcagc tcggtcaaaa gagagaaaag ctcgttacat aacagaactt    480

gagcggaagg ttcaaactct tcagactgaa gccactactc tctcagcaca actcacacta    540

tttcagagag acacaactgg gctttctgca gaaaatgcag agctcaagat acggttgcag    600

gccatggaac aacaggctca actgcgagat gctctgaatg atgcactaaa gcaggaactg    660

gagaggctta agctcgctac tggtgagatg acaaattcca atgagacata tagcatggga    720

ctgcaacatg tcccatacaa cacccctttc ttccctctcg cccagcataa tgcagcccgc    780

cagaacggtg gaacccagtt gccaccacaa ttccaaccac cccgtcctaa tgtgcccaat    840

cacatgctat cccatccaaa cggtttgcaa gatatcatgc agcaagaccc tcttggccgg    900

cttcagggtt tggacatcag caaagggcct ctagttgtga aatcagagag cagctcgatc    960

tctgcaagtg aaagcagcag caccttctaa                                      990
```

<210> SEQ ID NO 9
<211> LENGTH: 201
<212> TYPE: DNA
<213> ORGANISM: Artificial
<220> FEATURE:
<223> OTHER INFORMATION: This sequence was artificially derived and/or created by the inventors.

<400> SEQUENCE: 9

-continued

```
atgggccaca ggcgcgccca ctccgagatc ctgagcctcc ccgaggacct cgacctgtgc     60

gcggccggcg gcggcgacgg gccgtcgctg tcggacgaga acgacgagga gctcttctcc    120

atgttcctcg acgtggagaa gctgaacagc acgtgcgggg cgtcgtcgga ggcggaggcg    180

gagtcgtcgt ccgccgccgc c                                              201


<210> SEQ ID NO 10
<211> LENGTH: 35
<212> TYPE: DNA
<213> ORGANISM: Artificial
<220> FEATURE:
<223> OTHER INFORMATION: This sequence was artificially derived and/or
      created by the inventors.

<400> SEQUENCE: 10

ctccttatat actggagttc attatacact cttac                                35


<210> SEQ ID NO 11
<211> LENGTH: 35
<212> TYPE: DNA
<213> ORGANISM: Artificial
<220> FEATURE:
<223> OTHER INFORMATION: This sequence was artificially derived and/or
      created by the inventors.

<400> SEQUENCE: 11

gtaagagtgt ataatgaact ccagtatata aggag                                35


<210> SEQ ID NO 12
<211> LENGTH: 209
<212> TYPE: DNA
<213> ORGANISM: Rice tungro bacilliform virus

<400> SEQUENCE: 12

acgaatcaat aaagaaggac cagaagatat aaagctggaa catcttcaca tgctaccaca     60

tggctagcat ctttacttta gcatctctat tattgtaaga gtgtataatg accagtgtgc    120

ccctggactc cagtatataa ggagcaccag agtagtgtaa tagatcatcg atcaagcaag    180

cgagagctca aacttctaag agagcaaga                                      209


<210> SEQ ID NO 13
<211> LENGTH: 23
<212> TYPE: DNA
<213> ORGANISM: Artificial
<220> FEATURE:
<223> OTHER INFORMATION: This sequence was artificially derived and/or
      created by the inventors.

<400> SEQUENCE: 13

gatttcacgg gttggggttt cta                                             23


<210> SEQ ID NO 14
<211> LENGTH: 37
<212> TYPE: DNA
<213> ORGANISM: Artificial
<220> FEATURE:
<223> OTHER INFORMATION: This sequence was artificially derived and/or
      created by the inventors.

<400> SEQUENCE: 14

tcattccagg ggcacactgg atacactctt acaataa                              37


<210> SEQ ID NO 15
<211> LENGTH: 37
```

-continued

<212> TYPE: DNA
<213> ORGANISM: Artificial
<220> FEATURE:
<223> OTHER INFORMATION: This sequence was artificially derived and/or
created by the inventors.

<400> SEQUENCE: 15
tgtatccagt gtgcccctgg aatgaactcc agtatat 37

<210> SEQ ID NO 16
<211> LENGTH: 37
<212> TYPE: DNA
<213> ORGANISM: Artificial
<220> FEATURE:
<223> OTHER INFORMATION: This sequence was artificially derived and/or
created by the inventors.

<400> SEQUENCE: 16
atacaccagg ggcacactgg ctcttacaat aatagag 37

<210> SEQ ID NO 17
<211> LENGTH: 37
<212> TYPE: DNA
<213> ORGANISM: Artificial
<220> FEATURE:
<223> OTHER INFORMATION: This sequence was artificially derived and/or
created by the inventors.

<400> SEQUENCE: 17
aagagccagt gtgcccctgg tgtataatga actccag 37

<210> SEQ ID NO 18
<211> LENGTH: 37
<212> TYPE: DNA
<213> ORGANISM: Artificial
<220> FEATURE:
<223> OTHER INFORMATION: This sequence was artificially derived and/or
created by the inventors.

<400> SEQUENCE: 18
caataccagg ggcacactgg atagagatgc taaagta 37

<210> SEQ ID NO 19
<211> LENGTH: 37
<212> TYPE: DNA
<213> ORGANISM: Artificial
<220> FEATURE:
<223> OTHER INFORMATION: This sequence was artificially derived and/or
created by the inventors.

<400> SEQUENCE: 19
tctatccagt gtgcccctgg tattgtaaga gtgtata 37

<210> SEQ ID NO 20
<211> LENGTH: 37
<212> TYPE: DNA
<213> ORGANISM: Artificial
<220> FEATURE:
<223> OTHER INFORMATION: This sequence was artificially derived and/or
created by the inventors.

<400> SEQUENCE: 20
atagaccagg ggcacactgg gatgctaaag taaagat 37

<210> SEQ ID NO 21
<211> LENGTH: 37
<212> TYPE: DNA

-continued

<213> ORGANISM: Artificial
<220> FEATURE:
<223> OTHER INFORMATION: This sequence was artificially derived and/or
created by the inventors.

<400> SEQUENCE: 21
gcatcccagt gtgcccctgg tctattattg taagagt 37

<210> SEQ ID NO 22
<211> LENGTH: 37
<212> TYPE: DNA
<213> ORGANISM: Artificial
<220> FEATURE:
<223> OTHER INFORMATION: This sequence was artificially derived and/or
created by the inventors.

<400> SEQUENCE: 22
tgctaccagg ggcacactgg gccatgtggt agcatgt 37

<210> SEQ ID NO 23
<211> LENGTH: 37
<212> TYPE: DNA
<213> ORGANISM: Artificial
<220> FEATURE:
<223> OTHER INFORMATION: This sequence was artificially derived and/or
created by the inventors.

<400> SEQUENCE: 23
atggcccagt gtgcccctgg tagcatcttt actttag 37

<210> SEQ ID NO 24
<211> LENGTH: 37
<212> TYPE: DNA
<213> ORGANISM: Artificial
<220> FEATURE:
<223> OTHER INFORMATION: This sequence was artificially derived and/or
created by the inventors.

<400> SEQUENCE: 24
gcatgccagg ggcacactgg tgaagatgtt ccagctt 37

<210> SEQ ID NO 25
<211> LENGTH: 37
<212> TYPE: DNA
<213> ORGANISM: Artificial
<220> FEATURE:
<223> OTHER INFORMATION: This sequence was artificially derived and/or
created by the inventors.

<400> SEQUENCE: 25
cttcaccagt gtgcccctgg catgctacca catggct 37

<210> SEQ ID NO 26
<211> LENGTH: 37
<212> TYPE: DNA
<213> ORGANISM: Artificial
<220> FEATURE:
<223> OTHER INFORMATION: This sequence was artificially derived and/or
created by the inventors.

<400> SEQUENCE: 26
tggtcccagg ggcacactgg cttctttatt gattcgt 37

<210> SEQ ID NO 27
<211> LENGTH: 37
<212> TYPE: DNA
<213> ORGANISM: Artificial

-continued

<220> FEATURE:
<223> OTHER INFORMATION: This sequence was artificially derived and/or
      created by the inventors.

<400> SEQUENCE: 27
agaagccagt gtgcccctgg gaccagaaga tataaag 37

<210> SEQ ID NO 28
<211> LENGTH: 44
<212> TYPE: DNA
<213> ORGANISM: Artificial
<220> FEATURE:
<223> OTHER INFORMATION: This sequence was artificially derived and/or
      created by the inventors.

<400> SEQUENCE: 28
tgatcaaagc ttccagtgtg cccctggacg aatcaataaa gaag 44

<210> SEQ ID NO 29
<211> LENGTH: 44
<212> TYPE: DNA
<213> ORGANISM: Artificial
<220> FEATURE:
<223> OTHER INFORMATION: This sequence was artificially derived and/or
      created by the inventors.

<400> SEQUENCE: 29
tgatcaaagc ttccagtgtg cccctggacg aatcaataaa gaag 44

<210> SEQ ID NO 30
<211> LENGTH: 37
<212> TYPE: DNA
<213> ORGANISM: Artificial
<220> FEATURE:
<223> OTHER INFORMATION: This sequence was artificially derived and/or
      created by the inventors.

<400> SEQUENCE: 30
ctctgccagg ggcacactgg gtgctcctta tatactg 37

<210> SEQ ID NO 31
<211> LENGTH: 37
<212> TYPE: DNA
<213> ORGANISM: Artificial
<220> FEATURE:
<223> OTHER INFORMATION: This sequence was artificially derived and/or
      created by the inventors.

<400> SEQUENCE: 31
agcacccagt gtgcccctgg cagagtagtg taataga 37

<210> SEQ ID NO 32
<211> LENGTH: 37
<212> TYPE: DNA
<213> ORGANISM: Artificial
<220> FEATURE:
<223> OTHER INFORMATION: This sequence was artificially derived and/or
      created by the inventors.

<400> SEQUENCE: 32
ttacaccagg ggcacactgg ctactctggt gctcctt 37

<210> SEQ ID NO 33
<211> LENGTH: 37
<212> TYPE: DNA
<213> ORGANISM: Artificial
<220> FEATURE:

-continued

<223> OTHER INFORMATION: This sequence was artificially derived and/or created by the inventors.

<400> SEQUENCE: 33
agtagccagt gtgcccctgg tgtaatagat catcgat 37

<210> SEQ ID NO 34
<211> LENGTH: 37
<212> TYPE: DNA
<213> ORGANISM: Artificial
<220> FEATURE:
<223> OTHER INFORMATION: This sequence was artificially derived and/or created by the inventors.

<400> SEQUENCE: 34
ttgctccagg ggcacactgg tgatcgatga tctatta 37

<210> SEQ ID NO 35
<211> LENGTH: 37
<212> TYPE: DNA
<213> ORGANISM: Artificial
<220> FEATURE:
<223> OTHER INFORMATION: This sequence was artificially derived and/or created by the inventors.

<400> SEQUENCE: 35
gatcaccagt gtgcccctgg agcaagcgag agctcaa 37

<210> SEQ ID NO 36
<211> LENGTH: 23
<212> TYPE: DNA
<213> ORGANISM: Artificial
<220> FEATURE:
<223> OTHER INFORMATION: This sequence was artificially derived and/or created by the inventors.

<400> SEQUENCE: 36
gatttcacgg gttggggttt cta 23

<210> SEQ ID NO 37
<211> LENGTH: 44
<212> TYPE: DNA
<213> ORGANISM: Artificial
<220> FEATURE:
<223> OTHER INFORMATION: This sequence was artificially derived and/or created by the inventors.

<400> SEQUENCE: 37
tgatcaaagc ttccagtgtg cccctggtcg caagaccctt cctc 44

<210> SEQ ID NO 38
<211> LENGTH: 44
<212> TYPE: DNA
<213> ORGANISM: Artificial
<220> FEATURE:
<223> OTHER INFORMATION: This sequence was artificially derived and/or created by the inventors.

<400> SEQUENCE: 38
tgatcaaagc ttccagtgtg cccctggatc cttcgcaaga ccct 44

<210> SEQ ID NO 39
<211> LENGTH: 44
<212> TYPE: DNA
<213> ORGANISM: Artificial
<220> FEATURE:
<223> OTHER INFORMATION: This sequence was artificially derived and/or created by the inventors.

<400> SEQUENCE: 39
tgatcaaagc ttccagtgtg cccctgggac gcacaatccc acta 44

<210> SEQ ID NO 40
<211> LENGTH: 44
<212> TYPE: DNA
<213> ORGANISM: Artificial
<220> FEATURE:
<223> OTHER INFORMATION: This sequence was artificially derived and/or created by the inventors.

<400> SEQUENCE: 40
tgatcaaagc ttccagtgtg cccctggggg atgacgcaca atcc 44

<210> SEQ ID NO 41
<211> LENGTH: 44
<212> TYPE: DNA
<213> ORGANISM: Artificial
<220> FEATURE:
<223> OTHER INFORMATION: This sequence was artificially derived and/or created by the inventors.

<400> SEQUENCE: 41
tgatcaaagc ttccagtgtg cccctggatc tccactgacg taag 44

<210> SEQ ID NO 42
<211> LENGTH: 44
<212> TYPE: DNA
<213> ORGANISM: Artificial
<220> FEATURE:
<223> OTHER INFORMATION: This sequence was artificially derived and/or created by the inventors.

<400> SEQUENCE: 42
tgatcaaagc ttccagtgtg cccctgggtg atatctccac tgac 44

<210> SEQ ID NO 43
<211> LENGTH: 29
<212> TYPE: DNA
<213> ORGANISM: Artificial
<220> FEATURE:
<223> OTHER INFORMATION: This sequence was artificially derived and/or created by the inventors.

<400> SEQUENCE: 43
tgatcaaagc ttatccttcg caagaccct 29

<210> SEQ ID NO 44
<211> LENGTH: 29
<212> TYPE: DNA
<213> ORGANISM: Artificial
<220> FEATURE:
<223> OTHER INFORMATION: This sequence was artificially derived and/or created by the inventors.

<400> SEQUENCE: 44
tgatcaaagc ttgggatgac gcacaatcc 29

<210> SEQ ID NO 45
<211> LENGTH: 29
<212> TYPE: DNA
<213> ORGANISM: Artificial
<220> FEATURE:
<223> OTHER INFORMATION: This sequence was artificially derived and/or created by the inventors.

-continued

<400> SEQUENCE: 45
tgatcaaagc ttgtgatatc tccactgac 29

<210> SEQ ID NO 46
<211> LENGTH: 36
<212> TYPE: DNA
<213> ORGANISM: Artificial
<220> FEATURE:
<223> OTHER INFORMATION: This sequence was artificially derived and/or created by the inventors.

<400> SEQUENCE: 46
gccgcccata tggagaagat gaacagggag aaatcc 36

<210> SEQ ID NO 47
<211> LENGTH: 33
<212> TYPE: DNA
<213> ORGANISM: Artificial
<220> FEATURE:
<223> OTHER INFORMATION: This sequence was artificially derived and/or created by the inventors.

<400> SEQUENCE: 47
gccgcccata tggagaagat gggccacagg cgc 33

<210> SEQ ID NO 48
<211> LENGTH: 33
<212> TYPE: DNA
<213> ORGANISM: Artificial
<220> FEATURE:
<223> OTHER INFORMATION: This sequence was artificially derived and/or created by the inventors.

<400> SEQUENCE: 48
gccgcccata tggagaagat gtccgccgcc gcc 33

<210> SEQ ID NO 49
<211> LENGTH: 30
<212> TYPE: DNA
<213> ORGANISM: Artificial
<220> FEATURE:
<223> OTHER INFORMATION: This sequence was artificially derived and/or created by the inventors.

<400> SEQUENCE: 49
cgcggatcct cagttgccgc tgcttcctga 30

<210> SEQ ID NO 50
<211> LENGTH: 30
<212> TYPE: DNA
<213> ORGANISM: Artificial
<220> FEATURE:
<223> OTHER INFORMATION: This sequence was artificially derived and/or created by the inventors.

<400> SEQUENCE: 50
cgcggatcct cagtgtggca tgccaccgaa 30

<210> SEQ ID NO 51
<211> LENGTH: 44
<212> TYPE: DNA
<213> ORGANISM: Artificial
<220> FEATURE:
<223> OTHER INFORMATION: This sequence was artificially derived and/or created by the inventors.

-continued

<400> SEQUENCE: 51
tgatcaaagc ttccagtgtg cccctggtcg caagaccctt cctc 44

<210> SEQ ID NO 52
<211> LENGTH: 23
<212> TYPE: DNA
<213> ORGANISM: Artificial
<220> FEATURE:
<223> OTHER INFORMATION: This sequence was artificially derived and/or created by the inventors.

<400> SEQUENCE: 52
gatttcacgg gttggggttt cta 23

<210> SEQ ID NO 53
<211> LENGTH: 44
<212> TYPE: DNA
<213> ORGANISM: Artificial
<220> FEATURE:
<223> OTHER INFORMATION: This sequence was artificially derived and/or created by the inventors.

<400> SEQUENCE: 53
tgatcaaagc ttccagtgtg cccctggtcg caagaccctt cctc 44

<210> SEQ ID NO 54
<211> LENGTH: 48
<212> TYPE: PRT
<213> ORGANISM: Artificial
<220> FEATURE:
<223> OTHER INFORMATION: This sequence was artificially derived and/or created by the inventors.

<400> SEQUENCE: 54

```
Met Asn Arg Glu Lys Ser Pro Ile Pro Gly Asp Gly Gly Asp Gly Leu
1               5                   10                  15

Pro Pro Gln Ala Thr Arg Arg Ala Gly Pro Pro Ala Ala Ala Ala Ala
            20                  25                  30

Ala Glu Tyr Asp Ile Ser Arg Met Pro Asp Phe Pro Thr Arg Asn Pro
        35                  40                  45
```

<210> SEQ ID NO 55
<211> LENGTH: 87
<212> TYPE: PRT
<213> ORGANISM: Artificial
<220> FEATURE:
<223> OTHER INFORMATION: This sequence was artificially derived and/or created by the inventors.

<400> SEQUENCE: 55

```
Met Gln Phe Gly Gly Asn Gln Gln Met Phe Gln Asn Asn Gln Ala Met
1               5                   10                  15

Gln Ser Met Leu Ala Ala His Gln Leu Gln Gln Leu Gln Leu His Pro
            20                  25                  30

Gln Ala Gln Gln Gln Gln Val Leu His Pro Gln His Gln Gln Gln Gln
        35                  40                  45

Pro Leu His Pro Leu Gln Ala Gln Gln Leu Gln Gln Ala Ala Arg Asp
    50                  55                  60

Leu Lys Met Lys Ser Pro Met Gly Gly Gln Ser Gln Trp Gly Asp Gly
65                  70                  75                  80

Lys Ser Gly Ser Ser Gly Asn
                85
```

-continued

```
<210> SEQ ID NO 56
<211> LENGTH: 28
<212> TYPE: DNA
<213> ORGANISM: Artificial
<220> FEATURE:
<223> OTHER INFORMATION: This sequence was artificially derived and/or
      created by the inventors.

<400> SEQUENCE: 56

gccagatcta tgggccacag gcgcgccc                                        28


<210> SEQ ID NO 57
<211> LENGTH: 25
<212> TYPE: DNA
<213> ORGANISM: Artificial
<220> FEATURE:
<223> OTHER INFORMATION: This sequence was artificially derived and/or
      created by the inventors.

<400> SEQUENCE: 57

cgcggatcct ccatgggcgg cggcg                                           25


<210> SEQ ID NO 58
<211> LENGTH: 29
<212> TYPE: DNA
<213> ORGANISM: Artificial
<220> FEATURE:
<223> OTHER INFORMATION: This sequence was artificially derived and/or
      created by the inventors.

<400> SEQUENCE: 58

gccagatcta tgaacaggga gaaatcccc                                       29


<210> SEQ ID NO 59
<211> LENGTH: 27
<212> TYPE: DNA
<213> ORGANISM: Artificial
<220> FEATURE:
<223> OTHER INFORMATION: This sequence was artificially derived and/or
      created by the inventors.

<400> SEQUENCE: 59

cgcggatccg gggttcctcg tcgggaa                                         27


<210> SEQ ID NO 60
<211> LENGTH: 31
<212> TYPE: DNA
<213> ORGANISM: Artificial
<220> FEATURE:
<223> OTHER INFORMATION: This sequence was artificially derived and/or
      created by the inventors.

<400> SEQUENCE: 60

gccagatcta tgcaattcgg aggcaaccag c                                    31


<210> SEQ ID NO 61
<211> LENGTH: 27
<212> TYPE: DNA
<213> ORGANISM: Artificial
<220> FEATURE:
<223> OTHER INFORMATION: This sequence was artificially derived and/or
      created by the inventors.

<400> SEQUENCE: 61

cgcggatccg ttgccgctgc ttcctga                                         27
```

-continued

<210> SEQ ID NO 62
<211> LENGTH: 775
<212> TYPE: DNA
<213> ORGANISM: Rice tungro bacilliform virus

<400> SEQUENCE: 62
agatcttcta caaaagggag tagtaatatt taatgagctt gaaggaggat atcaactctc 60
tccaaggttt attggagacc tttatgctca tggttttatt aaacaaataa acttcacaac 120
caaggttcct gaagggctac cgccaatcat tgcggaaaaa cttcaagact ataagttccc 180
tggatcaaat accgtcttaa tagaacgaga gattcctcgc tggaacttca atgaaatgaa 240
aagagaaaca cagatgagga ccaacttata tatcttcaag aattatcgct gtttctatgg 300
ctattcacca ttaaggccat acgaacctat aactcctgaa gaatttgggt ttgattacta 360
cagttgggaa aatatggttg atgaagacga aggagaagtt gtatacatct ccaagtatac 420
taagattatc aaagtcacta aagagcatgc atgggcttgg ccagaacatg atggagacac 480
aatgtcctgc accacatcaa tagaagatga atggatccat cgtatggaca atgcttaaag 540
aagctttatc aaaagcaact ttaagtacga atcaataaag aaggaccaga agatataaag 600
ctggaacatc ttcacatgct accacatggc tagcatcttt actttagcat ctctattatt 660
gtaagagtgt ataatgacca gtgtgcccct ggactccagt atataaggag caccagagta 720
gtgtaataga tcatcgatca agcaagcgag agctcaaact tctaagagag caaga 775

<210> SEQ ID NO 63
<211> LENGTH: 209
<212> TYPE: DNA
<213> ORGANISM: Rice tungro bacilliform virus

<400> SEQUENCE: 63
acgaatcaat aaagaaggac cagaagatat aaagctggaa catcttcaca tgctaccaca 60
tggctagcat ctttacttta gcatctctat tattgtaaga gtgtataatg accagtgtgg 120
cgctggactc cagtatataa ggagcaccag agtagtgtaa tagatcatcg atcaagcaag 180
cgagagctca aacttctaag agagcaaga 209

<210> SEQ ID NO 64
<211> LENGTH: 209
<212> TYPE: DNA
<213> ORGANISM: Rice tungro bacilliform virus

<400> SEQUENCE: 64
acgaatcaat aaagaaggac cagaagatat aaagctggaa catcttcaca tgctaccaca 60
tggctagcat ctttacttta gcatctctat tattgtaaga gtgtataatg aggagtgtgc 120
cccttcactc cagtatataa ggagcaccag agtagtgtaa tagatcatcg atcaagcaag 180
cgagagctca aacttctaag agagcaaga 209

<210> SEQ ID NO 65
<211> LENGTH: 194
<212> TYPE: DNA
<213> ORGANISM: Artificial
<220> FEATURE:
<223> OTHER INFORMATION: This sequence was artificially derived and/or
created by the inventors.

<400> SEQUENCE: 65
acgaatcaat aaagaaggac cagaagatat aaagctggaa catcttcaca tgctaccaca 60
tggctagcat ctttacttta gcatctctat tattgtaaga gtgtataatg aactccagta 120

-continued

```
tataaggagc accagagtag tgtaatagat catcgatcaa gcaagcgaga gctcaaactt    180

ctaagagagc aaga                                                      194


<210> SEQ ID NO 66
<211> LENGTH: 108
<212> TYPE: DNA
<213> ORGANISM: Cauliflower mosaic virus

<400> SEQUENCE: 66

ttgatgtgat atctccactg acgtaaggga tgacgcacaa tcccactatc cttcgcaaga     60

cccttcctct atataaggaa gttcatttca tttggagagg acacgctg                 108


<210> SEQ ID NO 67
<211> LENGTH: 552
<212> TYPE: DNA
<213> ORGANISM: Cassava vein mosaic virus

<400> SEQUENCE: 67

ccaagatgta gcatcaagaa tccaatgttt acgggaaaaa ctatggaagt attatgtgag     60

ctcagcaaga agcagatcaa tatgcggcac atatgcaacc tatgttcaaa aatgaagaat    120

gtacagatac aagatcctat actgccagaa tacgaagaag aatacgtaga aattgaaaaa    180

gaagaaccag gcgaagaaaa gaatcttgaa gacgtaagca ctgacgacaa caatgaaaag    240

aagaagataa ggtcggtgat tgtgaaagag acatagagga cacatgtaag gtggaaaatg    300

taagggcgga aagtaacctt atcacaaagg aatcttatcc cccactactt atccttttat    360

atttttccgt gtcatttttg cccttgagtt ttcctatata aggaaccaag ttcggcattt    420

gtgaaaacaa gaaaaaattt ggtgtaagct attttctttg aagtactgag gatacaactt    480

cagagaaatt tgtaagtttg taatgttttt agtttttata ataatatgtt tatgtttgtt    540

ttaataatga gt                                                        552


<210> SEQ ID NO 68
<211> LENGTH: 320
<212> TYPE: PRT
<213> ORGANISM: Artificial
<220> FEATURE:
<223> OTHER INFORMATION: This sequence was artificially derived and/or
      created by the inventors.

<400> SEQUENCE: 68

Met Gly His Arg Arg Ala His Ser Glu Ile Leu Ser Leu Pro Glu Asp
1               5                   10                  15

Leu Asp Leu Cys Ala Ala Gly Gly Gly Asp Gly Pro Ser Leu Ser Asp
            20                  25                  30

Glu Asn Asp Glu Glu Leu Phe Ser Met Phe Leu Asp Val Glu Lys Leu
        35                  40                  45

Asn Ser Thr Cys Gly Ala Ser Ser Glu Ala Glu Ala Glu Ser Ser Ser
    50                  55                  60

Ala Ala Ala His Gly Ala Arg Pro Lys His Gln His Ser Leu Ser Met
65                  70                  75                  80

Asp Glu Ser Met Ser Ile Ala Glu Glu Leu Val Gly Ala Ser Pro Gly
                85                  90                  95

Thr Glu Gly Met Ser Ser Ala Glu Ala Lys Lys Ala Val Ser Ala Val
            100                 105                 110

Lys Leu Ala Glu Leu Ala Leu Val Asp Pro Lys Arg Ala Lys Arg Ile
        115                 120                 125
```

-continued

```
Trp Ala Asn Arg Gln Ser Ala Ala Arg Ser Lys Glu Arg Lys Met Arg
    130                 135                 140

Tyr Ile Ala Glu Leu Glu Arg Lys Val Gln Thr Leu Gln Thr Glu Ala
145                 150                 155                 160

Thr Thr Leu Ser Ala Gln Leu Ala Leu Leu Gln Arg Asp Thr Ser Gly
                165                 170                 175

Leu Thr Thr Glu Asn Ser Glu Leu Lys Leu Arg Leu Gln Thr Met Glu
            180                 185                 190

Gln Gln Val His Leu Gln Asp Ala Leu Asn Asp Thr Leu Lys Ser Glu
        195                 200                 205

Val Gln Arg Leu Lys Val Ala Thr Gly Gln Met Ala Asn Gly Gly Gly
    210                 215                 220

Met Met Met Asn Phe Gly Gly Met Pro His Gln Phe Gly Gly Asn Gln
225                 230                 235                 240

Gln Met Phe Gln Asn Asn Gln Ala Met Gln Ser Met Leu Ala Ala His
                245                 250                 255

Gln Leu Gln Gln Leu Gln Leu His Pro Gln Ala Gln Gln Gln Gln Val
            260                 265                 270

Leu His Pro Gln His Gln Gln Gln Gln Pro Leu His Pro Leu Gln Ala
        275                 280                 285

Gln Gln Leu Gln Gln Ala Ala Arg Asp Leu Lys Met Lys Ser Pro Met
    290                 295                 300

Gly Gly Gln Ser Gln Trp Gly Asp Gly Lys Ser Gly Ser Ser Gly Asn
305                 310                 315                 320


<210> SEQ ID NO 69
<211> LENGTH: 283
<212> TYPE: PRT
<213> ORGANISM: Artificial
<220> FEATURE:
<223> OTHER INFORMATION: This sequence was artificially derived and/or
      created by the inventors.

<400> SEQUENCE: 69

Met Asn Arg Glu Lys Ser Pro Ile Pro Gly Asp Gly Gly Asp Gly Leu
1               5                   10                  15

Pro Pro Gln Ala Thr Arg Arg Ala Gly Pro Pro Ala Ala Ala Ala Ala
            20                  25                  30

Ala Glu Tyr Asp Ile Ser Arg Met Pro Asp Phe Pro Thr Arg Asn Pro
        35                  40                  45

Gly His Arg Arg Ala His Ser Glu Ile Leu Ser Leu Pro Glu Asp Leu
    50                  55                  60

Asp Leu Cys Ala Ala Gly Gly Gly Asp Gly Pro Ser Leu Ser Asp Glu
65                  70                  75                  80

Asn Asp Glu Glu Leu Phe Ser Met Phe Leu Asp Val Glu Lys Leu Asn
                85                  90                  95

Ser Thr Cys Gly Ala Ser Ser Glu Ala Glu Ala Glu Ser Ser Ser Ala
            100                 105                 110

Ala Ala His Gly Ala Arg Pro Lys His Gln His Ser Leu Ser Met Asp
        115                 120                 125

Glu Ser Met Ser Ile Lys Ala Glu Glu Leu Val Gly Ala Ser Pro Gly
    130                 135                 140

Thr Glu Gly Met Ser Ser Ala Glu Ala Lys Lys Ala Val Ser Ala Val
145                 150                 155                 160

Lys Leu Ala Glu Leu Ala Leu Val Asp Pro Lys Arg Ala Lys Arg Ile
```

-continued

```
                165                 170                 175

Trp Ala Asn Arg Gln Ser Ala Ala Arg Ser Lys Glu Arg Lys Met Arg
            180                 185                 190

Tyr Ile Ala Glu Leu Glu Arg Lys Val Gln Thr Leu Gln Thr Glu Ala
        195                 200                 205

Thr Thr Leu Ser Ala Gln Leu Ala Leu Leu Gln Arg Asp Thr Ser Gly
    210                 215                 220

Leu Thr Thr Glu Asn Ser Glu Leu Lys Leu Arg Leu Gln Thr Met Glu
225                 230                 235                 240

Gln Gln Val His Leu Gln Asp Ala Leu Asn Asp Thr Leu Lys Ser Glu
                245                 250                 255

Val Gln Arg Leu Lys Val Ala Thr Gly Gln Met Ala Asn Gly Gly Gly
            260                 265                 270

Met Met Met Asn Phe Gly Gly Met Pro His Gln
        275                 280


<210> SEQ ID NO 70
<211> LENGTH: 261
<212> TYPE: PRT
<213> ORGANISM: Artificial
<220> FEATURE:
<223> OTHER INFORMATION: This sequence was artificially derived and/or
      created by the inventors.

<400> SEQUENCE: 70

Met Ser Ser Ser Ala Ala Ala His Gly Ala Arg Pro Lys His Gln His
1               5                   10                  15

Ser Leu Ser Met Asp Glu Ser Met Ser Ile Lys Ala Glu Glu Leu Val
            20                  25                  30

Gly Ala Ser Pro Gly Thr Glu Gly Met Ser Ser Ala Glu Ala Lys Lys
        35                  40                  45

Ala Val Ser Ala Val Lys Leu Ala Glu Leu Ala Leu Val Asp Pro Lys
    50                  55                  60

Arg Ala Lys Arg Ile Trp Ala Asn Arg Gln Ser Ala Ala Arg Ser Lys
65                  70                  75                  80

Glu Arg Lys Met Arg Tyr Ile Ala Glu Leu Glu Arg Lys Val Gln Thr
                85                  90                  95

Leu Gln Thr Glu Ala Thr Thr Leu Ser Ala Gln Leu Ala Leu Leu Gln
            100                 105                 110

Arg Asp Thr Ser Gly Leu Thr Thr Glu Asn Ser Glu Leu Lys Leu Arg
        115                 120                 125

Leu Gln Thr Met Glu Gln Gln Val His Leu Gln Asp Ala Leu Asn Asp
    130                 135                 140

Thr Leu Lys Ser Glu Val Gln Arg Leu Lys Val Ala Thr Gly Gln Met
145                 150                 155                 160

Ala Asn Gly Gly Gly Met Met Met Asn Phe Gly Gly Met Pro His Gln
                165                 170                 175

Phe Gly Gly Asn Gln Gln Met Phe Gln Asn Asn Gln Ala Met Gln Ser
            180                 185                 190

Met Leu Ala Ala His Gln Leu Gln Gln Leu Gln Leu His Pro Gln Ala
        195                 200                 205

Gln Gln Gln Gln Val Leu His Pro Gln His Gln Gln Gln Gln Pro Leu
    210                 215                 220

His Pro Leu Gln Ala Gln Gln Leu Gln Gln Ala Ala Arg Asp Leu Lys
225                 230                 235                 240
```

-continued

```
Met Lys Ser Pro Met Gly Gly Gln Ser Gln Trp Gly Asp Gly Lys Ser
                245                 250                 255

Gly Ser Ser Gly Asn
            260


<210> SEQ ID NO 71
<211> LENGTH: 236
<212> TYPE: PRT
<213> ORGANISM: Artificial
<220> FEATURE:
<223> OTHER INFORMATION: This sequence was artificially derived and/or
      created by the inventors.

<400> SEQUENCE: 71

Met Gly His Arg Arg Ala His Ser Glu Ile Leu Ser Leu Pro Glu Asp
1               5                   10                  15

Leu Asp Leu Cys Ala Ala Gly Gly Gly Asp Gly Pro Ser Leu Ser Asp
            20                  25                  30

Glu Asn Asp Glu Glu Leu Phe Ser Met Phe Leu Asp Val Glu Lys Leu
        35                  40                  45

Asn Ser Thr Cys Gly Ala Ser Ser Glu Ala Glu Ala Glu Ser Ser Ser
    50                  55                  60

Ala Ala Ala His Gly Ala Arg Pro Lys His Gln His Ser Leu Ser Met
65                  70                  75                  80

Asp Glu Ser Met Ser Ile Lys Ala Glu Glu Leu Val Gly Ala Ser Pro
                85                  90                  95

Gly Thr Glu Gly Met Ser Ser Ala Glu Ala Lys Lys Ala Val Ser Ala
            100                 105                 110

Val Lys Leu Ala Glu Leu Ala Leu Val Asp Pro Lys Arg Ala Lys Arg
        115                 120                 125

Ile Trp Ala Asn Arg Gln Ser Ala Ala Arg Ser Lys Glu Arg Lys Met
    130                 135                 140

Arg Tyr Ile Ala Glu Leu Glu Arg Lys Val Gln Thr Leu Gln Thr Glu
145                 150                 155                 160

Ala Thr Thr Leu Ser Ala Gln Leu Ala Leu Leu Gln Arg Asp Thr Ser
                165                 170                 175

Gly Leu Thr Thr Glu Asn Ser Glu Leu Lys Leu Arg Leu Gln Thr Met
            180                 185                 190

Glu Gln Gln Val His Leu Gln Asp Ala Leu Asn Asp Thr Leu Lys Ser
        195                 200                 205

Glu Val Gln Arg Leu Lys Val Ala Thr Gly Gln Met Ala Asn Gly Gly
    210                 215                 220

Gly Met Met Met Asn Phe Gly Gly Met Pro His Gln
225                 230                 235


<210> SEQ ID NO 72
<211> LENGTH: 176
<212> TYPE: PRT
<213> ORGANISM: Artificial
<220> FEATURE:
<223> OTHER INFORMATION: This sequence was artificially derived and/or
      created by the inventors.

<400> SEQUENCE: 72

Met Ser Ser Ser Ala Ala Ala His Gly Ala Arg Pro Lys His Gln His
1               5                   10                  15

Ser Leu Ser Met Asp Glu Ser Met Ser Ile Lys Ala Glu Glu Leu Val
            20                  25                  30
```

-continued

```
Gly Ala Ser Pro Gly Thr Glu Gly Met Ser Ser Ala Glu Ala Lys Lys
        35                  40                  45

Ala Val Ser Ala Val Lys Leu Ala Glu Leu Ala Leu Val Asp Pro Lys
    50                  55                  60

Arg Ala Lys Arg Ile Trp Ala Asn Arg Gln Ser Ala Ala Arg Ser Lys
65                  70                  75                  80

Glu Arg Lys Met Arg Tyr Ile Ala Glu Leu Glu Arg Lys Val Gln Thr
                85                  90                  95

Leu Gln Thr Glu Ala Thr Thr Leu Ser Ala Gln Leu Ala Leu Leu Gln
            100                 105                 110

Arg Asp Thr Ser Gly Leu Thr Thr Glu Asn Ser Glu Leu Lys Leu Arg
        115                 120                 125

Leu Gln Thr Met Glu Gln Gln Val His Leu Gln Asp Ala Leu Asn Asp
    130                 135                 140

Thr Leu Lys Ser Glu Val Gln Arg Leu Lys Val Ala Thr Gly Gln Met
145                 150                 155                 160

Ala Asn Gly Gly Gly Met Met Met Asn Phe Gly Gly Met Pro His Gln
                165                 170                 175


<210> SEQ ID NO 73
<211> LENGTH: 23
<212> TYPE: DNA
<213> ORGANISM: Artificial
<220> FEATURE:
<223> OTHER INFORMATION: This sequence was artificially derived and/or
      created by the inventors.

<400> SEQUENCE: 73

ttcacacagg aaacagctat gac                                              23


<210> SEQ ID NO 74
<211> LENGTH: 18
<212> TYPE: DNA
<213> ORGANISM: Artificial
<220> FEATURE:
<223> OTHER INFORMATION: This sequence was artificially derived and/or
      created by the inventors.

<400> SEQUENCE: 74

gcgtgggcgg cgtgggcg                                                    18


<210> SEQ ID NO 75
<211> LENGTH: 172
<212> TYPE: PRT
<213> ORGANISM: Artificial
<220> FEATURE:
<223> OTHER INFORMATION: This sequence was artificially derived and/or
      created by the inventors.

<400> SEQUENCE: 75

Met Leu Glu Leu Pro Tyr Ala Cys Pro Val Glu Ser Cys Asp Arg Arg
1               5                   10                  15

Phe Ser Lys Ser Ala Asp Leu Lys Arg His Ile Arg Ile His Thr Gly
            20                  25                  30

Gln Lys Pro Phe Gln Cys Arg Ile Cys Met Arg Asn Phe Ser Arg Ser
        35                  40                  45

Asp His Leu Thr Thr His Ile Arg Thr His Thr Gly Glu Lys Pro Phe
    50                  55                  60

Ala Cys Asp Ile Cys Gly Arg Lys Phe Ala Arg Ser Asp Glu Arg Lys
65                  70                  75                  80
```

-continued

```
Arg His Thr Lys Ile His Thr Gly Glu Lys Pro Tyr Ala Cys Pro Val
                85                  90                  95

Glu Ser Cys Asp Arg Arg Phe Ser Lys Ser Ala Asp Leu Lys Arg His
            100                 105                 110

Ile Arg Ile His Thr Gly Gln Lys Pro Phe Gln Cys Arg Ile Cys Met
        115                 120                 125

Arg Asn Phe Ser Arg Ser Asp His Leu Thr Thr His Ile Arg Thr His
    130                 135                 140

Thr Gly Glu Lys Pro Phe Ala Cys Asp Ile Cys Gly Arg Lys Phe Ala
145                 150                 155                 160

Arg Ser Asp Glu Arg Lys Arg His Thr Lys Ile His
                165                 170
```

<210> SEQ ID NO 76
<211> LENGTH: 516
<212> TYPE: DNA
<213> ORGANISM: Artificial
<220> FEATURE:
<223> OTHER INFORMATION: This sequence was artificially derived and/or created by the inventors.

<400> SEQUENCE: 76

```
atgctcgagc tcccctatgc ttgccctgtc gagtcctgcg atcgccgctt ttctaagtcg     60

gctgatctga agcgccatat ccgcatccac acaggccaga agcctttcca gtgtcgaata    120

tgcatgcgta acttcagtcg tagtgaccac cttaccaccc acatccgcac ccacacaggc    180

gagaagcctt ttgcctgtga catttgtggg aggaagtttg ccaggagtga tgaacgcaag    240

aggcatacca aaatccatac cggtgagaag ccctatgctt gccctgtcga gtcctgcgat    300

cgccgctttt ctaagtcggc tgatctgaag cgccatatcc gcatccacac aggccagaag    360

cccttccagt gtcgaatatg catgcgtaac ttcagtcgta gtgaccacct taccacccac    420

atccgcaccc acacaggcga gaagcctttt gcctgtgaca tttgtgggag gaagtttgcc    480

aggagtgatg aacgcaagag gcataccaaa atccat                              516
```

<210> SEQ ID NO 77
<211> LENGTH: 21
<212> TYPE: DNA
<213> ORGANISM: Artificial
<220> FEATURE:
<223> OTHER INFORMATION: This sequence was artificially derived and/or created by the inventors.

<400> SEQUENCE: 77

```
ccccaaagtc cagcttgaaa t                                               21
```

<210> SEQ ID NO 78
<211> LENGTH: 20
<212> TYPE: DNA
<213> ORGANISM: Artificial
<220> FEATURE:
<223> OTHER INFORMATION: This sequence was artificially derived and/or created by the inventors.

<400> SEQUENCE: 78

```
ttaatccaac ttggaaaatg                                                 20
```

<210> SEQ ID NO 79
<211> LENGTH: 11
<212> TYPE: DNA
<213> ORGANISM: Artificial
<220> FEATURE:

-continued

<223> OTHER INFORMATION: This sequence was artificially derived and/or
      created by the inventors.

<400> SEQUENCE: 79
ccaccacccc c 11

<210> SEQ ID NO 80
<211> LENGTH: 15
<212> TYPE: DNA
<213> ORGANISM: Artificial
<220> FEATURE:
<223> OTHER INFORMATION: This sequence was artificially derived and/or
      created by the inventors.

<400> SEQUENCE: 80
cttcaccacc ccact 15

<210> SEQ ID NO 81
<211> LENGTH: 12
<212> TYPE: DNA
<213> ORGANISM: Artificial
<220> FEATURE:
<223> OTHER INFORMATION: This sequence was artificially derived and/or
      created by the inventors.

<400> SEQUENCE: 81
tggaccctac ca 12

<210> SEQ ID NO 82
<211> LENGTH: 13
<212> TYPE: DNA
<213> ORGANISM: Artificial
<220> FEATURE:
<223> OTHER INFORMATION: This sequence was artificially derived and/or
      created by the inventors.

<400> SEQUENCE: 82
aggtcacccc att 13

<210> SEQ ID NO 83
<211> LENGTH: 18
<212> TYPE: DNA
<213> ORGANISM: Artificial
<220> FEATURE:
<223> OTHER INFORMATION: This sequence was artificially derived and/or
      created by the inventors.

<400> SEQUENCE: 83
tggatgtgga agacagca 18

<210> SEQ ID NO 84
<211> LENGTH: 65
<212> TYPE: PRT
<213> ORGANISM: Artificial
<220> FEATURE:
<223> OTHER INFORMATION: This sequence was artificially derived and/or
      created by the inventors.

<400> SEQUENCE: 84

```
Met Asp Glu Lys Arg Arg Ala Gln His Asn Glu Val Glu Arg Arg Arg
1               5                   10                  15

Arg Asp Lys Ile Asn Asn Trp Ile Val Gln Leu Ser Lys Ile Ile Pro
            20                  25                  30

Asp Ser Ser Met Glu Ser Thr Lys Ser Gly Gln Ser Lys Gly Gly Ile
        35                  40                  45
```

-continued

```
Leu Ser Lys Ala Ser Asp Tyr Ile Gln Glu Leu Arg Gln Ser Asn His
    50                  55                  60

Arg
65


<210> SEQ ID NO 85
<211> LENGTH: 21
<212> TYPE: DNA
<213> ORGANISM: Artificial
<220> FEATURE:
<223> OTHER INFORMATION: This sequence was artificially derived and/or
      created by the inventors.

<400> SEQUENCE: 85

cacccggtca cgtggcctac a                                                21


<210> SEQ ID NO 86
<211> LENGTH: 62
<212> TYPE: PRT
<213> ORGANISM: Artificial
<220> FEATURE:
<223> OTHER INFORMATION: This sequence was artificially derived and/or
      created by the inventors.

<400> SEQUENCE: 86

Lys Ala Glu Arg Lys Arg Met Arg Asn Arg Ile Ala Ala Ser Lys Ser
1               5                   10                  15

Arg Lys Arg Lys Leu Glu Arg Ile Ala Arg Leu Glu Glu Lys Val Lys
            20                  25                  30

Thr Leu Lys Ala Gln Asn Ser Glu Leu Ala Ser Thr Ala Asn Met Leu
        35                  40                  45

Arg Glu Gln Val Ala Gln Leu Lys Gln Lys Val Met Asn His
    50                  55                  60


<210> SEQ ID NO 87
<211> LENGTH: 20
<212> TYPE: DNA
<213> ORGANISM: Artificial
<220> FEATURE:
<223> OTHER INFORMATION: This sequence was artificially derived and/or
      created by the inventors.

<400> SEQUENCE: 87

cgtcgatgac gtcatcgacg                                                  20


<210> SEQ ID NO 88
<211> LENGTH: 90
<212> TYPE: PRT
<213> ORGANISM: Artificial
<220> FEATURE:
<223> OTHER INFORMATION: This sequence was artificially derived and/or
      created by the inventors.

<400> SEQUENCE: 88

Met Glu Arg Pro Tyr Ala Cys Pro Val Glu Ser Cys Asp Arg Arg Phe
1               5                   10                  15

Ser Gln Lys Thr Asn Leu Asp Thr His Ile Arg Ile His Thr Gly Gln
            20                  25                  30

Lys Pro Phe Gln Cys Arg Ile Cys Met Arg Asn Phe Ser Gln His Thr
        35                  40                  45

Gly Leu Asn Gln His Ile Arg Thr His Thr Gly Glu Lys Pro Phe Ala
    50                  55                  60

Cys Asp Ile Cys Gly Arg Lys Phe Ala Thr Leu His Thr Arg Asp Arg
```

-continued

```
65                  70                  75                  80

His Thr Lys Ile His Leu Arg Gln Lys Asp
                85                  90


<210> SEQ ID NO 89
<211> LENGTH: 16
<212> TYPE: DNA
<213> ORGANISM: Artificial
<220> FEATURE:
<223> OTHER INFORMATION: This sequence was artificially derived and/or
      created by the inventors.

<400> SEQUENCE: 89

gacgctataa aaggag                                                    16


<210> SEQ ID NO 90
<211> LENGTH: 76
<212> TYPE: PRT
<213> ORGANISM: Artificial
<220> FEATURE:
<223> OTHER INFORMATION: This sequence was artificially derived and/or
      created by the inventors.

<400> SEQUENCE: 90

Pro Pro Gly Thr Pro Ser Arg His Glu Lys Ser Leu Gly Leu Leu Thr
1               5                   10                  15

Thr Lys Phe Val Ser Leu Leu Gln Glu Ala Lys Asp Gly Val Leu Asp
            20                  25                  30

Leu Lys Leu Ala Ala Asp Thr Leu Ala Val Arg Gln Lys Arg Arg Ile
        35                  40                  45

Tyr Asp Ile Thr Asn Val Leu Glu Gly Ile Gly Leu Ile Glu Lys Lys
    50                  55                  60

Ser Lys Asn Ser Ile Gln Trp Lys Gly Val Gly Pro
65                  70                  75


<210> SEQ ID NO 91
<211> LENGTH: 16
<212> TYPE: DNA
<213> ORGANISM: Artificial
<220> FEATURE:
<223> OTHER INFORMATION: This sequence was artificially derived and/or
      created by the inventors.

<400> SEQUENCE: 91

attttcgcgc ggtttt                                                    16


<210> SEQ ID NO 92
<211> LENGTH: 163
<212> TYPE: DNA
<213> ORGANISM: Artificial
<220> FEATURE:
<223> OTHER INFORMATION: This sequence was artificially derived and/or
      created by the inventors.

<400> SEQUENCE: 92

gctcggagga cagtactccg ctcggaggac agtactccgc tcggaggaca gtactccgct     60

cgaggacagt actccgctcg gaggacagta ctccgatccg tagatctgca agacccttcc    120

tctatataag gaagttcatt tcatttggag aggacacgct gaa                      163


<210> SEQ ID NO 93
<211> LENGTH: 2595
<212> TYPE: DNA
<213> ORGANISM: Artificial
```

-continued

<220> FEATURE:
<223> OTHER INFORMATION: This sequence was artificially derived and/or
created by the inventors.

<400> SEQUENCE: 93

```
atggcccccc cgaccgatgt cagcctgggg gacgaactcc acttagacgg cgaggacgtg     60
gcgatggcgc atgccgacgc gctagacgat ttcgatctgg acatgttggg ggacggggat    120
tccccaggtc cgggatttac cccccacgac tccgcccccct acggcgctct ggatatggcc   180
gacttcgagt ttgagcagat gtttaccgat gcccttggaa ttgacgagta cggtgggaag    240
cttctaggta cctccagaag aatatcaggc ggggaattcg gcgggatgaa gctactgtct    300
tctatcgaac aagcatgcga tatttgccga cttaaaaagc tcaagtgctc caaagaaaaa    360
ccgaagtgcg ccaagtgtct gaagaacaac tgggagtgtc gctactctcc caaaaccaaa    420
aggtctccgc tgactagggc acatctgaca gaagtggaat caaggctaga aagactggaa    480
cagctatttc tactgatttt tcctcgagaa gaccttgaca tgattttgaa aatggattct    540
ttacaggata taaaagcatt gttaacagga ttatttgtac aagataatgt gaataaagat    600
gccgtcacag atagattggc ttcagtggag actgatatgc ctctaacatt gagacagcat    660
agaataagtg cgacatcatc atcggaagag agtagtaaca aaggtcaaag acagttgact    720
gtatcgggcg ggtctagaag aatatcgtgg cctgagtgcg tagtacccga gactcagtgc    780
gccatgaagc ggaaagagaa gaaagcacag aaggagaagg acaaactgcc tgtcagcacg    840
acgacggtgg acgaccacat gccgcccatt atgcagtgtg aacctccacc tcctgaagca    900
gcaaggattc acgaagtggt tccaaggttt ctctccgaca agctgttgga gacaaaccgg    960
cagaaaaaca tcccccagtt gacagccaac cagcagttcc ttatcgccag gctcatctgg   1020
taccaggacg ggtacgagca gccttctgat gaagatttga agaggattac gcagacgtgg   1080
cagcaagcgg acgatgaaaa cgaagagtct gacactccct tccgccagat cacagagatg   1140
actatcctca cggtccaact tatcgtggag ttcgcgaagg gattgccagg gttcgccaag   1200
atctcgcagc ctgatcaaat tacgctgctt aaggcttgct caagtgaggt aatgatgctc   1260
cgagtcgcca gatacgatgc ggcctcagac agtgttctgt tcgcgaacaa ccaagcgtac   1320
actcgcgaca actaccgcaa ggctggcatg gcctacgtca tcgaggatct actgcacttc   1380
tgccggtgca tgtactctat ggcgttggac aacatccatt acgcgctgct cacggctgtc   1440
gtcatctttt ctgaccggcc agggttggag cagccgcaac tggtggaaga aatccagcgg   1500
tactacctga atacgctccg catctatatc ctgaaccagc tgagcgggtc ggcgcgttcg   1560
tccgtcatat acggcaagat cctctcaatc ctctctgagc tacgcacgct cggcatgcaa   1620
aactccaaca tgtgcatctc cctcaagctc aagaacagaa agctgccgcc tttcctcgag   1680
gagatctggg atgtggcagg acatgtcgca cacccaaccg ccgcctatct cgagtccccc   1740
acgaatctct agtgacaatc tcccttcacc cgtccccgtt gtcgacccct tccccccata   1800
ttccaggtta acttcccctt cttaagcagc aagaatccca agtggtccca ggtttctttc   1860
ctgcaagccg ttggagtcaa ccggccgaaa aacttccccc agttggcagc caaccagcag   1920
tccctattct ccaggctctt ctggtaccag gacgggtacg agcagccttc tgatgaggat   1980
ttgaagggga ttacgcagac gtggcagcaa gcggacgatg aaatcgaaga gtctgacact   2040
cctttccgcc agatcacaga gatgactatc ctcacggtcc aacttatcgt ggagttcgcg   2100
aagggattgc cagggttcgc caagatctcg cagcctgatc aaattacgct acttaaggct   2160
ttctcaagtg aggtaatgat gctccgagtc gcgcgacgat acgatgcgcc ctcagacagt   2220
```

-continued

```
gttctggtcg cgaacaacca agcgtacact cgcgacaact accgcaaggc tggcatggcc   2280

tacgtcatcg aggatctact gcacttctgc cggtgcatgt actctatggc gttggacaac   2340

atccattacg cgctgctcac ggctgtcgtc atcttttctg accggccagg gttggagcag   2400

ccgcaactgg tggaagagat ccagcggtac tacctgaata cgctccgcat ctatatcctg   2460

aaccagctga gcgggtcggc gcgttcgtcc gtcatatacg gcaagatcct ctcaatcctc   2520

tctgagctac gcacgctcgg catgcaaaac tccaacatgt gcatctccct caagctcaag   2580

aacagaaagc tgtaa                                                    2595
```

<210> SEQ ID NO 94
<211> LENGTH: 28
<212> TYPE: DNA
<213> ORGANISM: Artificial
<220> FEATURE:
<223> OTHER INFORMATION: Primer sequence that hybridizes to the coding sequence for the synthetic 2C7 zinc finger protein

<400> SEQUENCE: 94

```
gccagatcta tgggccacag gcgcgccc                                        28
```

<210> SEQ ID NO 95
<211> LENGTH: 25
<212> TYPE: DNA
<213> ORGANISM: Artificial
<220> FEATURE:
<223> OTHER INFORMATION: Primer sequence that hybridizes to the coding sequence for the synthetic 2C7 zinc finger protein

<400> SEQUENCE: 95

```
cgcggatcct ccatgggcgg cggcg                                           25
```

<210> SEQ ID NO 96
<211> LENGTH: 27
<212> TYPE: DNA
<213> ORGANISM: Artificial
<220> FEATURE:
<223> OTHER INFORMATION: Primer sequence that hybridizes to the coding sequence for the synthetic 2C7 zinc finger protein

<400> SEQUENCE: 96

```
cgcagatcta tggcggccgc cggcggc                                         27
```

<210> SEQ ID NO 97
<211> LENGTH: 28
<212> TYPE: DNA
<213> ORGANISM: Artificial
<220> FEATURE:
<223> OTHER INFORMATION: Primer sequence that hybridizes to the coding sequence for the synthetic 2C7 zinc finger protein

<400> SEQUENCE: 97

```
cgcggatccg ttcagcttct ccacgtcg                                        28
```

<210> SEQ ID NO 98
<211> LENGTH: 30
<212> TYPE: DNA
<213> ORGANISM: Artificial
<220> FEATURE:
<223> OTHER INFORMATION: Primer used to amplify sequence from rice (Ordyza sp.)

<400> SEQUENCE: 98

```
cgcagatcta tggagatcct gagcctcccc                                      30
```

-continued

<210> SEQ ID NO 99
<211> LENGTH: 27
<212> TYPE: DNA
<213> ORGANISM: Artificial
<220> FEATURE:
<223> OTHER INFORMATION: Primer used to amplify sequence from Rice (Ordyza sp.)

<400> SEQUENCE: 99
cgcggatccc tcctcgtcgt tctcgtc 27

<210> SEQ ID NO 100
<211> LENGTH: 584
<212> TYPE: PRT
<213> ORGANISM: Artificial
<220> FEATURE:
<223> OTHER INFORMATION: Chimeric VGE receptor, comprising the acidic domain of the SV40 virus (Simian virus 40), the Gal4 protein from Baker's yeast (Salmonella sp.), and the ecdysone receptor of Cloristoneura fumiferana

<400> SEQUENCE: 100

```
Met Ala Pro Pro Thr Asp Val Ser Leu Gly Asp Glu Leu His Leu Asp
1               5                   10                  15

Gly Glu Asp Val Ala Met Ala His Ala Asp Ala Leu Asp Asp Phe Asp
            20                  25                  30

Leu Asp Met Leu Gly Asp Gly Asp Ser Pro Gly Pro Gly Phe Thr Pro
        35                  40                  45

His Asp Ser Ala Pro Tyr Gly Ala Leu Asp Met Ala Asp Phe Glu Phe
    50                  55                  60

Glu Gln Met Phe Thr Asp Ala Leu Gly Ile Asp Glu Tyr Gly Gly Lys
65                  70                  75                  80

Leu Leu Gly Thr Ser Arg Arg Ile Ser Gly Gly Glu Phe Gly Gly Met
                85                  90                  95

Lys Leu Leu Ser Ser Ile Glu Gln Ala Cys Asp Ile Cys Arg Leu Lys
            100                 105                 110

Lys Leu Lys Cys Ser Lys Glu Lys Pro Lys Cys Ala Lys Cys Leu Lys
        115                 120                 125

Asn Asn Trp Glu Cys Arg Tyr Ser Pro Lys Thr Lys Arg Ser Pro Leu
    130                 135                 140

Thr Arg Ala His Leu Thr Glu Val Glu Ser Arg Leu Glu Arg Leu Glu
145                 150                 155                 160

Gln Leu Phe Leu Leu Ile Phe Pro Arg Glu Asp Leu Asp Met Ile Leu
                165                 170                 175

Lys Met Asp Ser Leu Gln Asp Ile Lys Ala Leu Leu Thr Gly Leu Phe
            180                 185                 190

Val Gln Asp Asn Val Asn Lys Asp Ala Val Thr Asp Arg Leu Ala Ser
        195                 200                 205

Val Glu Thr Asp Met Pro Leu Thr Leu Arg Gln His Arg Ile Ser Ala
    210                 215                 220

Thr Ser Ser Ser Glu Glu Ser Ser Asn Lys Gly Gln Arg Gln Leu Thr
225                 230                 235                 240

Val Ser Gly Gly Ser Arg Arg Ile Ser Trp Pro Glu Cys Val Val Pro
                245                 250                 255

Glu Thr Gln Cys Ala Met Lys Arg Lys Glu Lys Lys Ala Gln Lys Glu
            260                 265                 270

Lys Asp Lys Leu Pro Val Ser Thr Thr Thr Val Asp Asp His Met Pro
```

-continued

```
        275                 280                 285

Pro Ile Met Gln Cys Glu Pro Pro Pro Pro Glu Ala Ala Arg Ile His
    290                 295                 300

Glu Val Val Pro Arg Phe Leu Ser Asp Lys Leu Leu Glu Thr Asn Arg
305                 310                 315                 320

Gln Lys Asn Ile Pro Gln Leu Thr Ala Asn Gln Gln Phe Leu Ile Ala
                325                 330                 335

Arg Leu Ile Trp Tyr Gln Asp Gly Tyr Glu Gln Pro Ser Asp Glu Asp
            340                 345                 350

Leu Lys Arg Ile Thr Gln Thr Trp Gln Gln Ala Asp Asp Glu Asn Glu
        355                 360                 365

Glu Ser Asp Thr Pro Phe Arg Gln Ile Thr Glu Met Thr Ile Leu Thr
    370                 375                 380

Val Gln Leu Ile Val Glu Phe Ala Lys Gly Leu Pro Gly Phe Ala Lys
385                 390                 395                 400

Ile Ser Gln Pro Asp Gln Ile Thr Leu Leu Lys Ala Phe Ser Ser Glu
                405                 410                 415

Val Met Met Leu Arg Val Ala Arg Arg Tyr Asp Ala Ala Ser Asp Ser
            420                 425                 430

Val Leu Phe Ala Asn Asn Gln Ala Tyr Thr Arg Asp Asn Tyr Arg Lys
        435                 440                 445

Ala Gly Met Ala Tyr Val Ile Glu Asp Leu Leu His Phe Cys Arg Cys
    450                 455                 460

Met Tyr Ser Met Ala Leu Asp Asn Ile His Tyr Ala Leu Leu Thr Ala
465                 470                 475                 480

Val Val Ile Phe Ser Asp Arg Pro Gly Leu Glu Gln Pro Gln Leu Val
                485                 490                 495

Glu Glu Ile Gln Arg Tyr Tyr Leu Asn Thr Leu Arg Ile Tyr Ile Leu
            500                 505                 510

Asn Gln Leu Ser Gly Ser Ala Arg Ser Ser Val Ile Tyr Gly Lys Ile
        515                 520                 525

Leu Ser Ile Leu Ser Glu Leu Arg Thr Leu Gly Met Gln Asn Ser Asn
    530                 535                 540

Met Cys Ile Ser Leu Lys Leu Lys Asn Arg Lys Leu Pro Pro Phe Leu
545                 550                 555                 560

Glu Glu Ile Trp Asp Val Ala Asp Met Ser His Thr Gln Pro Pro Pro
                565                 570                 575

Ile Leu Glu Ser Pro Thr Asn Leu
            580


<210> SEQ ID NO 101
<211> LENGTH: 29
<212> TYPE: PRT
<213> ORGANISM: Oryza sp.

<400> SEQUENCE: 101

Glu Ile Leu Ser Leu Pro Glu Asp Leu Asp Leu Cys Ala Ala Gly Gly
1               5                   10                  15

Gly Asp Gly Pro Ser Leu Ser Asp Glu Asn Asp Glu Glu
            20                  25


<210> SEQ ID NO 102
<211> LENGTH: 87
<212> TYPE: DNA
<213> ORGANISM: Oryza sp.
```

-continued

<400> SEQUENCE: 102
gagatcctga gcctccccga ggacctcgac ctgtgcgcgg ccggcggcgg cgacgggccg 60
tcgctgtcgg acgagaacga cgaggag 87

<210> SEQ ID NO 103
<211> LENGTH: 488
<212> TYPE: PRT
<213> ORGANISM: Artificial
<220> FEATURE:
<223> OTHER INFORMATION: A combination of the Gal4 protein and Ecdysone receptor

<400> SEQUENCE: 103

Lys Leu Leu Ser Ser Ile Glu Gln Ala Cys Asp Ile Cys Arg Leu Lys
1 5 10 15

Lys Leu Lys Cys Ser Lys Glu Lys Pro Lys Cys Ala Lys Cys Leu Lys
20 25 30

Asn Asn Trp Glu Cys Arg Tyr Ser Pro Lys Thr Lys Arg Ser Pro Leu
35 40 45

Thr Arg Ala His Leu Thr Glu Val Glu Ser Arg Leu Glu Arg Leu Glu
50 55 60

Gln Leu Phe Leu Leu Ile Phe Pro Arg Glu Asp Leu Asp Met Ile Leu
65 70 75 80

Lys Met Asp Ser Leu Gln Asp Ile Lys Ala Leu Leu Thr Gly Leu Phe
85 90 95

Val Gln Asp Asn Val Asn Lys Asp Ala Val Thr Asp Arg Leu Ala Ser
100 105 110

Val Glu Thr Asp Met Pro Leu Thr Leu Arg Gln His Arg Ile Ser Ala
115 120 125

Thr Ser Ser Ser Glu Glu Ser Ser Asn Lys Gly Gln Arg Gln Leu Thr
130 135 140

Val Ser Gly Gly Ser Arg Arg Ile Ser Trp Pro Glu Cys Val Val Pro
145 150 155 160

Glu Thr Gln Cys Ala Met Lys Arg Lys Glu Lys Lys Ala Gln Lys Glu
165 170 175

Lys Asp Lys Leu Pro Val Ser Thr Thr Thr Val Asp Asp His Met Pro
180 185 190

Pro Ile Met Gln Cys Glu Pro Pro Pro Pro Glu Ala Ala Arg Ile His
195 200 205

Glu Val Val Pro Arg Phe Leu Ser Asp Lys Leu Leu Glu Thr Asn Arg
210 215 220

Gln Lys Asn Ile Pro Gln Leu Thr Ala Asn Gln Gln Phe Leu Ile Ala
225 230 235 240

Arg Leu Ile Trp Tyr Gln Asp Gly Tyr Glu Gln Pro Ser Asp Glu Asp
245 250 255

Leu Lys Arg Ile Thr Gln Thr Trp Gln Gln Ala Asp Asp Glu Asn Glu
260 265 270

Glu Ser Asp Thr Pro Phe Arg Gln Ile Thr Glu Met Thr Ile Leu Thr
275 280 285

Val Gln Leu Ile Val Glu Phe Ala Lys Gly Leu Pro Gly Phe Ala Lys
290 295 300

Ile Ser Gln Pro Asp Gln Ile Thr Leu Leu Lys Ala Phe Ser Ser Glu
305 310 315 320

Val Met Met Leu Arg Val Ala Arg Arg Tyr Asp Ala Ala Ser Asp Ser
325 330 335

-continued

```
Val Leu Phe Ala Asn Asn Gln Ala Tyr Thr Arg Asp Asn Tyr Arg Lys
            340                 345                 350

Ala Gly Met Ala Tyr Val Ile Glu Asp Leu Leu His Phe Cys Arg Cys
        355                 360                 365

Met Tyr Ser Met Ala Leu Asp Asn Ile His Tyr Ala Leu Leu Thr Ala
    370                 375                 380

Val Val Ile Phe Ser Asp Arg Pro Gly Leu Glu Gln Pro Gln Leu Val
385                 390                 395                 400

Glu Glu Ile Gln Arg Tyr Tyr Leu Asn Thr Leu Arg Ile Tyr Ile Leu
                405                 410                 415

Asn Gln Leu Ser Gly Ser Ala Arg Ser Ser Val Ile Tyr Gly Lys Ile
            420                 425                 430

Leu Ser Ile Leu Ser Glu Leu Arg Thr Leu Gly Met Gln Asn Ser Asn
        435                 440                 445

Met Cys Ile Ser Leu Lys Leu Lys Asn Arg Lys Leu Pro Pro Phe Leu
    450                 455                 460

Glu Glu Ile Trp Asp Val Ala Asp Met Ser His Thr Gln Pro Pro Pro
465                 470                 475                 480

Ile Leu Glu Ser Pro Thr Asn Leu
                485
```

<210> SEQ ID NO 104
<211> LENGTH: 1464
<212> TYPE: DNA
<213> ORGANISM: Artificial
<220> FEATURE:
<223> OTHER INFORMATION: Nucleic acid sequence encoding SEQ ID NO:103 (a combination of the Gal4 protein and ecdysone receptor)

<400> SEQUENCE: 104

```
aagctactgt cttctatcga acaagcatgc gatatttgcc gacttaaaaa gctcaagtgc      60

tccaaagaaa aaccgaagtg cgccaagtgt ctgaagaaca actgggagtg tcgctactct     120

cccaaaacca aaaggtctcc gctgactagg gcacatctga cagaagtgga atcaaggcta     180

gaaagactgg aacagctatt tctactgatt tttcctcgag aagaccttga catgattttg     240

aaaatggatt ctttacagga tataaaagca ttgttaacag gattatttgt acaagataat     300

gtgaataaag atgccgtcac agatagattg gcttcagtgg agactgatat gcctctaaca     360

ttgagacagc atagaataag tgcgacatca tcatcggaag agagtagtaa caaaggtcaa     420

agacagttga ctgtatcggg cgggtctaga agaatatcgt ggcctgagtg cgtagtaccc     480

gagactcagt gcgccatgaa gcggaaagag aagaaagcac agaaggagaa ggacaaactg     540

cctgtcagca cgacgacggt ggacgaccac atgccgccca ttatgcagtg tgaacctcca     600

cctcctgaag cagcaaggat tcacgaagtg gtcccaaggt ttctctccga caagctgttg     660

gagacaaacc ggcagaaaaa catcccccag ttgacagcca accagcagtt ccttatcgcc     720

aggctcatct ggtaccagga cgggtacgag cagccttctg atgaagattt gaagaggatt     780

acgcagacgt ggcagcaagc ggacgatgaa aacgaagagt ctgacactcc cttccgccag     840

atcacagaga tgactatcct cacggtccaa cttatcgtgg agttcgcgaa gggattgcca     900

gggttcgcca agatctcgca gcctgatcaa attacgctac ttaaggcttt ctcaagtgag     960

gtaatgatgc tccgagtcgc gcgacgatac gatgcggcct cagacagtgt tctgttcgcg    1020

aacaaccaag cgtacactcg cgacaactac cgcaaggctg gcatggccta cgtcatcgag    1080

gatctactgc acttctgccg gtgcatgtac tctatggcgt tggacaacat ccattacgcg    1140
```

-continued

```
ctgctcacgg ctgtcgtcat cttttctgac cggccagggt tggagcagcc gcaactggtg   1200

gaagagatcc agcggtacta cctgaatacg ctccgcatct atatcctgaa ccagctgagc   1260

gggtcggcgc gttcgtccgt catatacggc aagatcctct caatcctctc tgagctacgc   1320

acgctcggca tgcaaaactc caacatgtgc atctccctca agctcaagaa cagaaagctg   1380

ccgcctttcc tcgaggagat ctgggatgtg gcggacatgt cgcacaccca accgccgcct   1440

atcctcgagt cccccacgaa tctc                                           1464
```

<210> SEQ ID NO 105
<211> LENGTH: 334
<212> TYPE: PRT
<213> ORGANISM: Artificial
<220> FEATURE:
<223> OTHER INFORMATION: Ecdysone receptor domain from Cloristoneura fumiferana

<400> SEQUENCE: 105

```
Pro Glu Cys Val Val Pro Glu Thr Gln Cys Ala Met Lys Arg Lys Glu
1               5                   10                  15

Lys Lys Ala Gln Lys Glu Lys Asp Lys Leu Pro Val Ser Thr Thr Thr
            20                  25                  30

Val Asp Asp His Met Pro Pro Ile Met Gln Cys Glu Pro Pro Pro Pro
        35                  40                  45

Glu Ala Ala Arg Ile His Glu Val Val Pro Arg Phe Leu Ser Asp Lys
    50                  55                  60

Leu Leu Glu Thr Asn Arg Gln Lys Asn Ile Pro Gln Leu Thr Ala Asn
65                  70                  75                  80

Gln Gln Phe Leu Ile Ala Arg Leu Ile Trp Tyr Gln Asp Gly Tyr Glu
                85                  90                  95

Gln Pro Ser Asp Glu Asp Leu Lys Arg Ile Thr Gln Thr Trp Gln Gln
            100                 105                 110

Ala Asp Asp Glu Asn Glu Glu Ser Asp Thr Pro Phe Arg Gln Ile Thr
        115                 120                 125

Glu Met Thr Ile Leu Thr Val Gln Leu Ile Val Glu Phe Ala Lys Gly
    130                 135                 140

Leu Pro Gly Phe Ala Lys Ile Ser Gln Pro Asp Gln Ile Thr Leu Leu
145                 150                 155                 160

Lys Ala Phe Ser Ser Glu Val Met Met Leu Arg Val Ala Arg Arg Tyr
                165                 170                 175

Asp Ala Ala Ser Asp Ser Val Leu Phe Ala Asn Asn Gln Ala Tyr Thr
            180                 185                 190

Arg Asp Asn Tyr Arg Lys Ala Gly Met Ala Tyr Val Ile Glu Asp Leu
        195                 200                 205

Leu His Phe Cys Arg Cys Met Tyr Ser Met Ala Leu Asp Asn Ile His
    210                 215                 220

Tyr Ala Leu Leu Thr Ala Val Val Ile Phe Ser Asp Arg Pro Gly Leu
225                 230                 235                 240

Glu Gln Pro Gln Leu Val Glu Glu Ile Gln Arg Tyr Tyr Leu Asn Thr
                245                 250                 255

Leu Arg Ile Tyr Ile Leu Asn Gln Leu Ser Gly Ser Ala Arg Ser Ser
            260                 265                 270

Val Ile Tyr Gly Lys Ile Leu Ser Ile Leu Ser Glu Leu Arg Thr Leu
        275                 280                 285

Gly Met Gln Asn Ser Asn Met Cys Ile Ser Leu Lys Leu Lys Asn Arg
```

-continued

```
    290                 295                 300

Lys Leu Pro Pro Phe Leu Glu Glu Ile Trp Asp Val Ala Asp Met Ser
305                 310                 315                 320

His Thr Gln Pro Pro Pro Ile Leu Glu Ser Pro Thr Asn Leu
                325                 330


<210> SEQ ID NO 106
<211> LENGTH: 1002
<212> TYPE: DNA
<213> ORGANISM: Artificial
<220> FEATURE:
<223> OTHER INFORMATION: Nucleic acid sequence encoding the ecdysone
      receptor domain from Cloristoneura fumiferana

<400> SEQUENCE: 106

cctgagtgcg tagtacccga gactcagtgc gccatgaagc ggaaagagaa gaaagcacag      60

aaggagaagg acaaactgcc tgtcagcacg acgacggtgg acgaccacat gccgcccatt     120

atgcagtgtg aacctccacc tcctgaagca gcaaggattc acgaagtggt cccaaggttt     180

ctctccgaca agctgttgga gacaaaccgg cagaaaaaca tcccccagtt gacagccaac     240

cagcagttcc ttatcgccag gctcatctgg taccaggacg ggtacgagca gccttctgat     300

gaagatttga agaggattac gcagacgtgg cagcaagcgg acgatgaaaa cgaagagtct     360

gacactccct tccgccagat cacagagatg actatcctca cggtccaact tatcgtggag     420

ttcgcgaagg gattgccagg gttcgccaag atctcgcagc ctgatcaaat tacgctactt     480

aaggcttcct caagtgaggt aatgatgctc cgagtcgcgc gacgatacga tgcggcctca     540

gacagtgttc tgttcgcgaa caaccaagcg tacactcgcg acaactaccg caaggctggc     600

atggcctacg tcatcgagga tctactgcac ttctgccggt gcatgtactc tatggcgttg     660

gacaacatcc attacgcgct gctcacggct gtcgtcatct ttctgaccg gccagggttg      720

gagcagccgc aactggtgga agagatccag cggtactacc tgaatacgct ccgcatctat     780

atcctgaacc agctgagcgg gtcggcgcgt tcgtccgtca tatacggcaa gatcctctca     840

atcctctctg agctacgcac gctcggcatg caaaactcca acatgtgcat ctccctcaag     900

ctcaagaaca gaaagctgcc gcctttcctc gaggagatct gggatgtggc ggacatgtcg     960

cacacccaac cgccgcctat cctcgagtcc cccacgaatc tc                      1002


<210> SEQ ID NO 107
<211> LENGTH: 154
<212> TYPE: PRT
<213> ORGANISM: Salmonella sp.

<400> SEQUENCE: 107

Lys Leu Leu Ser Ser Ile Glu Gln Ala Cys Asp Ile Cys Arg Leu Lys
1               5                   10                  15

Lys Leu Lys Cys Ser Lys Glu Lys Pro Lys Cys Ala Lys Cys Leu Lys
            20                  25                  30

Asn Asn Trp Glu Cys Arg Tyr Ser Pro Lys Thr Lys Arg Ser Pro Leu
        35                  40                  45

Thr Arg Ala His Leu Thr Glu Val Glu Ser Arg Leu Glu Arg Leu Glu
    50                  55                  60

Gln Leu Phe Leu Leu Ile Phe Pro Arg Glu Asp Leu Asp Met Ile Leu
65                  70                  75                  80

Lys Met Asp Ser Leu Gln Asp Ile Lys Ala Leu Leu Thr Gly Leu Phe
                85                  90                  95
```

-continued

```
Val Gln Asp Asn Val Asn Lys Asp Ala Val Thr Asp Arg Leu Ala Ser
            100                 105                 110

Val Glu Thr Asp Met Pro Leu Thr Leu Arg Gln His Arg Ile Ser Ala
        115                 120                 125

Thr Ser Ser Ser Glu Glu Ser Ser Asn Lys Gly Gln Arg Gln Leu Thr
    130                 135                 140

Val Ser Gly Gly Ser Arg Arg Ile Ser Trp
145                 150


<210> SEQ ID NO 108
<211> LENGTH: 93
<212> TYPE: DNA
<213> ORGANISM: Salmonella sp.

<400> SEQUENCE: 108

ctcggaggac agtactccgc tcggaggaca gtactccgct cgaggacagt actccgctcg      60

aggacagtac tccgctcgga ggacagtact ccg                                   93


<210> SEQ ID NO 109
<211> LENGTH: 10
<212> TYPE: PRT
<213> ORGANISM: Artificial
<220> FEATURE:
<223> OTHER INFORMATION: Sequence signature of the DNA-binding regions
<220> FEATURE:
<221> NAME/KEY: misc_feature
<222> LOCATION: (2)..(4)
<223> OTHER INFORMATION: Xaa can be naturally occurring amino acid
<220> FEATURE:
<221> NAME/KEY: misc_feature
<222> LOCATION: (7)..(8)
<223> OTHER INFORMATION: Xaa can be naturally occurring amino acid

<400> SEQUENCE: 109

Asn Xaa Xaa Xaa Ser Ala Xaa Xaa Ser Lys
1               5                   10
```